(12) United States Patent
Allen et al.

(10) Patent No.: US 6,218,163 B1
(45) Date of Patent: Apr. 17, 2001

(54) STABLE BIOCATALYSTS FOR ESTER HYDROLYSIS

(75) Inventors: Larry Allen, Northfield; John Aikens, LaGrange Park; David Demirjian, Chicago; Veronika Vonstein, Chicago; Michael Fonstein, Chicago; Malcolm Casadaban, Chicago, all of IL (US)

(73) Assignee: Thermogen, Inc., Chicago, IL (US)

( * ) Notice: Subject to any disclaimer, the term of this patent is extended or adjusted under 35 U.S.C. 154(b) by 0 days.

(21) Appl. No.: 08/694,078

(22) Filed: Aug. 8, 1996

Related U.S. Application Data

(60) Provisional application No. 60/019,580, filed on Jun. 12, 1996, provisional application No. 60/009,704, filed on Jan. 11, 1996, and provisional application No. 60/001,995, filed on Aug. 7, 1995.

(51) Int. Cl.[7] ............................... C12N 9/18; C12N 1/20; C12N 15/00; C07H 21/04
(52) U.S. Cl. ...................... 435/197; 435/196; 435/252.3; 435/320.1; 435/826; 435/832; 435/839; 435/849; 536/23.2; 530/350
(58) Field of Search .................................... 435/197, 196, 435/252.3, 320.1, 69.1, 826, 832, 839; 536/23.2; 530/350

(56) References Cited

U.S. PATENT DOCUMENTS

| | | | |
|---|---|---|---|
| 4,046,635 | 9/1977 | Moroz | 435/13 |
| 4,259,440 | 3/1981 | Gupta et al. | 435/15 |
| 4,279,994 | 7/1981 | Huang | 435/19 |
| 4,378,429 | 3/1983 | Modrovich | 435/11 |
| 5,273,898 | 12/1993 | Ishii | 435/198 |
| 5,308,765 | 5/1994 | Ozaki et al. | 435/252.3 |

OTHER PUBLICATIONS

Sundaram, T.K., (1988) Thermostable Enzymes for Biotechnology, J. Chem. & Biotech. 42(4):308–311.
Berger et al. (1995). Appl. Microbiol. Biotechnol. 44: 81–87, Dec. 1995.*
Janson (1994). Trends in Biotechnology. 2 (2) : 31–38, 1984.*

* cited by examiner

*Primary Examiner*—Charles L. Patterson, Jr.
*Assistant Examiner*—Tekchand Saidha
(74) *Attorney, Agent, or Firm*—McDonnell Boehnen Hulbert & Berghoff

(57) ABSTRACT

The instant invention encompasses isolated stable esterase enzymes characterized by the ability to remain stable at certain temperatures, substrate specificities, and activity profile.

3 Claims, 53 Drawing Sheets

Figure 2
E001 E002 E003 E004 E005
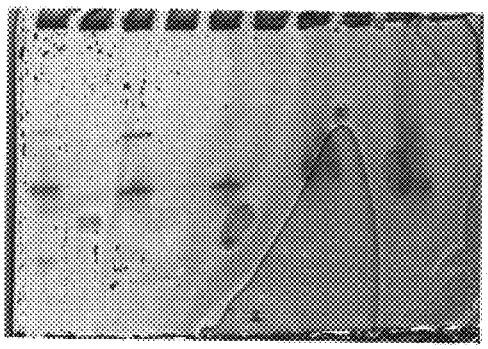
E006 E007 E008 E009 E010
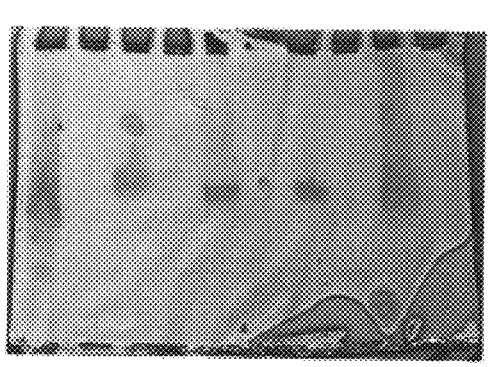
E011 E012 E013 E014 E015
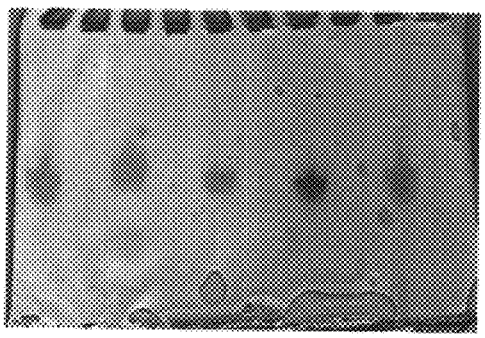
E016 E017 E018 E019 E020 E021
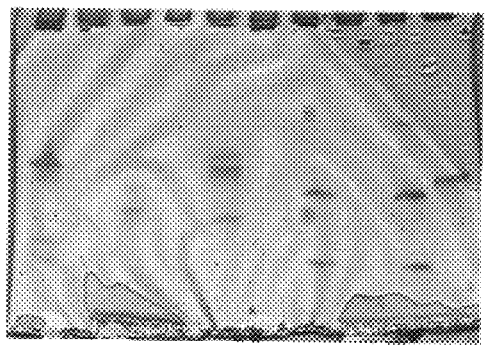

Figure 3. Molecular Weight calibration curve.
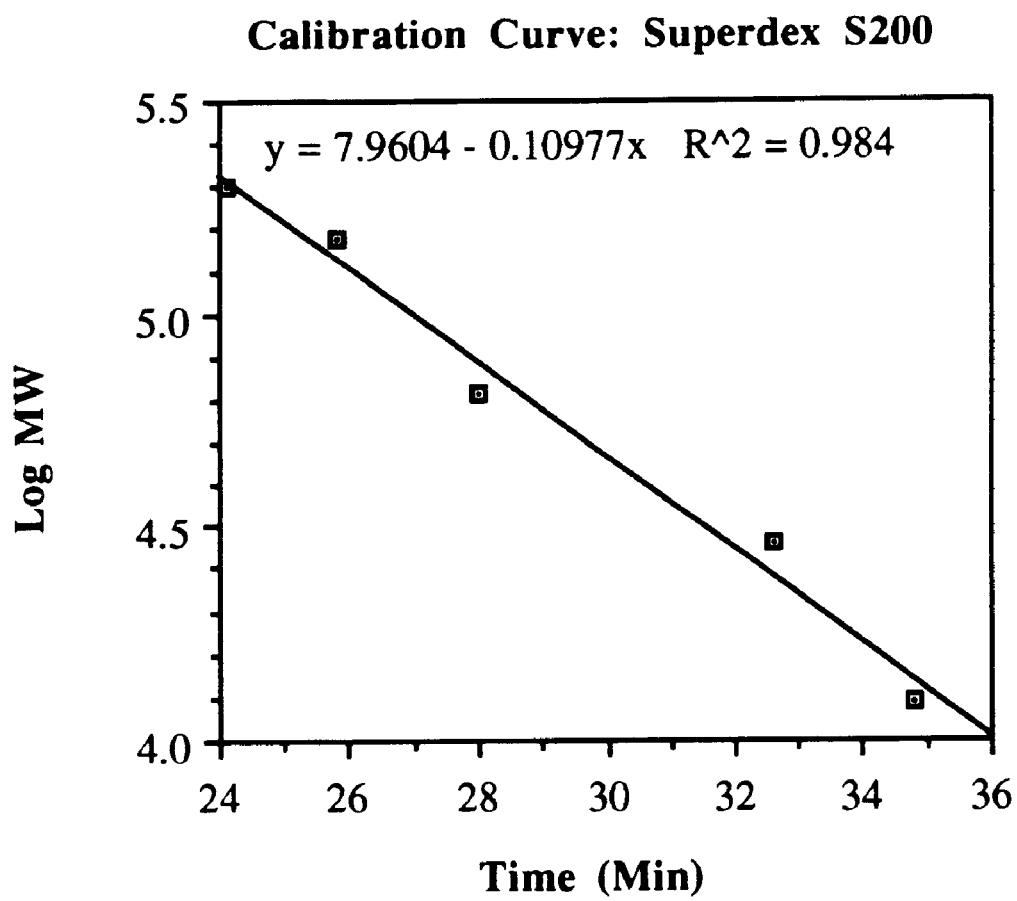

FIGURE 4C
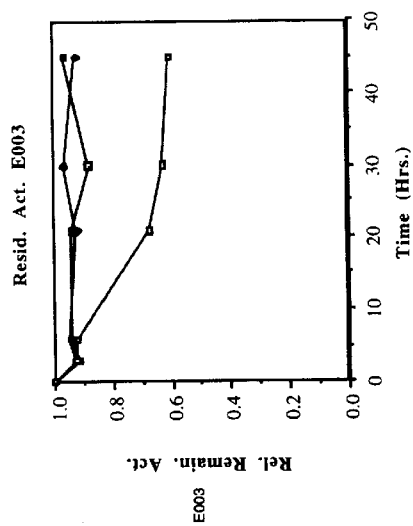
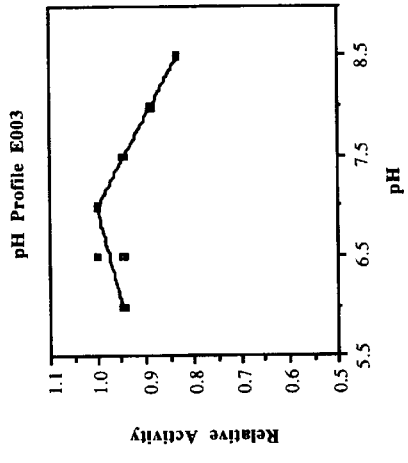
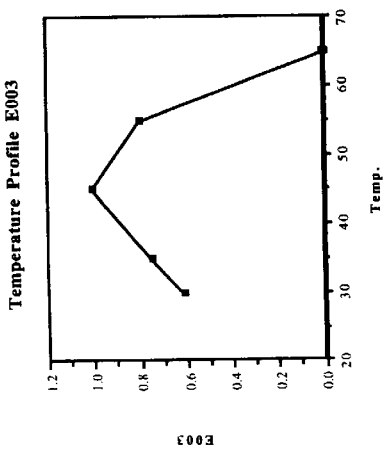

FIGURE 4E
Enzyme Temperature profile / pH profile / Residual Activity profile
E005
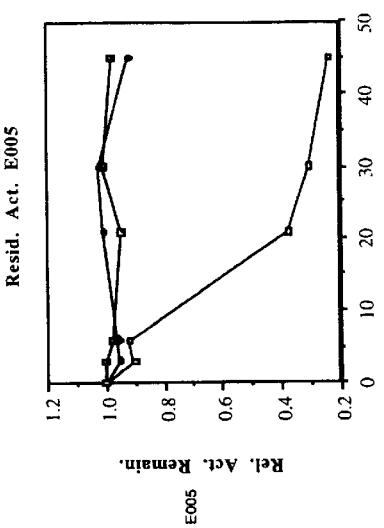
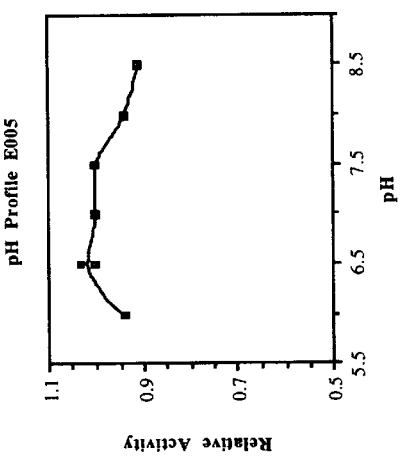
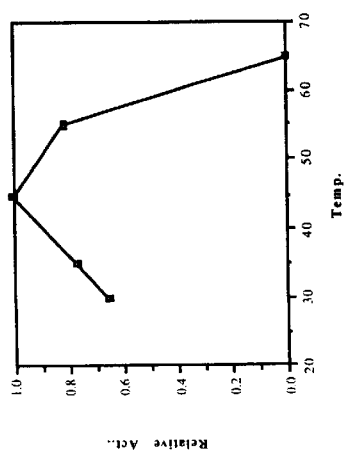

FIGURE 4G
Enzyme E007
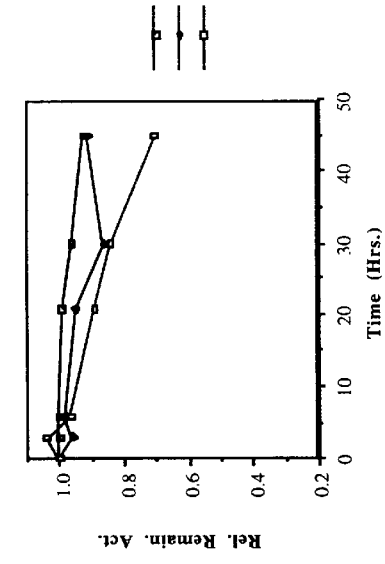
Residual Activity profile
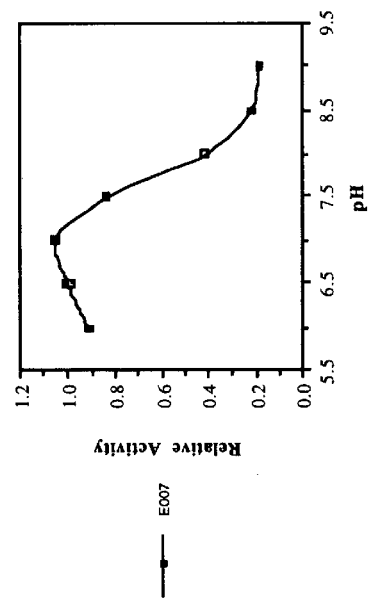
pH profile
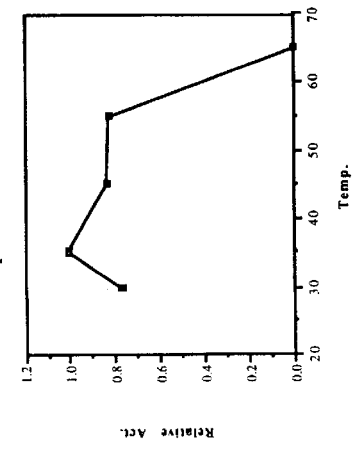
Temperature profile

FIGURE 4J
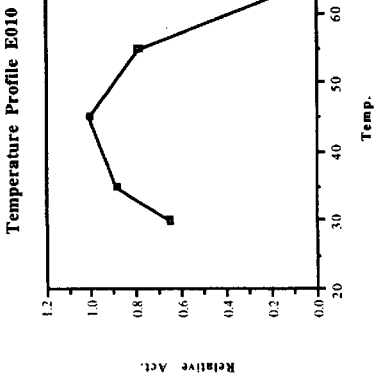
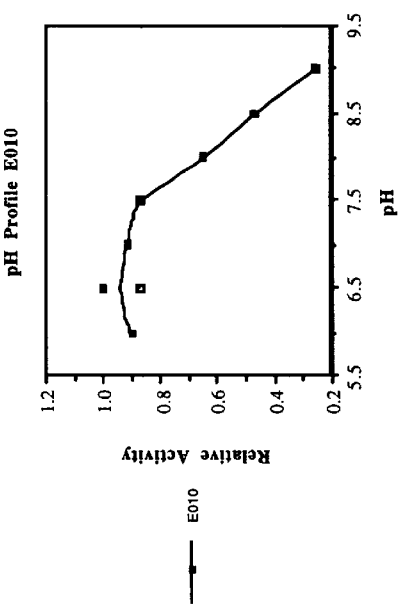
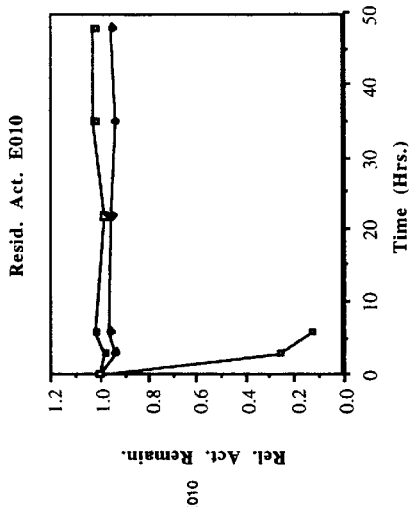

FIGURE 4J
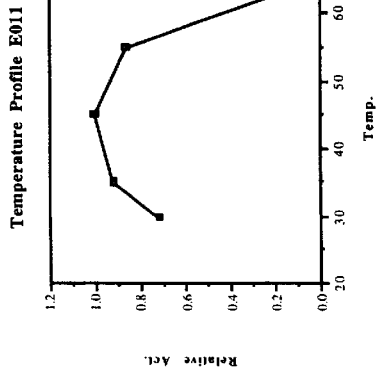
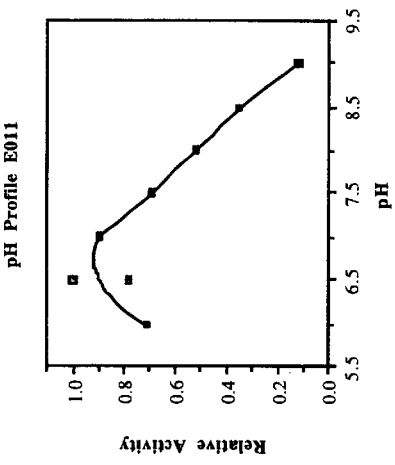
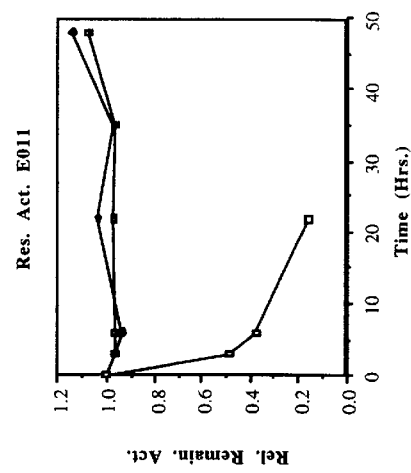

FIGURE 4L
Enzyme Temperature profile E013
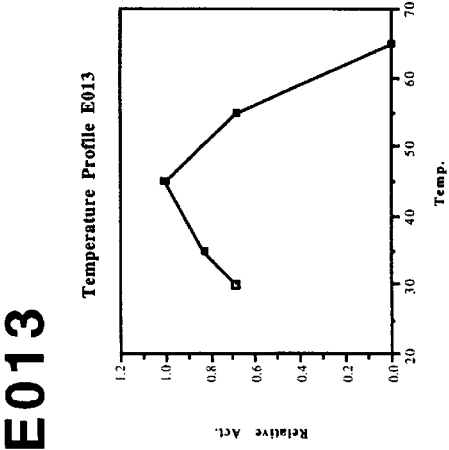
pH profile
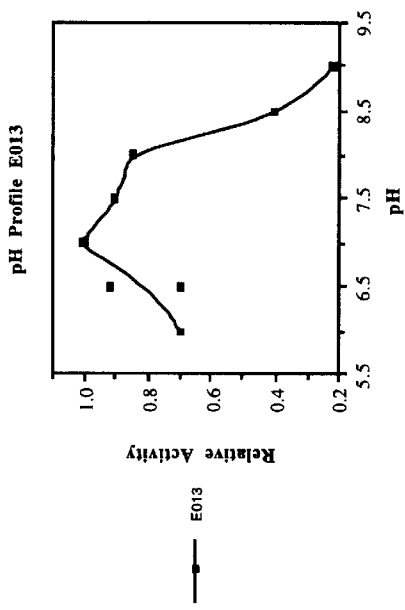
Residual Activity profile
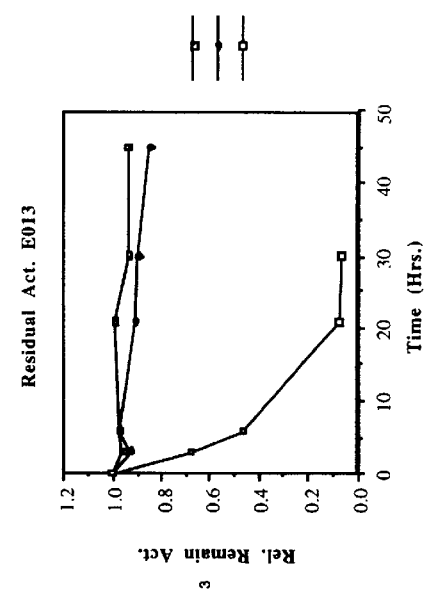

FIGURE 4N
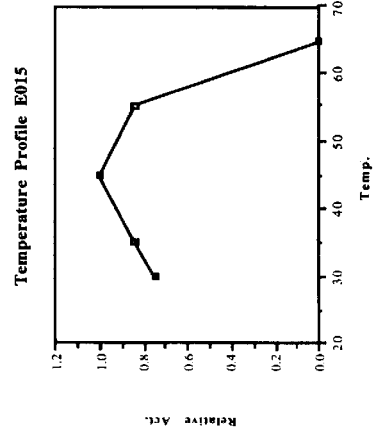
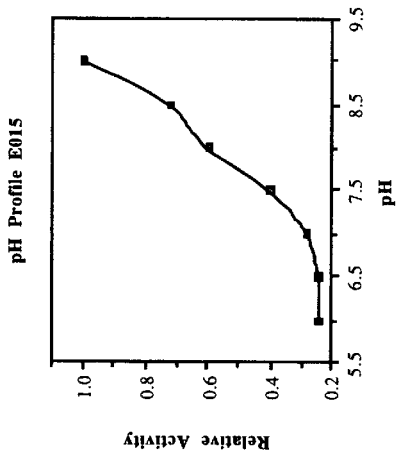
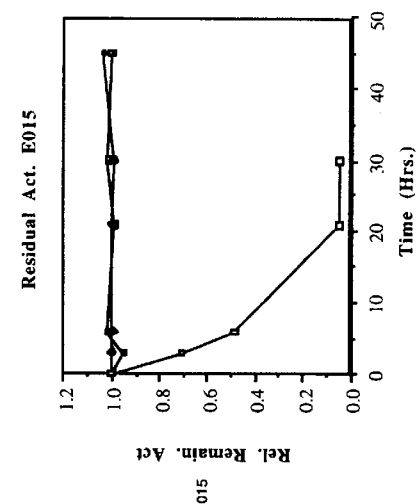
Enzyme E015

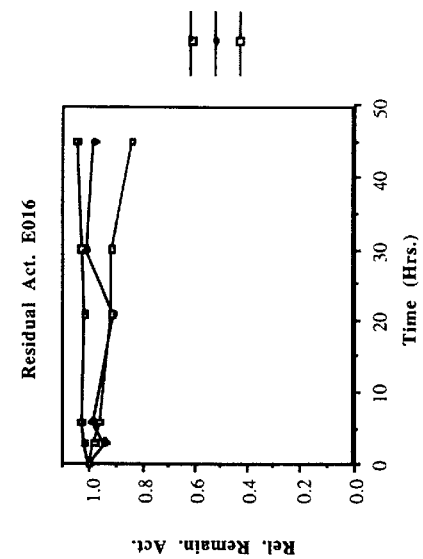
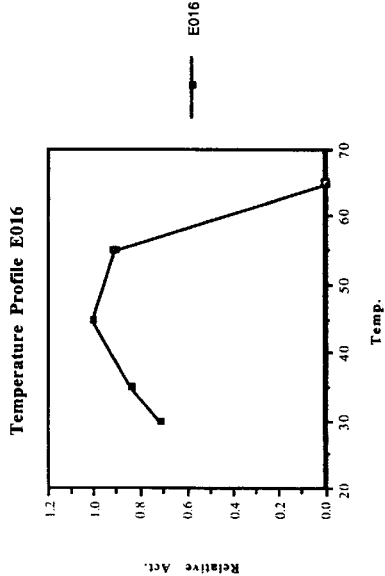
FIGURE 4O

E018

FIGURE 4Q
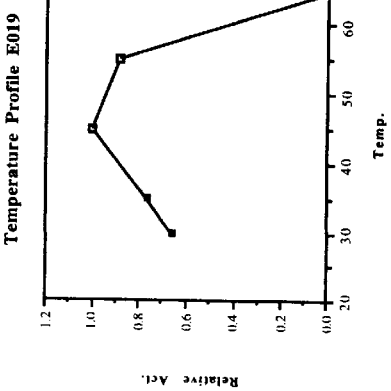
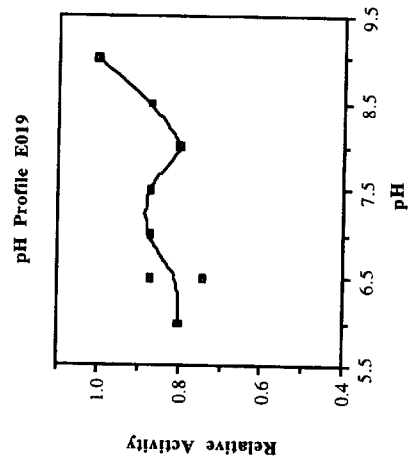
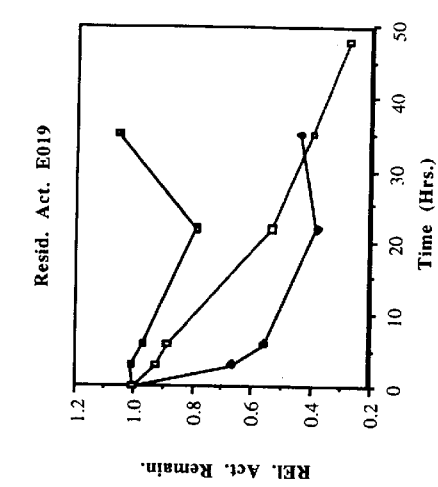
Enzyme Temperature profile
E019

FIGURE 4R
Enzyme Temperature profile
E017b
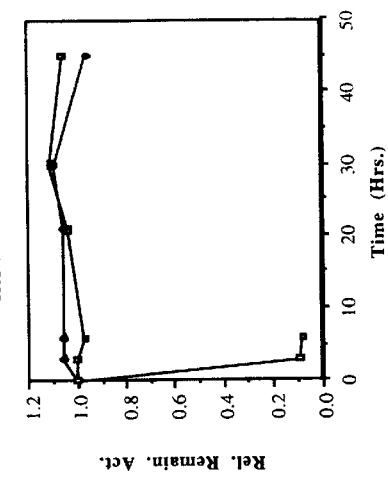
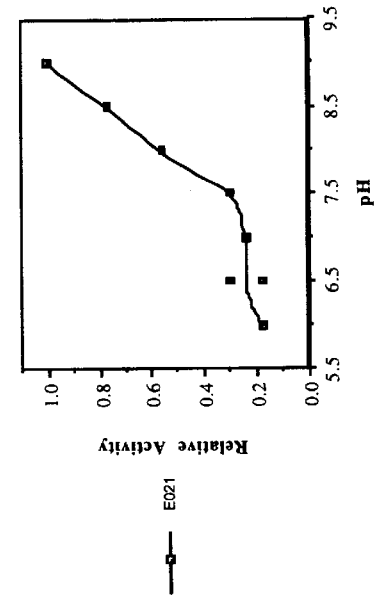
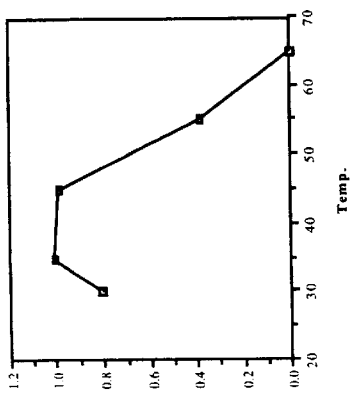

Figure 6
A
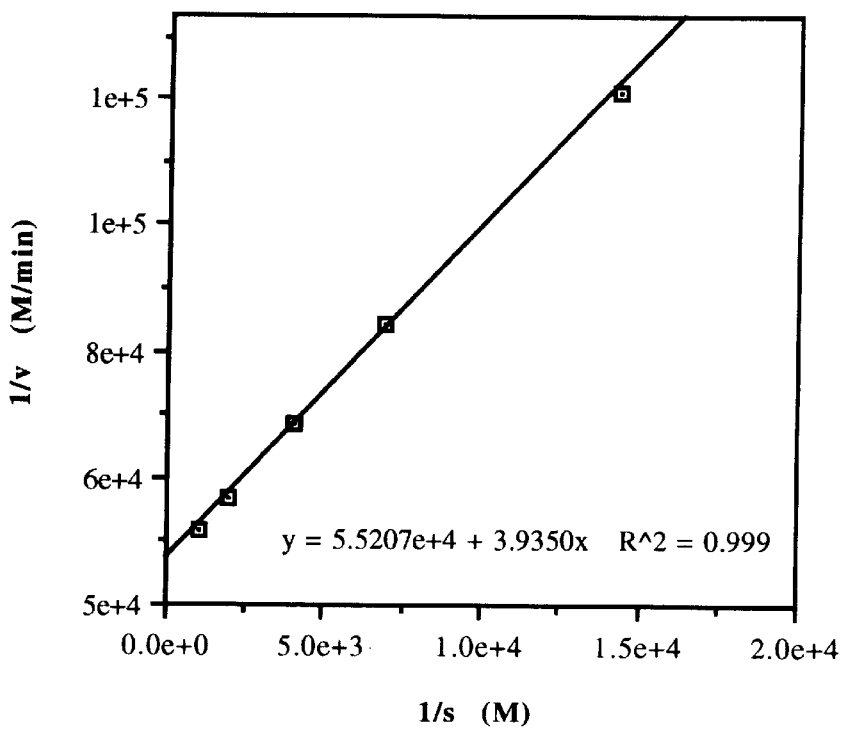
B
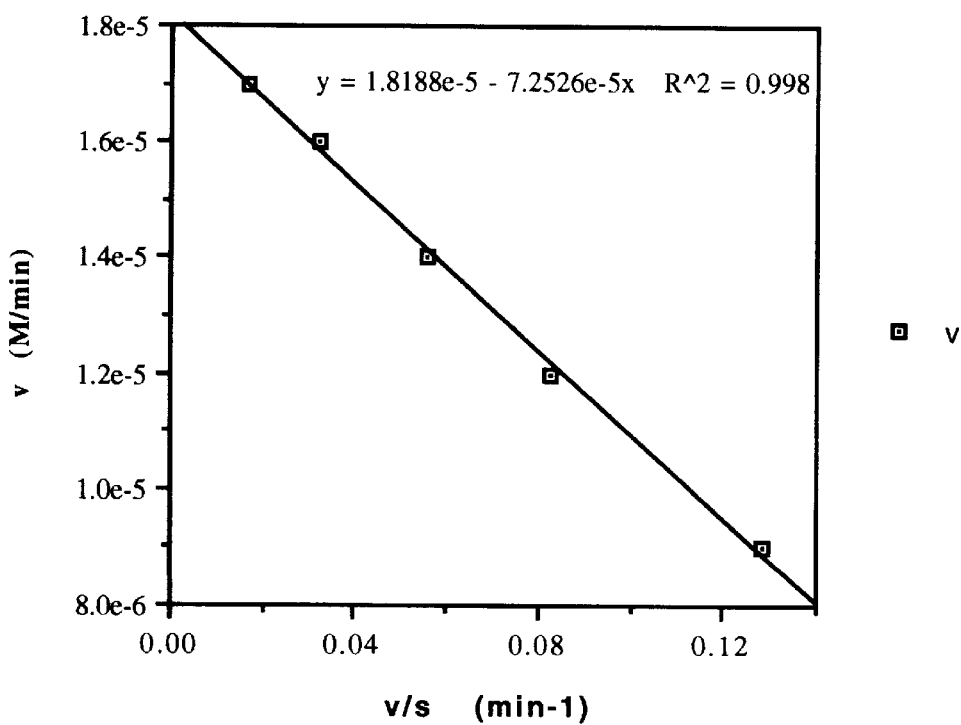

Temperature and pH profiles of E100
a)
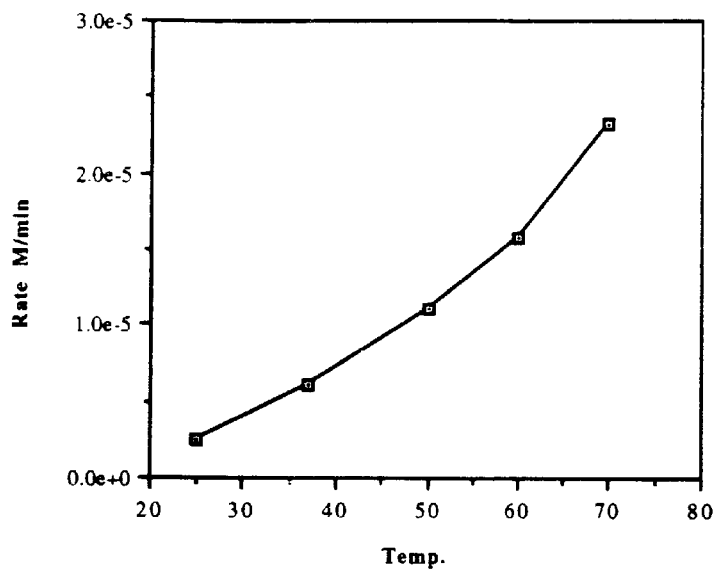
b)
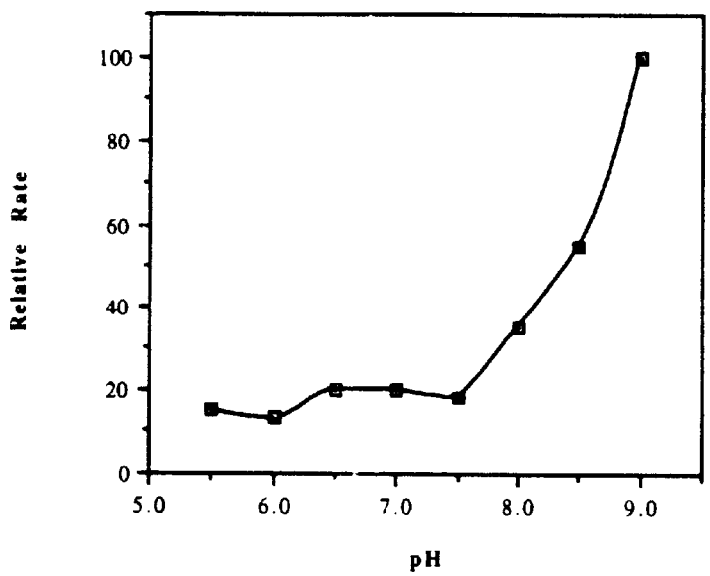
FIGURE 7

Figure 9
a)
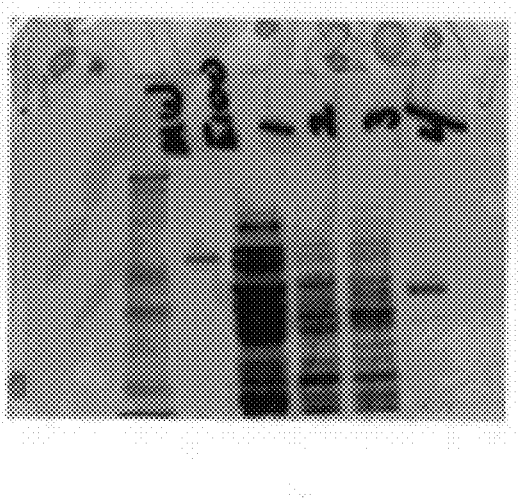
b)
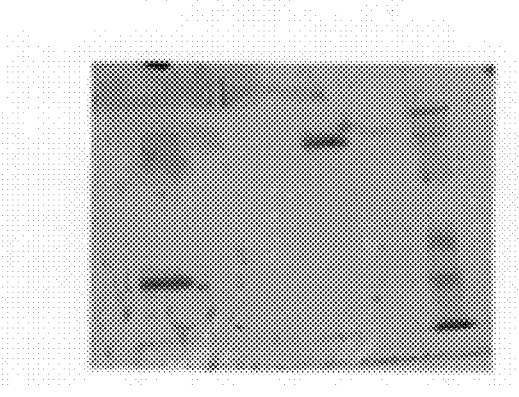

FIGURE 10A
Type I. Chirality on Carboxylate
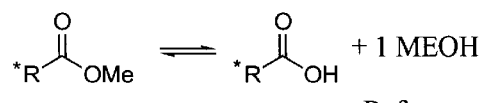
Reference
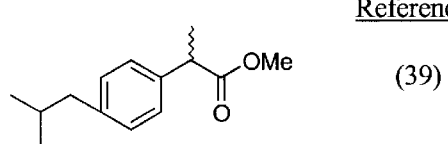
(39)
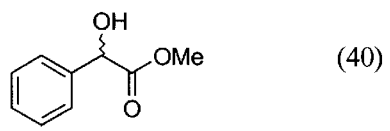
(40)
(40)
(41)
(42)
Type II. Chirality on Alcohol
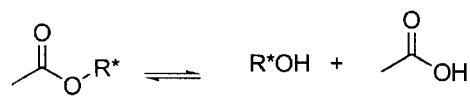
Reference
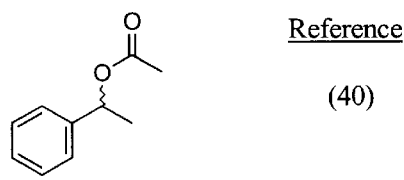
(40)
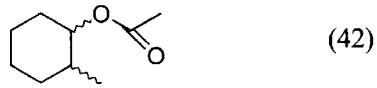
(42)
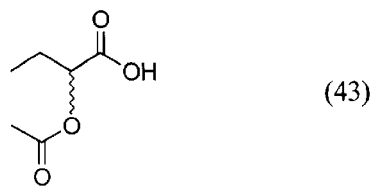
(43)
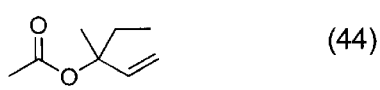
(44)

FIGURE 10B
TYPE III. Chiral Resolution of a Prochiral Center
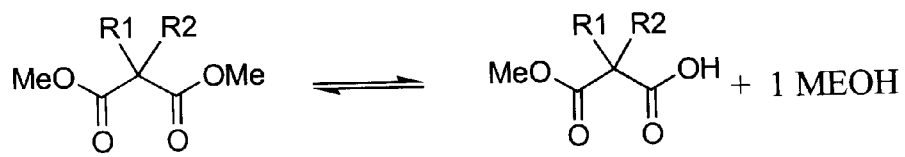
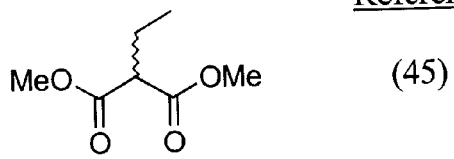
Reference
(45)
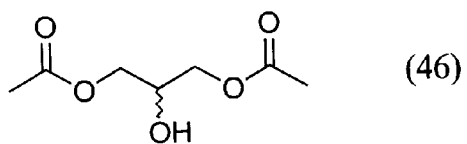
(46)
TYPE IV. Resolution of *Meso* Compounds
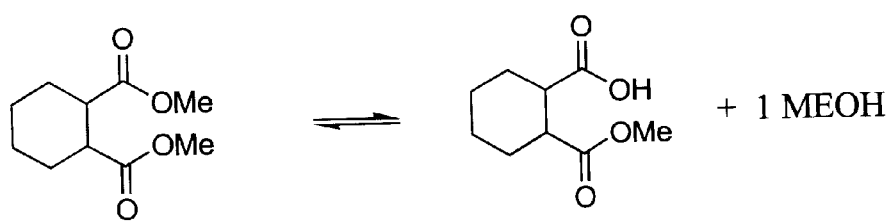
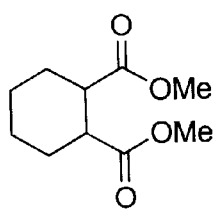  Reference
(42)
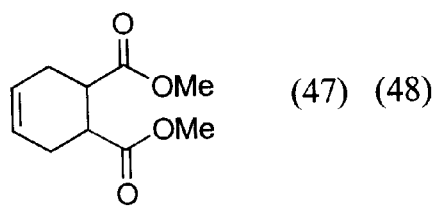
(47) (48)
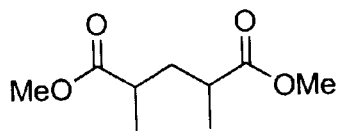  Reference
(49)
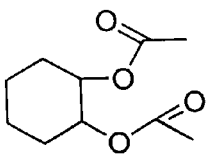
(50)
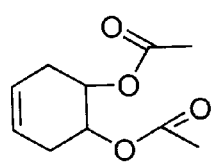
(51)

FIGURE 11
a) 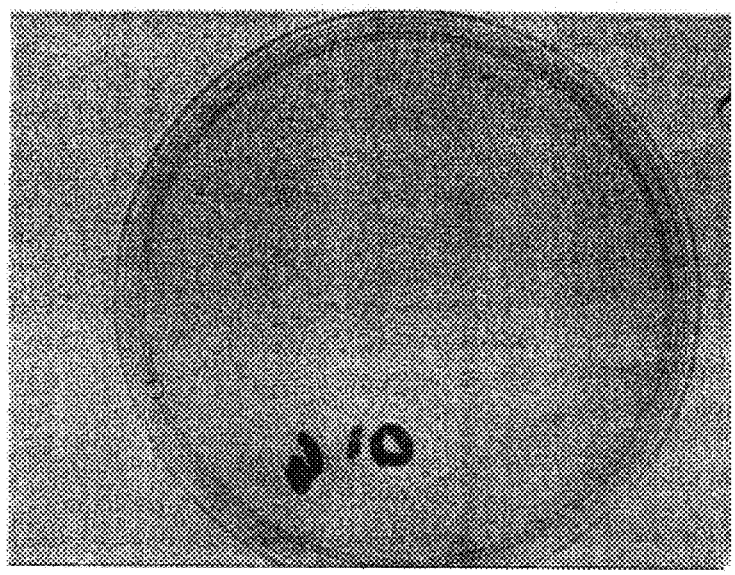
b) 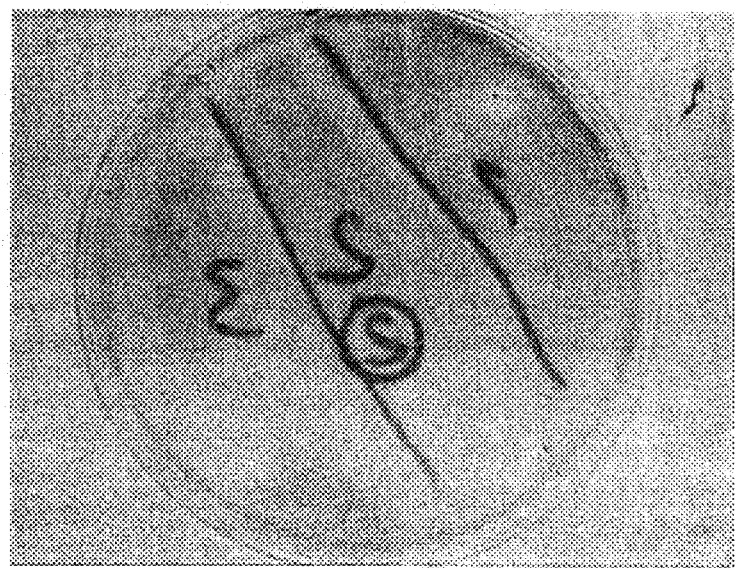

FIGURE 11
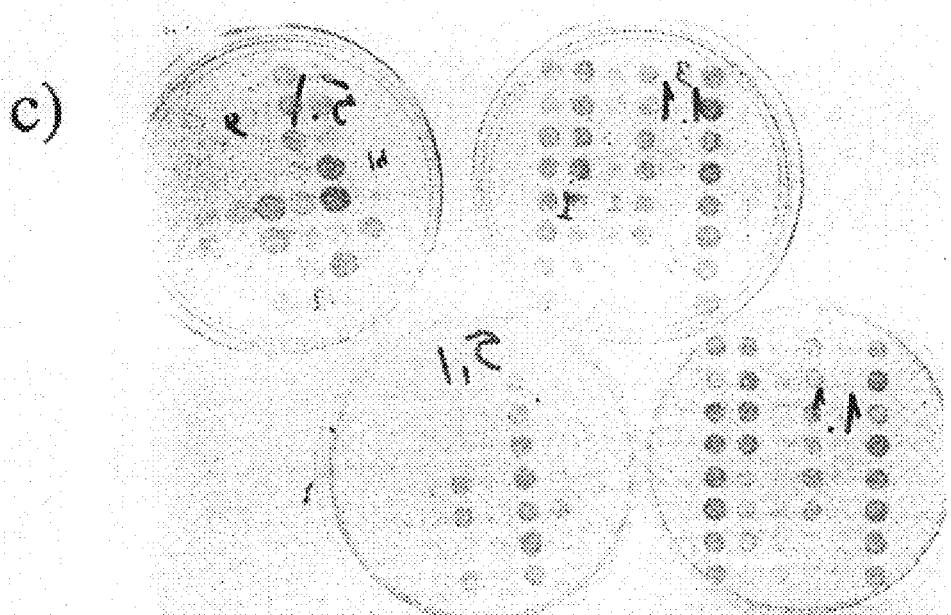
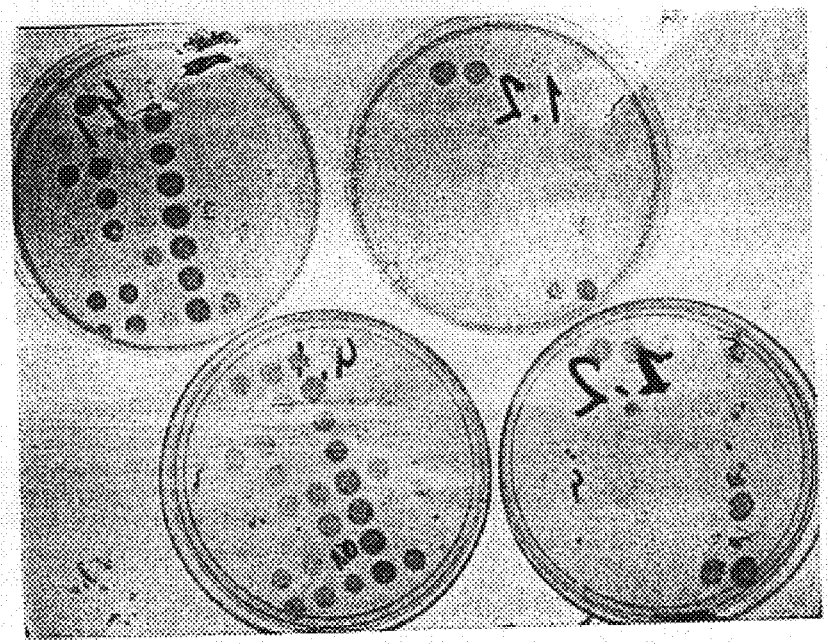

Figure 12
a) Screening positive lambda clones for E001 activity
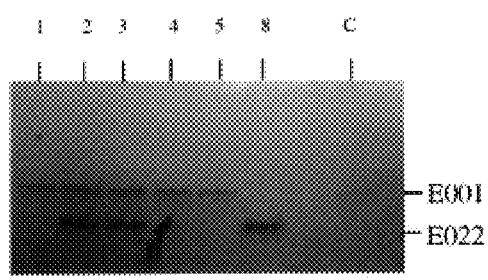
b) Screening positive lambda clones for E002 activity
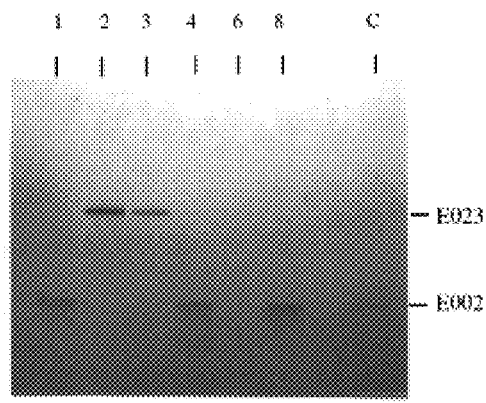
c) Screening positive lambda clones for E003 activity
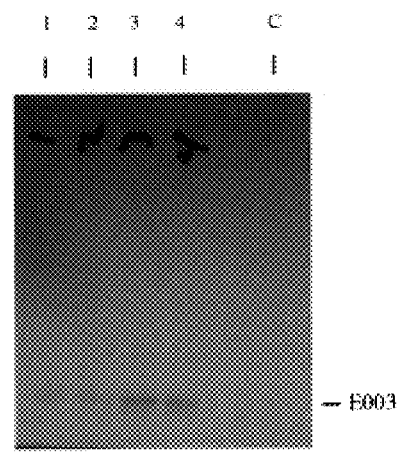
d) Screening positive lambda clones for E004 activity
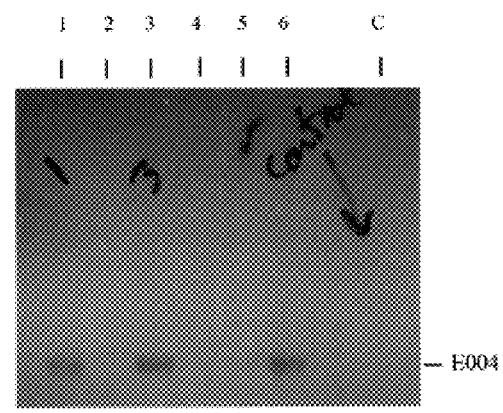

e) Screening positive lambda clones for E005 activity
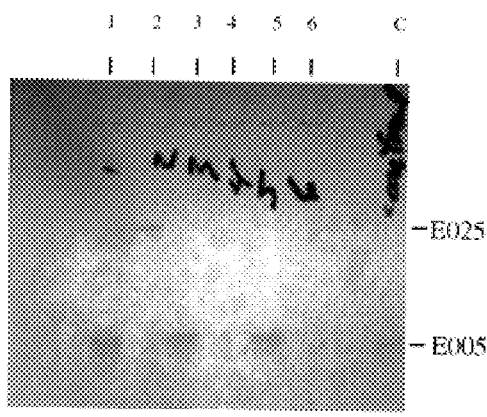
f) Screening positive lambda clones for E006 activity
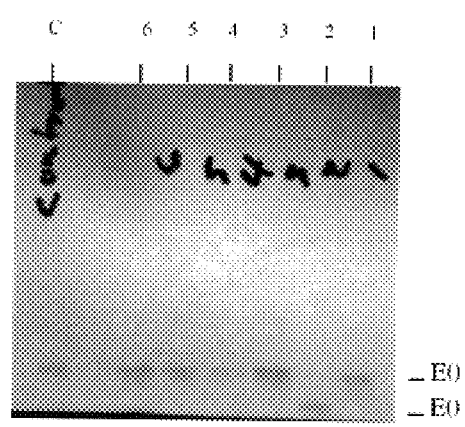
g) Screening positive lambda clones for E008 activity
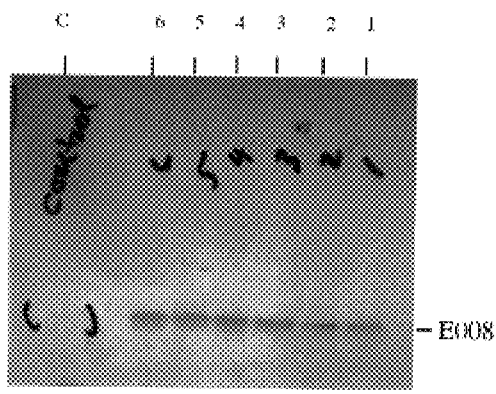
h) Screening positive lambda clones for E009 activity
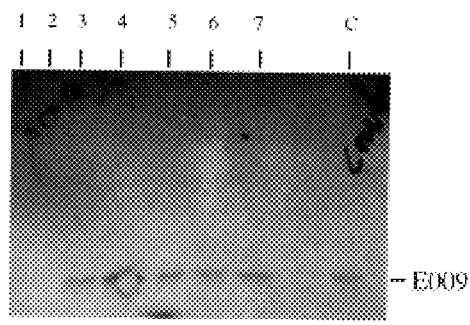

i) Screening positive lambda clones for E010 activity
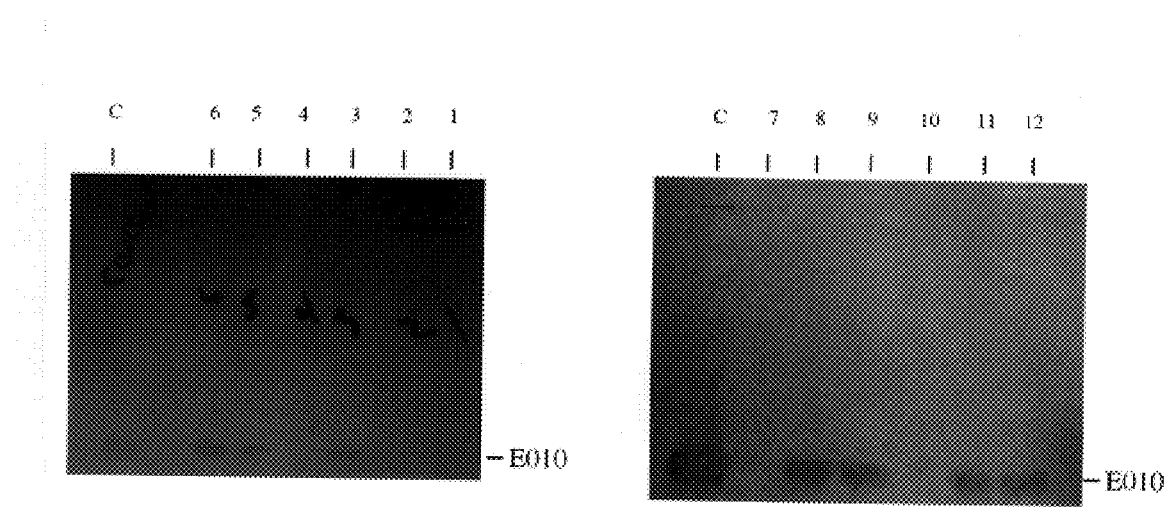
j) Screening positive lambda clones for E011 activity
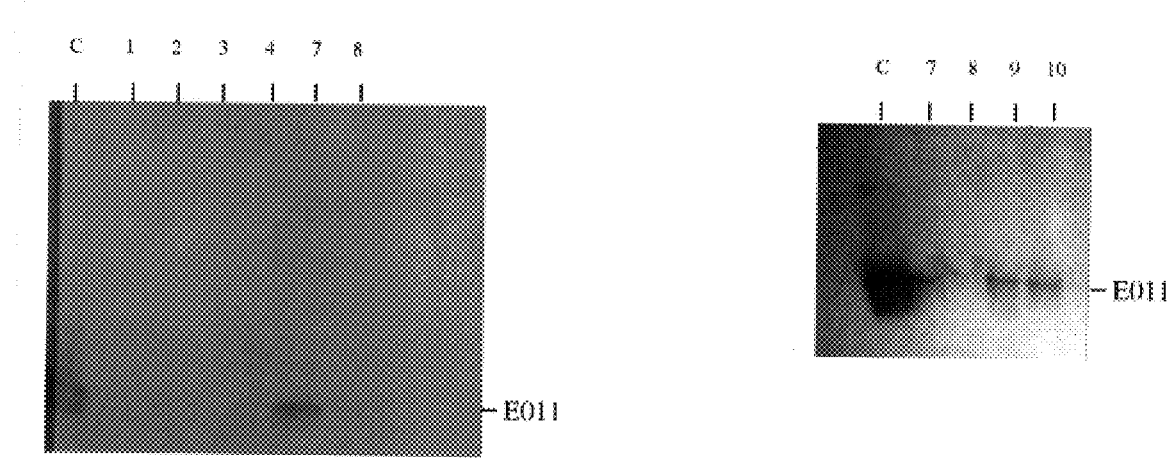

k) Screening positive lambda clones for E012 activity
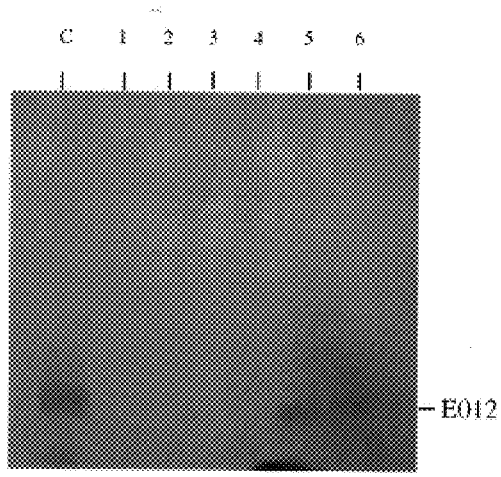
l) Screening positive lambda clones for E013 activity
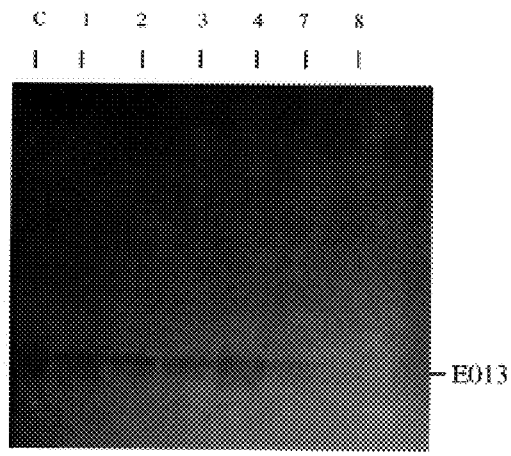
m) Screening positive lambda clones for E014 activity
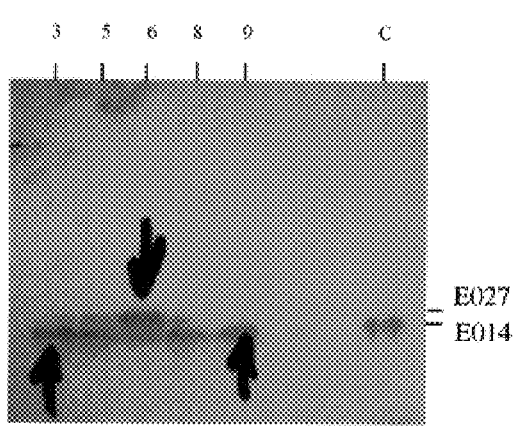
n) Screening positive lambda clones for E015 activity
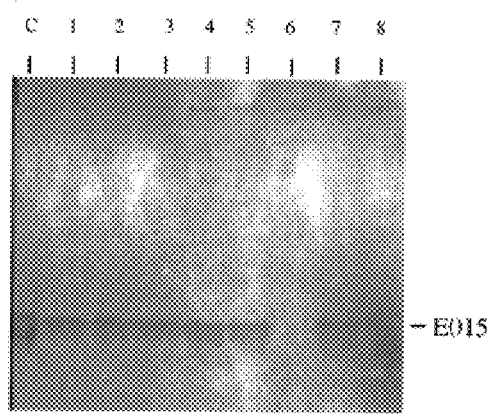

o) Screening positive lambda clones for E016 activity
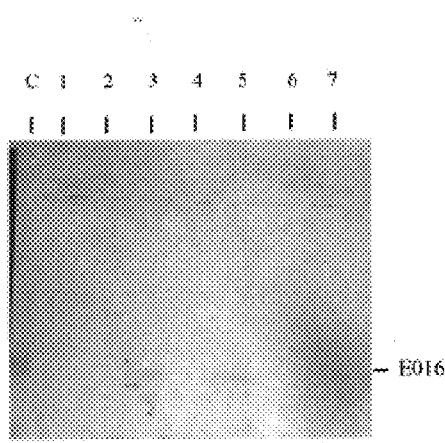
p) Screening positive lambda clones for E019 activity
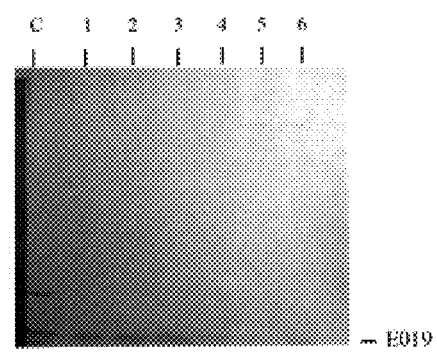
q) Screening positive lambda clones for E020 activity
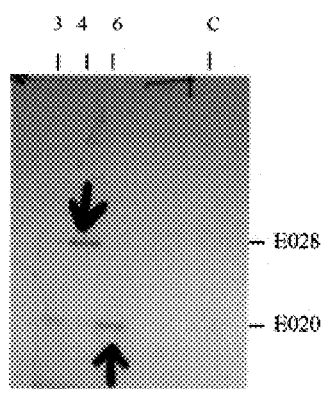
r) Screening positive lambda clones for E021 (E017b) activity
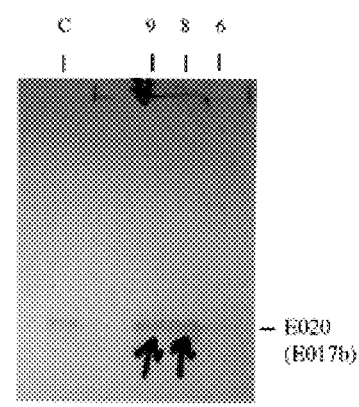

FIGURE 13
a) 28°C
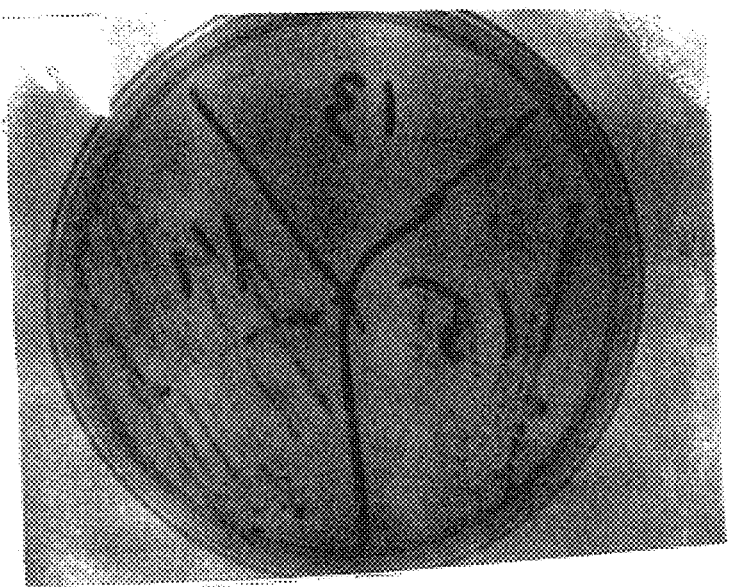
b) 37°C
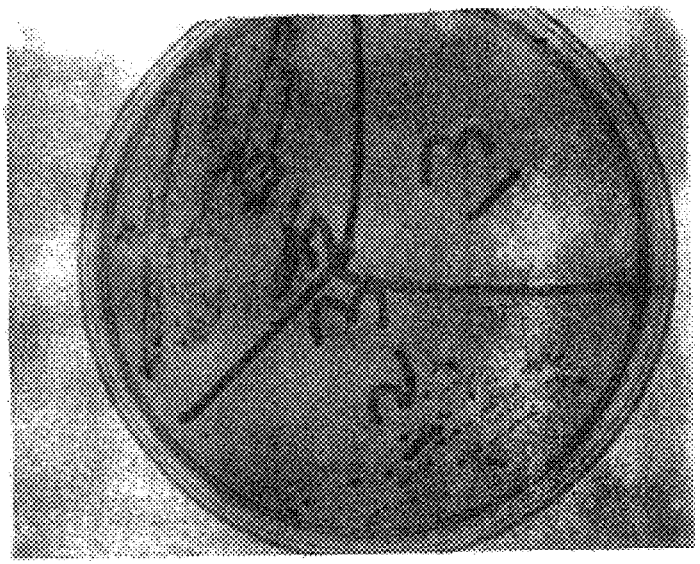

FIGURE 13
c) 28°C
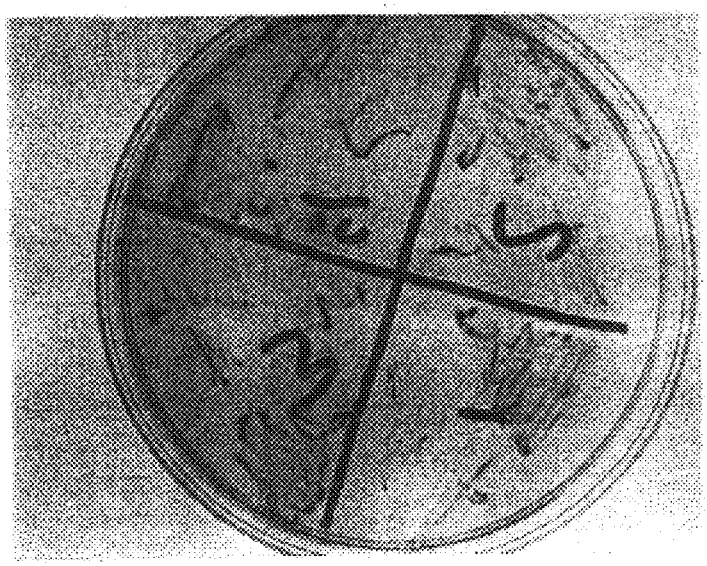
d) 37°C
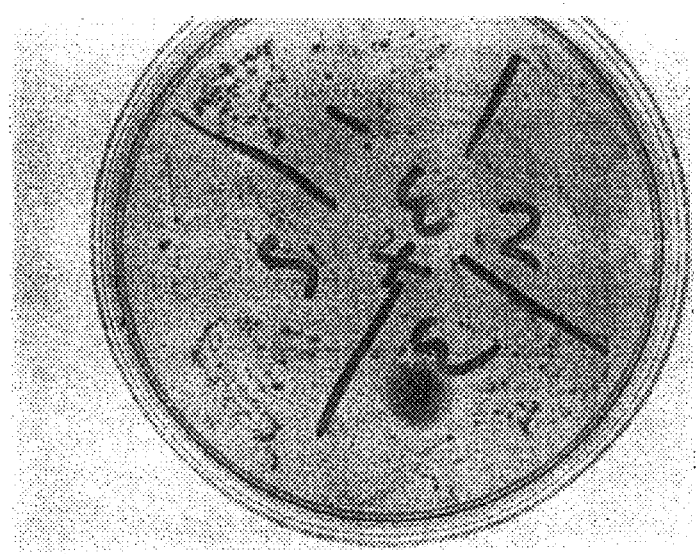

FIGURE 14
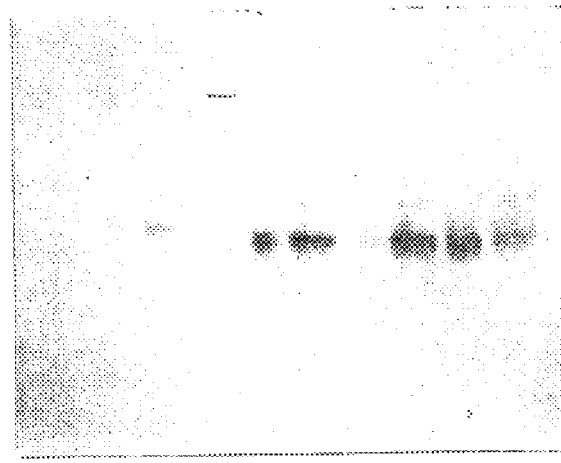
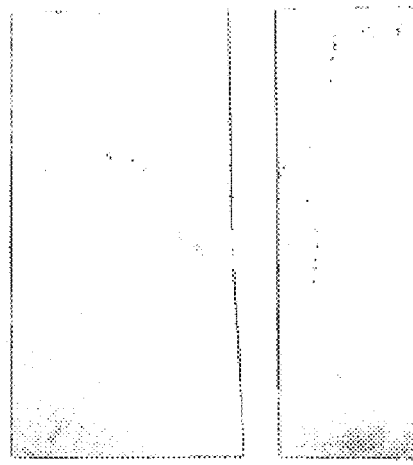
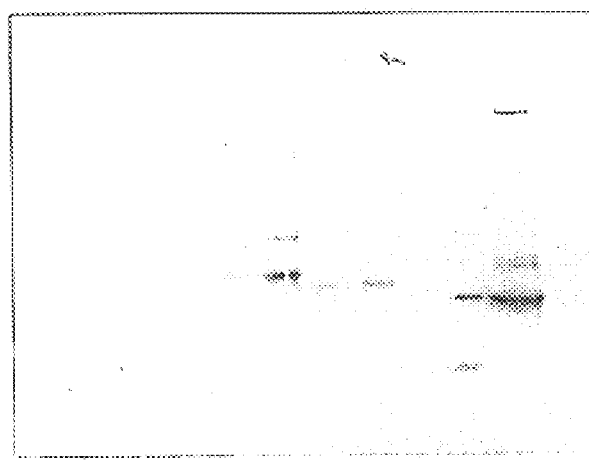
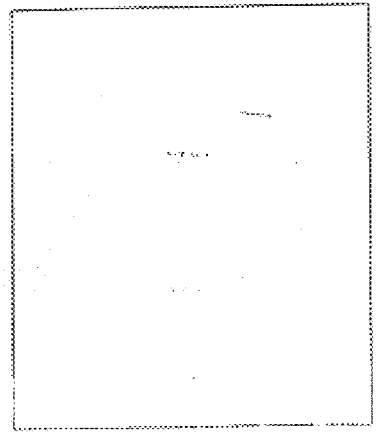

EcoRI, BamHI, HindIII, and EcoRV digestions

PstI 1-18

PstI and SbaI digestions

XbaI digestions

```
   1 TTGAAAAAGG GGATGGGAAC CGTGATCGTG GAAACAAAGT ACGGTCGGTT GCGCGGGGGA ACAAATGAAG
  1▶LeuLysLysG lyMetGlyTh rValIleVal GluThrLysT yrGlyArgLe uArgGlyGly ThrAsnGluG
  71 GGGTTTTCTA TTGGAAAGGG ATTCCGTACG CGAAAGCGCC GGTCGGTGAA CGCCGTTTTT TGCCGCCGGA
 24▶lyValPheTy rTrpLysGly IleProTyrA laLysAlaPr oValGlyGlu ArgArgPheL euProProGl
 141 ACCGCCCGAT GCATGGGACG GAGTGCGTGA GGCGACATCG TTTGGACCGG TCGTCATGCA GCCGTCCGAT
 47▶uProProAsp AlaTrpAspG lyValArgGl uAlaThrSer PheGlyProV alValMetGl nProSerAsp
 211 TCGATGTTCA GCCAGCTGCT CGGACGGATG AATGAACCAA TGAGCGAGGA TGGGTTGTAT CTGAACATTT
 71▶SerMetPheS erGlnLeuLe uGlyArgMet AsnGluProM etSerGluAs pGlyLeuTyr LeuAsnIleT
 281 GGTCACCGGC GGCGGATGGG AAGAAGCGCC CGGTATTGTT TTGGATTCAT GGCGGCGCTT TTTTATTCGG
 94▶rpSerProAl aAlaAspGly LysLysArgP roValLeuPh eTrpIleHis GlyGlyAlaP heLeuPheGl
 351 CTCCGGTTCA TTTCCATGGT ATGATGGAAC GGCGTTTGCC AAACACGGCG ATGTCGTTGT CGTGACGATC
117▶ySerGlySer PheProTrpT yrAspGlyTh rAlaPheAla LysHisGlyA spValValVa lValThrIle
 421 AACTACCGGA TGAGCGTGTT TGGCTTTTTG TATTTGGGAG ATGCGTTTGG CGAAACGTAT GCCCAGGCGG
141▶AsnTyrArgM etSerValPh eGlyPheLeu TyrLeuGlyA spAlaPheGl yGluThrTyr AlaGlnAlaG
 491 GAAATCTTGG CATATTGGAT CAAGTGGCGG CGCTGCGCTG GGTGAAAGAG AACATTGAGG CGTTCGGCGG
164▶lyAsnLeuGl yIleLeuAsp GlnValAlaA laLeuArgTr pValLysGlu AsnIleGluA laPheGlyGl
 561 TGATCCGGAC AACATTACGA TTTTTGGCGA ATCAGCCGGA GCGGCAAGCG TTGGCGTGCT GTTGTCGCTT
187▶yAspProAsp AsnIleThrI lePheGlyGl uSerAlaGly AlaAlaSerV alGlyValLe uLeuSerLeu
 631 CCGGAAGCAA GCGGGCTGTT TCGACGCGCT ATATTGCAAA GCGGATCGGG TTCGCTTCTT CTTCGTTCTC
211▶ProGluAlaS erGlyLeuPh eArgArgAla IleLeuGlnS erGlySerGl ySerLeuLeu LeuArgSerP
 701 CGGAGACGGC GATGGCTCTG ACTGAACGCA TTTTAGAACG TGCCGGCATC CGTCCGGGTG ACCGCGATCG
234▶roGluThrAl aMetAlaLeu ThrGluArgI leLeuGluAr gAlaGlyIle ArgProGlyA spArgAspAr
 771 GCTGCTGTCG ATTCCAGCAG CAGAGCTATT GCAGGCGGCG ATGTCGCTCG GCCCAGGAAT CACGTACGGT
257▶gLeuLeuSer IleProAlaA laGluLeuLe uGlnAlaAla MetSerLeuG lyProGlyIl eThrTyrGly
 841 CCGGTGGTTG ACGGACATGT GTTGCGACGC CATCCGATCG AAGCGCTCCA CGACGGGGCA GCAAGTGATA
281▶ProValValA spGlyHisVa lLeuArgArg HisProIleG luAlaLeuHi sAspGlyAla AlaSerAspI
 911 TTCCAATCCT AATTGGCGTG ACGAAAGACG AATACAATTT GTTTTCATTG ACTGATCCGT CATTGACAAG
304▶leProIleLe uIleGlyVal ThrLysAspG luTyrAsnLe uPheSerLeu ThrAspProS erLeuThrAr
 981 ACTCGAAGAA AAAGAACTGC TTGACCGGAT GAACCGTGAG GTCGGGCCTA TTCCGGAGGA GGCGGTACGC
327▶gLeuGluGlu LysGluLeuL euAspArgMe tAsnArgGlu ValGlyProI leProGluGl uAlaValArg
1051 TATTACGCGG AAACAGCGGA TCGGTCGGCA CCCGCGTGGC AAACATGGCT GCGCATCATG ACGTACCTTG
351▶TyrTyrAlaG luThrAlaAs pArgSerAla ProAlaTrpG lnThrTrpLe uArgIleMet ThrTyrLeuV
1121 TTTTTGTCGA CGGAATGTTG CGAACGGCGG ATGCCCAAGC AGCGCAAGGG GCGAATGTGT ACATGTATCG
374▶alPheValAs pGlyMetLeu ArgThrAlaA spAlaGlnAl aAlaGlnGly AlaAsnValT yrMetTyrAr
1191 GTTTGATTAT GAAACGCCGG CGTTCGGTGG ACAACTGAAA GCGTGCCATA CGCTCGAGTT GCCGTTTGTG
397▶gPheAspTyr GluThrProA laPheGlyGl yGlnLeuLys AlaCysHisT hrLeuGluLe uProPheVal
1261 TTTCATAACC TCCATCAGCC TGGTGTCGAG AATTTCGTCG GCAACCGACC AGAGCGTGAG GCGATTGCCA
421▶PheHisAsnL euHisGlnPr oGlyValGlu AsnPheValG lyAsnArgPr oGluArgGlu AlaIleAlaS
1331 GCGAAATGCA TGGTGCCTGG CTTTCGTTCG CCCGCACCGG CAACCCGAAC GGCGCTCATT TACCAGAGAA
444▶erGluMetHi sGlyAlaTrp LeuSerPheA laArgThrGl yAsnProAsn GlyAlaHisL euProGluLy
1401 GTGGCCCGTA TACACAAAAG AGCACAAACC GGTGTTTGTC TTTTCGGCTG CGAGCCATGT GGAAGACGAT
467▶sTrpProVal TyrThrLysG luHisLysPr oValPheVal PheSerAlaA laSerHisVa lGluAspAsp
1471 CCGTTCGGTC GCGAGCGGGA AGCGTGGCAA GGACGCCTTT GA
491▶ProPheGlyA rgGluArgGl uAlaTrpGln GlyArgLeu• • •
```

E001 ORF,
<u>underlined</u> possible
start codons.

FIGURE 16A

```
   1 GATCAAGTGG CGATCGACCG CGCGTTGATT GAACTTGACG GCACGGAAAA CAAAGGAAAG CTTGGGGCGA
  71 ATGCTATTTT AGGCGTGTCG CTCGCGGTCG CTCGCGCTGC GGCTGATGAG CTTGGCTTGC CGTTGTACCA
 141 ATACTTGGGC GGCTTTAACG CTAAAACGCT GCCTGTACCG ATGATGAACA TTTTAAACGG CGGCGCGCAT
 211 GCGGACAACA ACGTTGACAT TCAAGAATTC ATGATCATGC CGGTCGGTGC GGAAAGCTTC CGTGAAGCGC
 281 TGCGCATGGG TGCAGAAATT TTCCATAGCT TAAAAGCTGT GTTAAAAGCG AAAGGCTACA ACACGGCTGT
 351 CGGTGACGAA GGCGGATTTG CTCCGAACTT AAAATCGAAC GAAGAAGCGC TGCAAACGAT CATTGAAGCG
 421 ATCGAAAAAG CCGGCTACAA ACCAGGCGAA CAAGTGATGC TCGCTATGGA CGTTGCTTCG TCGGAGCTGT
 491 ACAACAAAGA AGATGGCAAA TATCATTTGG AAGGCGAAGG CGTCGTCAAA ACATCAGAAA AAATGGTTGC
 561 TTGGTATGAA GAGCTTGTGT CGAAATATCC GATCATCTCG ATCGAAGACG GACTTGACGA AAATGACTGG
 631 GAAGGCCATA AACTGCTTAC TGAGCGCCTT GGCCACAAAG TGCAGCTCGT CGGTGACGAC TTGTTTGTAA
 701 CGAACACGAA AAAACTGGCC GAAGGCATTG AAAAAGCGT CGGCAACTCG ATTTTAATTA AAGTGAACCA
 771 AATCGGTACA CTGACGGAAA CGTTCGATGC CATTGAGATG GCCAAACGCG CCGGCTACAC GGCGGTTGTG
 841 TCGCACCGTT CCGGTGAAAC GGAAGACAGC ACGATTGCCG ATATCGCTGT CGCAACAAAC GCTGGCCAAA
 911 TCAAAACGGG AGCACCGTCG CGTACGGACC GCGTCGCAAA ATACAACCAG CTGCTCCGCA TTGAAGACGA
 981 ACTTGGCCAC ACGGCTATTT ACCAAGGCAT TCGTTCGTTT TACAATTTGA AAAAATAACG GAATCAACA
1051 ACAAAGGGTG TCTCCAACGT TGCGAGACAC CCTCTTTAAT TACGGGAAAC AGAAATGATT TCCTATCGAT
1121 AGCAAAAAAT GGACGTGGGT AAACCATTCG TTTATAATAT CTTTTTGTAA TCGTTAGAAT ATTGAAAAAG
                                                                    1▶ LeuLysLys
1191 GGGATGGGAA CCGTGATCGT GGAACAAAG TACGGTCGGT TGCGCGGGGG AACAAATGAA GGGGTTTTCT
  4▶ GlyMetGlyT hrValIleVa lGluThrLys TyrGlyArgL euArgGlyGl yThrAsnGlu GlyValPheT
1261 ATTGGAAAGG GATTCCGTAC GCGAAAGCGC CGGTCGGTGA ACGCCGTTTT TTGCCGCCGG AACCGCCCGA
 27▶ yrTrpLysGl yIleProTyr AlaLysAlaP roValGlyGl uArgArgPhe LeuProProG luProProAs
1331 TGCATGGGAC GGAGTGCGTG AGGCGACATC GTTTGGACCG GTCGTCATGC AGCCGTCCGA TTCGATGTTC
 50▶ pAlaTrpAsp GlyValArgG luAlaThrSe rPheGlyPro ValValMetG lnProSerAs pSerMetPhe
1401 AGCCAGCTGC TCGGACGGAT GAATGAACCA ATGAGCGAGG ATGGGTTGTA TCTGAACATT TGGTCACCGG
 74▶ SerGlnLeuL euGlyArgMe tAsnGluPro MetSerGluA spGlyLeuTy rLeuAsnIle TrpSerProA
1471 CGGCGGATGG GAAGAAGCGC CCGGTATTGT TTTGGATTCA TGGCGGCGCT TTTTTATTCG GCTCCGGTTC
 97▶ laAlaAspGl yLysLysArg ProValLeuP heTrpIleHi sGlyGlyAla PheLeuPheG lySerGlySe
1541 ATTTCCATGG TATGATGAA CGGCGTTTGC CAAACACGGC GATGTCGTTG TCGTGACGAT CAACTACCGG
120▶ rPheProTrp TyrAspGlyT hrAlaPheAl aLysHisGly AspValValV alValThrIl eAsnTyrArg
1611 ATGAGCGTGT TTGGCTTTTT GTATTTGGA GATGCGTTTG GCGAAACGTA TGCCCAGGCG GGAAATCTTG
144▶ MetSerValP heGlyPheLe uTyrLeuGly AspAlaPheG lyGluThrTy rAlaGlnAla GlyAsnLeuG
1681 GCATATTGGA TCAAGTGGCG GCGCTGCGCT GGGTGAAAGA GAACATTGAG GCGTTCGGCG GTGATCCGGA
167▶ lyIleLeuAs pGlnValAla AlaLeuArgT rpValLysGl uAsnIleGlu AlaPheGlyG lyAspProAs
1751 CAACATTACG ATTTTTGGCG AATCAGCCGG AGCGGCAAGC GTTGGCGTGC TGTTGTCGCT TCCGGAAGCA
190▶ pAsnIleThr IlePheGlyG luSerAlaGl yAlaAlaSer ValGlyValL euLeuSerLe uProGluAla
1821 AGCGGGCTGC TTCGACGGC TATATTGCAA AGCGGATCGG GTTCGCTTCT TCTTCGTTCT CCGGAGACGG
214▶ SerGlyLeuP heArgArgAl aIleLeuGln SerGlySerG lySerLeuLe uLeuArgSer ProGluThrA
1891 CGATGGCTCT GACTGAACGC ATTTTAGAAC GTGCCGGCAT CCGTCCGGGT GACCGCGATC GGCTGCTGTC
237▶ laMetAlaLe uThrGluArg IleLeuGluA rgAlaGlyIl eArgProGly AspArgAspA rgLeuLeuSe
1961 GATTCCAGCA GCAGAGCTAT TGCAGGCGGC GATGTCGCTC GGCCCAGGAA TCACGTACGG TCCGGTGGTT
260▶ rIleProAla AlaGluLeuL euGlnAlaAl aMetSerLeu GlyProGlyI leThrTyrGl yProValVal
2031 GACGGACATG TGTTGCGACG CCATCCGATC GAAGCGCTCC ACGACGGGGC AGCAAGTGAT ATTCCAATCC
284▶ AspGlyHisV alLeuArgAr gHisProIle GluAlaLeuH isAspGlyAl aAlaSerAsp IleProIleL
2101 TAATTGGCGT GACGAAAGAC GAATACAATT TGTTTTCATT GACTGATCCG TCATTGACAA GACTCGAAGA
307▶ euIleGlyVa lThrLysAsp GluTyrAsnL euPheSerLe uThrAspPro SerLeuThrA rgLeuGluGl
2171 AAAAGAACTG CTTGACCGGA TGAACCGTGA GGTCGGGCCT ATTCCGGAGG AGGCGGTACG CTATTACGCG
330▶ uLysGluLeu LeuAspArgM etAsnArgGl uValGlyPro IleProGluG luAlaValAr gTyrTyrAla
2241 GAAACAGCGG ATCGGTCGGC ACCCGCGTGG CAAACATGGC TGCGCATCAT GACGTACCTT GTTTTTGTCG
354▶ GluThrAlaA spArgSerAl aProAlaTrp GlnThrTrpL euArgIleMe tThrTyrLeu ValPheValA
2311 ACGGAATGTT GCGAACGGCG GATGCCCAAG CAGCGCAAGG GGCGAATGTG TACATGTATC GGTTTGATTA
377▶ spGlyMetLe uArgThrAla AspAlaGlnA laAlaGlnGl yAlaAsnVal TyrMetTyrA rgPheAspTy
2381 TGAAACGCCG GCGTTCGGTG GACAACTGAA AGCGTGCCAT ACGCTCGAGT TGCCGTTTGT GTTTCATAAC
400▶ rGluThrPro AlaPheGlyG lyGlnLeuLy sAlaCysHis ThrLeuGluL euProPheVa lPheHisAsn
2451 CTCCATCAGC CTGGTGTCGA GAATTTCGTC GGCAACCGAC CAGAGCGTGA GGCGGATTGC AGCGAAATGC
424▶ LeuHisGlnP roGlyValGl uAsnPheVal GlyAsnArgP roGluArgGl uAlaIleAla SerGluMetH
2521 ATGGTGCCTG GCTTTCGTTC GCCCGCACCG GCAACCCGAA CGGCGCTCAT TTACCAGAGA AGTGGCCCGT
447▶ isGlyAlaTr pLeuSerPhe AlaArgThrG lyAsnProAs nGlyAlaHis LeuProGluL ysTrpProVa
2591 ATACACAAAA GAGCACAAAC CGGTGTTTGT CTTTTCGGCT GCGAGCCATG TGGAAGACGA TCCGTTCGGT
470▶ lTyrThrLys GluHisLysP roValPheVa lPheSerAla AlaSerHisV alGluAspAs pProPheGly
2661 CGCGAGCGGG AAGCGTGGCA AGGACGCCTT TGACGAAAAA ATCCATAAGC AACATGTGTT CTTTGTCTGA
494▶ ArgGluArgG luAlaTrpGl nGlyArgLeu •••
2731 ACACGATCAA GGTACGCGCA TTTTCGCGGA AAAAGACCGT GGGCAAACGT TCGCCTTTAC CTCTAAAAGG
```

FIGURE 16B

```
2801  AATGACGCAA CATGTCTGCA CTTCACAGGA AAGAGGACGA AACGGTTGGT TTTCAGAATA GGAAAAGGTG
2871  TCCCGTTTTT TGGGACACCT TCTTCTATGT ATCGCTCAAT CATTTGCTTC TGTGGCAGGA AGCCCGAATC
2941  GCTCGGCGAG TGCCGGATCA CGATCGATCG CCTCAATCAG TTTCCGCATG ACGTTCACAT CAAACGTAAA
3011  ATTCGAACCG ATTGGCGAGG TGACGAAAAT TTTCCCTTCT TTCGCCTCGC GTGCTCGTTT AAATTGATAG
3081  CCGTCAATCG CAATGACGAC TCGTTCGTCT GGCCTTGCCA TTAGGAATCC CTCCATCGCT GTTTTTTCTT
3151  TCATTGTACT TGATTTTGAG GATGAACACC AACGTTCATG ACACGCTCTT AAGGATAACG GATGGGAGAG
3221  CGTTAGAGGG CGGTGAATTT CATCAAGAAC GTAGCACAAA ACGACATTTT TTCATTATAG ACGTCTTGAT
3291  GTTTGGAATG ATCGGAAAAG GCGATTGTTA GGCGGGGATC ATGATCCACT AGCGGATGAA AGTGAAGAGC
3361  AACGAAATAG TCTCTTTGTT TCACAACAAA TGAATTGGTG CCATTCAGGG CGGAGACAGG TGAGACAGTT
3431  GCTGCAAACG ATAATGTATG GTATAGTAAA AATATTGCAA CGTAGGTCGT TGGAGGTGTC AGGCATGCAT
3501  GCCTTGCTTG TGACGTTGCT TGTCATTGTA TCGATTGCGC TGATTGCGAT TGTGTTGTTG CAGTCAGGCC
3571  GAAGCGCAGG GCTGTCGGGG GCGATTACCG GCGGTGCCGA GCAGCTGTTT GGCAAACAGA AAGCGCGCGG
3641  GCTTGATGCA GTGTTTCAGC GCGTGACGGT CGTGTTGGCC ATTTGTTTT TTGTGTTGAC GATTCTCGTC
3711  GCATATGTCC AACCATCATA AGCGAAAAGC GGGGGGCGGT CCTAACAAAA ACGGGCTGCC TTTTCTATTT
3781  CATCTAGAGA GGAAGGAGAA CGATGATGAA AATTGTTCCG CCAAAACCGT TTTTCTTTGA AGCCGGGGAG
3851  CGTGCCGTTT TGCTTTTGCA CGGATTTACC GGAAACTCCG CTGATGTTCG GATGCTCGGA CGCTTTCTCG
3921  AATCAAAAGG CTACACGTGC CATGCGCCGA TTTACAAAGG GCATGGCGTG CCGCCGGAAG AGCTCGTCCA
3991  TACCGGTCCG GACGATTGGT GGCAAGATGT GATGAACGGT TATCAGTTTT TGAAAAACAA AGGATATGAA
4061  AAAATCGCGG TTGCTGGGTT GTCGCTTGGA GGCGTATTTT CCTTAAAATT AGGTTACACT GTACCTATAG
4131  AAGGAATTGT GACCATGTGC GCACCGATGT ACATCAAAAG CGAAGAAACG ATGTATGAAG GTGTGCTTGA
4201  GTATGCGCGC GAATATAAAA AACGGGAAGG AAAATCGGCA GAACAAATCG AACAGGAAAT GGAACGGTTC
4271  AAACAAACGC CGATGAAAAC ATTAAAAGCG CTGCAAGCGT TGATC
```

E001 sequence
with ORF

FIGURE 16B

```
   1 TTGATTCAAA TGAATACGTT GGTGGAAACC CGTTTTGGGA AAGTGCAAGG CGGTACAGAC GGAGAGGTTT
  1▶ LeuIleGlnM etAsnThrLe uValGluThr ArgPheGlyL ysValGlnGl yGlyThrAsp GlyGluValC
  71 GTTTTTGGAA AGGGATTCCT TATGCGAAAC CTCCGGTGGG AAAAACGCCG CTTTCAAAAAC CGGAACCGCC
  24▶ ysPheTrpLy sGlyIlePro TyrAlaLysP roProValGl yLysArgArg PheGlnLysP roGluProPr
 141 GGAGAAATGG GATGGCGTTT GGGAGGCCAC CCGGTTCCGG TCCATGGTGA TGCAGCCGTC CGGCACCACC
  47▶ oGluLysTrp AspGlyValT rpGluAlaTh rArgPheArg SerMetValM etGlnProSe rGlyThrThr
 211 TTCAGCACCG TGCTCGGGGA AGCGGATCTT CCTGTGAGCG AAGACGGTCT TTATCTGAAT ATCTGGTCGC
  71▶ PheSerThrV alLeuGlyGl uAlaAspLeu ProValSerG luAspGlyLe uTyrLeuAsn IleTrpSerP
 281 CGGCAGCCGA CGGAAAAAAG CGGCCGGTGC TCTTCTGGAT CCATGGCGGC GCCTACCAGT TTGGGTCCGG
  94▶ roAlaAlaAs pGlyLysLys ArgProValL euPheTrpIl eHisGlyGly AlaTyrGlnP heGlySerGl
 351 CGCTTCCCCC TGGTATGACG GGACGGAGTT TGCCAAAAAC GGAGATGTGG TGGTTGTCAC GATCAACTAC
 117▶ yAlaSerPro TrpTyrAspG lyThrGluPh eAlaLysAsn GlyAspValV alValValTh rIleAsnTyr
 421 CGGTTGAACG CGTTTGGATT TTTGTACTTG GCAGATTGGT TCGGCGACGA ATTTTCAGCG TCGGGCAACC
 141▶ ArgLeuAsnA laPheGlyPh eLeuTyrLeu AlaAspTrpP heGlyAspGl uPheSerAla SerGlyAsnL
 491 TGGGAATTTT GGACCAAGTC GCTGCACTGC GCTGGGTGAA AGAAAACATT TCGGCATTCG GCGGCGACCC
 164▶ euGlyIleLe uAspGlnVal AlaAlaLeuA rgTrpValLy sGluAsnIle SerAlaPheG lyGlyAspPr
 561 GGAGCAAATC ACCATCTTCG GGGAGTCGGC CGGAGCCGGA AGCGTCGGGG TTCTGCTTTC CCTCCCGGAA
 187▶ oGluGlnIle ThrIlePheG lyGluSerAl aGlyAlaGly SerValGlyV alLeuLeuSe rLeuProGlu
 631 ACCAAAGGGC TGTTTCAACG GGCGATCTTG CAAAGCGGAT CGGGTGCCAT TTTGCTCCGT TCCTCTCAGA
 211▶ ThrLysGlyL euPheGlnAr gAlaIleLeu GlnSerGlyS erGlyAlaIl eLeuLeuArg SerSerGlnT
 701 CAGCCTCGGG CATCGCGGAA CAAATTCTTA CGAAAGCCGG CATTCGAAAA GGAGACCGCG ACCGGTTGTT
 234▶ hrAlaSerGl yIleAlaGlu GlnIleLeuT hrLysAlaGl yIleArgLys GlyAspArgA spArgLeuLe
 771 ATCCATCCCG GCCGGTGAAC TCCTTGAAGC CGCACAATCC GTGAATCCGG AATGGTTTT TGGTCCCGTT
 257▶ uSerIlePro AlaGlyGluL euLeuGluAl aAlaGlnSer ValAsnProG lyMetValPh eGlyProVal
 841 GTGGACGGCA CCGTATTGAA AACCCATCCG ATTGAAGCGT GGAAACCGG AGCCGCCGGC GATATCCCGA
 281▶ ValAspGlyT hrValLeuLy sThrHisPro IleGluAlaL euGluThrGl yAlaAlaGly AspIleProI
 911 TCATCATCGG GGTGACAAAG GATGAGTACA ATTTATTTAC ACTGACTGAC CCTTCCTGGA CGACAGCGGG
 304▶ leIleIleGl yValThrLys AspGluTyrA snLeuPheTh rLeuThrAsp ProSerTrpT hrThrAlaGl
 981 AAAAGAAGAA CTGATGGACC GGATCGAACA GGAAATCGGG CCGGTTCCGG AAAAAGTTTT TCCATATTAC
 327▶ yLysGluGlu LeuMetAspA rgIleGluGl nGluIleGly ProValProG luLysValPh eProTyrTyr
1051 TTATCTTTTG GGGATCCATC GCAACCGGTA TGGCAAAAGC TGTTGCGCGC CATGACCTAC CACATCTTTA
 351▶ LeuSerPheG lyAspProSe rGlnProVal TrpGlnLysL euLeuArgAl aMetThrTyr HisIlePheT
1121 CCCCGGGGCAT GTTAAAAACG GCTGACGCCC AAATCAAGCA AGGCGGGAAG GTTTGGGTTT ACCGGTTTGA
 374▶ hrArgGlyMe tLeuLysThr AlaAspAlaG lnIleLysGl nGlyGlyLys ValTrpValT yrArgPheAs
1191 TTACGAAACC CCGCTCTTTG ACGGTCGGTT GAAAGCATGT CACGCACTGG AAATCCCCTT TGTCTTTCAC
 397▶ pTyrGluThr ProLeuPheA spGlyArgLe uLysAlaCys HisAlaLeuG luIleProPh eValPheHis
1261 AACCTGCATC AACCGGGGGT CGATGTGTTC ACCGGCACAC ATCCGAAGCG GGAGCTAATT TCCCGGCAAA
 421▶ AsnLeuHisG lnProGlyVa lAspValPhe ThrGlyThrH isProLysAr gGluLeuIle SerArgGlnM
1331 TGCATGAAGC ATGGATTGCC TTTGCCCGGA CAGGGGATCC GAACGGCGAC CATCTCCCCG ATGCGTGGTT
 444▶ etHisGluAl aTrpIleAla PheAlaArgT hrGlyAspPr oAsnGlyAsp HisLeuProA spAlaTrpLe
1401 GCCCTTTGCA CAAAAAGACC GGCCGGCCAT GGTCTTTGAC ACCGAAACCA GAGCGGAAAA GCATCTGTTT
 467▶ uProPheAla GlnLysAspA rgProAlaMe tValPheAsp ThrGluThrA rgAlaGluLy sHisLeuPhe
1471 GACCGCGAGC AGGAACTGTG GGAATCAAAG GCTTGA
 491▶ AspArgGluG lnGluLeuTr pGluSerLys Ala•••
```

E009 ORF,
<u>underlined</u> possible start codons.

FIGURE 16C

```
   1 GATCCAAAAA CGAAAAAAGG CTTTTGTGGA TGAATTTGTC GTCCCTTTGG TGCAAGAAGC CCACAAACTG
  71 GGGATTACGG AAAGTGAAGT GTTTGCGCTG ATCAAAAAAG AAAGGAAAGG GATTGAGGAT GAATTATAAA
 141 GTGGAATTCG ACAATGTATC GTTGCGATAC AAAGACTTTG AGGCGCTCAA AAATGTTTCC TTCCAACTGG
 211 AAAGCGGAAA GATTTACGGT TTGCTCGGCC GGAACGGAGC CGGAAAGACC TCCCTCCTTT CTCTCTTGTC
 281 ATCTTTTCGC CTGCCGACGG AAGGATCAAT CTTGATCAGC GGGGAACCGC CGTTTGAAAA CCCGAAGATC
 351 ATGCCTCATG TTGTGTTGGT TTACGAAAAA GATTACAAGG AAGAGCGGAA TAAAGTCTCC ACCTTCATTC
 421 AGGATGCAGC CAAGTTCCGC CCGTTCTTTG ACATGAATTA TGCACTTCGG CTGGCTGAGA AATTCAAGCT
 491 TCCTTTAAAC AAAGAAGTGA GAAAACTGTC AAGAGGAATG AAGTCGGCGA TGAATGTGAC CATCGGACTG
 561 GCCAGCCGGG CGCCCGTGAC CATTTTTGAC GAGGCTTATC TTGGCATGGA TGCTCCGACC CGGGAAATGT
 631 TTTATAAAGA ATTGTTGAGA GACCAAGCCA AACATCCCCG GACCATGATT TTATCCACCC ACTTGGTGTC
 701 TGAAATGGAT TATTTGTTTG AAGAAGTGCT GATTCTCGAT CGCGGAAAGC TGTTGCTCCA TGAAGACTAT
 771 GAAACCTTGA TTTCCAAGGG ACTCATCATC ACAGGAGATG CCGGGGCGGT TGATGATTTC ACCAAAGGTC
 841 GGAAGATCCT GAACGAAGAG CAGCTCGGAA ATACAAAATC GGTAATTGTG TTCGGGGATT TCAATGAAGA
 911 TCTCCGGTTG GAAGCCGAAG AACAAGGATT GGAAACCGGG ACCTGCTCTT TGCAAGATCT GTTTATTCAT
 981 TTAACAGGCA AGGAGGATGC ATATGAAACC AACAGCCGTA TTTCCTAAAG TGGCCAAAGA CATGTACTTG
1051 GAACAAATGA AATGGACGGT TTGGTTTCTG GTTTTTGTGT TGGTTACCCA AATCGTACAT CTTTATTCCA
1121 GTTATTTTAC AATCGATGAT AACACCGCGG TGAAAGGGAT TTTGGTGCAT CTTTTTCCAT CGGCAAAGGT
1191 TTATATGATC GTGATCGCAA TTATTTCCGT CAACGGATTC CTGTCTTATT ATGTCGGGCA GGGAGTCACC
1261 CGGAGAGATT TTTGGGCCGG CTCGATGCTT GCCGCGCTCG GGCTGACGGC CACGATCACT TTCTCCGCTG
1331 TGATTCTCAC TTATTTGGAA TACGGGATTT TGGAGATGTT CCAGCTATCT CATTTGCTGT CTGACGAATT
1401 TTTGAACGGA AACGGGTGGC TGGTGATTCA ATATCTGCTT AATATCTTTT TCTATTACTT GGCAGGTTAC
1471 CTGATCGGAG TCGGTTTTTA CCGGTTCCAC TGGATCGTCG GAATCGGATT TGTTGCCTTT TTCCTTCTTT
1541 CTGTTTCAGC GCTGGAATGG AGCGAAAAAT ATTCGCTCGG GCTGAATATA TTGAGTTCTG CGGCGGCCAT
1611 TGTCCTCTTT CTCACCTTAT TGCGCCAGTT AACAAAGAAT ATCGCCGTGA AGTTGTAAAT GGATCCGGGA
1681 GACTCAGGTC CGCATGTTGC CTGAGTCTCT TTGCCTTTTC ATGGCGTCTG GGATTCATCC CTTTTTTGCT
1751 TTGCCAAGCG TTTTTTTTGA ATCCAGACCA GCAATTTAAG GATCAGGAAC AACAGAAAGA TGGCTCCTGA
1821 TACAAGAATA ATGGCTCCTG ATATGATGGA CACAACCTTC CAAAAACCAA AAAAGTTCGC GGCCCGCAAA
1891 ATGATGAGCA GGATGGCAAA AGGAATGAGA AAGCCGATGA CATCCTTCCC TTTCACTAAC CCCTCTTCCT
1961 CCTTTTTTGT TGGAATATCG TTCAGGTTAA CGGGCTTGTC CCTCAGTGTC AATAAGGTGT AAGTGACAAC
2031 ATCCCAAACA AAATTCAGTG CGAAAAAACA AAGCGGGACG GATTGGCCGG AGGTTGATCA AAAGGGCACC
2101 CCCTCTAATT CACGCTGGAT CTTTCCTTTG TGTTTTAAAA CTTAAAGCAC CGGATTGCCG GCTGTATGGT
2171 CCGGTTGGAT ATTGTCATCA CATCGTGGAT ATCAGTGGAT CCGGTGCGAT GGATTGCTTC AGGGGAACTT
2241 TTAAACACTT GAGTTTGACA ACCACTCCTT AATCATTTAA GATTTAAATG AAAATTAAAA TAAATCAAAA
2311 AGATTGATTC AAATGAATAC GTTGGTGGAA ACCCGTTTTG GAAAGTGCA AGGCGGTACA GACGGAGAGG
           1▶LeuIleG InMetAsnTh rLeuValGlu ThrArgPheG lyLysValGl nGlyGlyThr AspGlyGluV
2381 TTTGTTTTTG GAAAGGGATT CCTTATGCGA AACCTCCGGT GGGAAAACGC CGCTTTCAAA AACCGGAACC
          23▶alCysPheTr pLysGlyIle ProTyrAlaL ysProProVa lGlyLysArg ArgPheGlnL ysProGluPr
2451 GCCGGAGAAA TGGGATGGCG TTTGGGAGGC CACCCGGTTC CGGTCCATGG TGATGCAGCC GTCCGGCACC
          46▶oProGluLys TrpAspGlyV alTrpGluAl aThrArgPhe ArgSerMetV alMetGlnPr oSerGlyThr
2521 ACCTTCAGCA CCGTGCTCGG GAAGCGGAT CTTCCTGTGA GCGAAGACGG TCTTTATCTG AATATCTGGT
          70▶ThrPheSerT hrValLeuGl yGluAlaAsp LeuProValS erGluAspGl yLeuTyrLeu AsnIleTrpS
2591 CGCCGGCAGC CGACGGAAAA AAGCGGCCGG TGCTCTTCTG GATCCATGGC GGCGCCTACC AGTTTGGGTC
          93▶erProAlaAl aAspGlyLys LysArgProV alLeuPheTr pIleHisGly GlyAlaTyrG lnPheGlySe
2661 CGGCGCTTCC CCCTGGTATG ACGGGACGGA GTTTGCCAAA AACGGAGATG TGGTGGTTGT CACGATCAAC
         116▶rGlyAlaSer ProTrpTyrA spGlyThrGl uPheAlaLys AsnGlyAspV alValValVa lThrIleAsn
2731 TACCGGTTGA ACGCGTTTGG ATTTTTGTAC TTGGCAGATT GGTTCGGCGA CGAATTTTCA GCGTCGGGCA
         140▶TyrArgLeuA snAlaPheGl yPheLeuTyr LeuAlaAspT rpPheGlyAs pGluPheSer AlaSerGlyA
2801 ACCTGGGAAT TTTGGACCAA GTCGCTGCAC TGCGCTGGGT GAAAGAAAAC ATTTCGGCAT TCGGCGGCGA
         163▶snLeuGlyIl eLeuAspGln ValAlaAlaL euArgTrpVa lLysGluAsn IleSerAlaP heGlyGlyAs
2871 CCCCGGAGCAA ATCACCATCT TCGGGGAGTC GGCCGGACCG GGAAGCGTCG GGGTTCTGCT TTCCCTCCCG
         186▶pProGluGln IleThrIleP heGlyGluSe rAlaGlyAla GlySerValG lyValLeuLe uSerLeuPro
2941 GAAACCAAAG GGCTGTTTCA ACGGGCGATC TTGCAAAGCG GATCGGGTGC CATTTTGCTC CGTTCCTCTC
         210▶GluThrLysG lyLeuPheGl nArgAlaIle LeuGlnSerG lySerGlyAl aIleLeuLeu ArgSerSerG
3011 AGACAGCCTC GGGCATCGCG GAACAAATTC TTACGAAAGC CGGCATTCGA AAAGGAGACC GCGACCGGTT
         233▶lnThrAlaSe rGlyIleAla GluGlnIleL euThrLysAl aGlyIleArg LysGlyAspA rgAspArgLe
3081 GTTATCCATC CCGGCCGGTG AACTCCTTGA AGCCGCACAA TCCGTGAATC CGGGAATGGT TTTTGGTCCC
         256▶uLeuSerIle ProAlaGlyG luLeuLeuGl uAlaAlaGln SerGlyMetV roGlyMetVa lPheGlyPro
3151 GTTGTGGACG GCACCGTATT GAAAACCCAT CCGATTGAAG CGTTGGAAAC CGGAGCCGCC GGCGATATCC
         280▶ValValAspG lyThrValLe uLysThrHis ProIleGluA laLeuGluTh rGlyAlaAla GlyAspIleP
3221 CGATCATCAT CGGGGTGACA AAGGATGAGT ACAATTTATT TACACTGACT GACCCTTCCT GGACGACAGC
         303▶roIleIleIl eGlyValThr LysAspGluT yrAsnLeuPh eThrLeuThr AspProSerT rpThrThrAl
3291 GGGAAAAGAA GAACTGATGG ACCGGATCGA ACAGGAAATC GGGCCGGTTC CGGAAAAAGT TTTTCCATAT
         326▶aGlyLysGlu GluLeuMetA spArgIleGl uGlnGluIle GlyProValP roGluLysVa lPheProTyr
3361 TACTTATCTT TTGGGGATCC ATCGCAACCG GTATGCAAA AGCTGTTGCG CGCCATGACC TACCACATCT
         350▶TyrLeuSerP heGlyAspPr oSerGlnPro ValTrpGlnL ysLeuLeuAr gAlaMetThr TyrHisIleP
3431 TTACCCGGGG CATGTTAAAA ACGGCTGACG CCCAAATCAA GCAAGGCGGG AAGGTTTGGG TTTACCGGTT
         373▶heThrArgG yMetLeuLys ThrAlaAspA laGlnIleLy sGlnGlyGly LysValTrpV alTyrArgPh
3501 TGATTACGAA ACCCCGCTCT TTGACGGTCG GTTGAAAGCA TGTCACGCAC TGGAAATCCC CTTTGTCTTT
         396▶eAspTyrGlu ThrProLeuP heAspGlyAr gLeuLysAla CysHisAlaL euGluIleP roPheValPhe
```

FIGURE 16D

```
3571 CACAACCTGC ATCAACCGGG GGTCGATGTG TTCACCGGCA CACATCCGAA GCGGGAGCTA ATTTCCCGGC
 420▶HisAsnLeuH isGlnProGl yValAspVal PheThrGlyT hrHisProLy sArgGluLeu IleSerArgG
3641 AAATGCATGA AGCATGGATT GCCTTTGCCC GGACAGGGGA TCCGAACGGC GACCATCTCC CCGATGCGTG
 443▶lnMetHisGl uAlaTrpIle AlaPheAlaA rgThrGlyAs pProAsnGly AspHisLeuP roAspAlaTr
3711 GTTGCCCTTT GCACAAAAAG ACCGGCCGGC CATGGTCTTT GACACCGAAA CCAGAGCGGA AAAGCATCTG
 466▶pLeuProPhe AlaGlnLysA spArgProAl aMetValPhe AspThrGluT hrArgAlaGl uLysHisLeu
3781 TTTGACCGCG AGCAGGAACT GTGGGAATCA AAGGCTTGAG TGATTTGCTC AAGCCTTTTT TGCATTTCAC
 490▶PheAspArgG luGlnGluLe uTrpGluSer LysAla•••
3851 GTATGTATTC GGATTTGGAA TTAAACAATG GTGCTTTTAT CGAAATGGGG AGTGTTTGCT TATAATGAAC
3921 GGGTTTACAA AGCTTGTTTT GGTACCGGAT TACTGAAATG ATCCGTGTTT ATCATTTGGA TGCTTTCTAT
3991 TGGAAACCGG GCTGGGTGGA GTCTTCCCCG GAGGAGTTCG TTGCAGCTCA GCAAGAAATT GTGAACCAAT
4061 GCCAATGGAT TGTGGAAGGG AATTACAGTA GAGAGAAATA AATAAGAACG CCGAAGAAAG GTCGAACCGT
4131 TATTATAAGA AACATGAGA TTTTGGGGAT TAGTTCCAGC GAATAAGTGG GGGGTATTAT GAAATGGAGA
4201 AAAAGCAAGG TACCTGCTGA TAAGCAATCA ATTGATCAGG TAAAAAATTT TGGGATTCAA TTTCCTTCCG
4271 ATTTCCGACA AATTGCAATT ACTTCTCATG GAACCCAACC AAGTCCTGAT ACGATTGACT TTGGAGTTCT
4341 AAAAAATCAT CTTCTTCAAA CCAAACAGAA AAACGAACCT CACGAATCGT TTTATTCAAA ATTTCTCACT
4411 CTGTTAAAGT GGGATGTCAG TAAACGTTAT AAAAATATCT TTTGATGATT GTATCATCAG CAATGAAAGA
4481 AAGACAAAAG AGGACTATGA GATATTTCTT TACAACAAAA GATGGATTAT CCTGAGGATA GTATATATAT
4551 TCCTAATCCT TTGAATATCA TCCGGATTGG ATAGAGGGGT CGTTATGCAA TGGTATCATC ATGTTAGTGA
4621 AGATGCAAAG GCGGCTTTTT ATTTATCTTT AACAGAAAAA GTATTGGATA AAATCAGTCA TTATGAATGG
4691 TTTCCTCATG TAAAAGAAAC CATGAACATG TGTTGGGATT GGATTGAGGA AAAAGGATGG AGTGGACATG
4761 ATCTTTATGA AAGGCTTGAT GATGAAGAAT CAGAAACAGG GTTATTTTCA ATTCACATGA ATGAAGTCGA
4831 TGCTGGTTTA GATGACGATG AAGATGAACT TGCTTTTTTC TGTGTAATTG ATGCAGTGGC CTACACGGTT
4901 TGGCAAGCCT GTAAGTATGA AGAGAAAGGC TATGTTCCGC AAGCAATTGA AGTTGTAAAT GATGAATTTA
4971 CAGACGGCGA ATTTATGAGA AAAATTTGCC AGATTCATGA TTACCAAGAA GAATGGATTG AGCGATTAAA
5041 ACAACACCTG ATAAAAAACC ACCCGGCAGG CAGTGACAAG AAGATCCAAA GAGAAGAATT GTTGAGCTTG
5111 ATTGCGTAAA AATTGGTTTC ATGGATTTCT TTGAAAGCCC GCCGGTCAAA AGGTGCGGGT TTTGTTTTTG
5181 TTAAAGGTGA AAGAAAAGTA ACGTGTTTCC ATAGGTTATC ATTGAATGAT TCGATTTCAT ATTTTGGGAG
5251 GTGATCAGAG CAATGAGCGA CTTTTTCTTTT TTGAAAAAAT ATGTCCTTCC ATCCGTAAAC GTTCAAGCAC
5321 CACCAGAGTA TAAACATGTA TTTTATCCGC TGGATATATG TGAAGTGGAA GAAGCGGAAC ATAGACTCAA
5391 TCGAACGTTT CCAAAAGAGT TAAGGGAATT TTATTTGCAA ATTGGATATG GCTTTATGTG TATTCATCAG
5461 AAGACTTTTG ATAACCGTAT CATGGATCCC GATTCCCTTG CAGATTTGAT CTTGGGTGAA GACATTTGGG
5531 AAGATTATGA TCTGATGGAA GAGATCGGAG AACCACATTT ATTCCCGTTT TTTTTCTTGG GTAATGATGA
5601 CTTGATTTTT TTCGATTTGA GTCAAGAGAC AAGAGAAGGA ATTCATCCGG TTGACTATGG AAGGGTGATC
5671 ATTGCGGAAT CCCTTGAAGA TTTTTTACGT AAGTTAGATG CTAAAGAAAA TTATTATATC AATGTTGTTG
5741 ATGATAAATC GGGTTTTTGA AAGATTTTCC CCCATTATAA AAAATATAGT GGCACCTGAT TGAACGATAG
5811 AATATCAAAT GCTGAAAAGT TGATTCCGAT TTTGCGGCCG ATATTATGGA ACAATGTAAC GAACTTGGGA
5881 GGCAATAGAG TGTGGAGTGG TACAAAAAGG TAAATATGGA TGCGAGAGCG GCTTATTTTT TAGCTTTATC
5951 TGAGAAAGTT TTAGATAAAT TAACTAAATT TGATTGGTTT CCGGCAATAA GAAAGTCCAT GGATTTGTGT
6021 TGGAAATGGA TCACGGCGAC GCAAATGCTG GATTCCATGC AACGCAATCC AAGGCCCACC CGGGCGGAAG
6091 CCAGCGACGT GGCCAATGCG ATTTTGGACG GAACTGATGC CATCATGTTG TCCGGGGAAA CGGCGGCCGG
6161 GAAATATCCG GTGGAATCCG TCAGTACCAT GGCGCGGATT GCCATTCGCA CGGAATCATC GCTTCGGTAT
6231 CAGGAACGTT TTCAACAAAA AATCAGAGAG ATC
```

E009 sequence
with ORF

FIGURE 16D

```
   1 GTGATTCAAA TGAATACGTT GGTGGAAACC CGTTTTGGGA AAGTGCAAGG CGGTACAGAC GGAGAGGTTT
   1▶ValIIeGlnM etAsnThrLe uValGluThr ArgPheGlyL ysValGlnGl yGlyThrAsp GlyGluValC
  71 GTTTTTGGAA AGGGATTCCT TATGCGAAAC CTCCGGTGG AAAACGCCGC TTTCAAAAAC CGGAACCGCC
  24▶ysPheTrpLy sGlyIIePro TyrAlaLysP roProValGl yLysArgArg PheGlnLysP roGluProPr
 141 GGAGAAATGG GATGGCGTTT GGGAGGCCAC CCGGTTCCGG TCCATGGTGA TGCAGCCGTC CGGCACCACC
  47▶oGluLysTrp AspGlyValT rpGluAlaTh rArgPheArg SerMetValM etGlnProSe rGlyThrThr
 211 TTCAGCACCG TGCTCGGGGA AGCGGATCTT CCTGTGAGCG AAGACGGTCT TTATCTGAAT ATCTGGTCGC
  71▶PheSerThrV alLeuGlyGl uAlaAspLeu ProValSerG luAspGlyLe uTyrLeuAsn IIeTrpSerP
 281 CGGCAGCCGA CGGAAAAAAG CGGCCGGTGC TCTTCTGGAT CCATGGCGGC GCCTACCAGT TTGGGTCCGG
  94▶roAlaAlaAs pGlyLysLys ArgProValL euPheTrpII eHisGlyGly AlaTyrGlnP heGlySerGl
 351 CGCTTCCCCC TGGTATGACG GGACGGAGTT TGCCAAAAAC GGAGATGTGG TGGTTGTCAC GATCAACTAC
 117▶yAlaSerPro TrpTyrAspG lyThrGluPh eAlaLysAsn GlyAspValV alValValTh rIIeAsnTyr
 421 CGGTTGAACG CGTTTGGATT TTTGTACTTG GCAGATTGGT TCGGCGACGA ATTTTCAGCG TCGGGCAACC
 141▶ArgLeuAsnA laPheGlyPh eLeuTyrLeu AlaAspTrpP heGlyAspGl uPheSerAla SerGlyAsnL
 491 TGGGAATTTT GGACCAAGTC GCTGCACTGC GCTGGGTGAA AGAAAACATT TCGGCATTCG GCGGCGACCC
 164▶euGlyIIeLe uAspGlnVal AlaAlaLeuA rgTrpValLy sGluAsnIIe SerAlaPheG lyGlyAspPr
 561 GGAGCAAATC ACCATCTTCG GGGAGTCGGC CGGAGCCGGA AGCGTCGGGG TTCTGCTTTC CCTCCCGGAA
 187▶oGluGlnIIe ThrIIePheG lyGluSerAl aGlyAlaGly SerValGlyV alLeuLeuSe rLeuProGlu
 631 ACCAAAGGGC TGTTTCAACG GGCGATCTTG CAAAGCGGAT CGGGTGCCAT TTTGCTCCGT TCCTCTCAGA
 211▶ThrLysGlyL euPheGlnAr gAlaIIeLeu GlnSerGlyS erGlyAlaII eLeuLeuArg SerSerGlnT
 701 CAGCCTCGGG CATCGCGGAA CAAATTCTTA CGAAAGCCGG CATTCGAAAA GGAGACCGCG ACCGGTTGTT
 234▶hrAlaSerGl yIIeAlaGlu GlnIIeLeuT hrLysAlaGl yIIeArgLys GlyAspArgA spArgLeuLe
 771 ATCCATCCCG GCCGGTGAAC TCCTTGAAGC CGCACAATCC GTGAATCCGG GAATGGTTTT TGGTCCCGTT
 257▶uSerIIePro AlaGlyGluL euLeuGluAl aAlaGlnSer ValAsnProG lyMetValPh eGlyProVal
 841 GTGGACGGCA CCGTATTGAA AACCCATCCG ATTGAAGCGT TGGAAACCGG AGCCGCCGGC GATATCCCGA
 281▶ValAspGlyT hrValLeuLy sThrHisPro IIeGluAlaL euGluThrGl yAlaAlaGly AspIIeProl
 911 TCATCATCGG GGTGACAAAG GATGAGTACA ATTTATTTAC ACTGACTGAC CCTTCCTGGA CGACAGCGGG
 304▶leIIeIIeGl yValThrLys AspGluTyrA snLeuPheTh rLeuThrAsp ProSerTrpT hrThrAlaGl
 981 AAAAGAAGAA CTGATGGACC GGATCGAACA GGAAATCGGG CCGGTTCCGG AAAAAGTTTT TCCATATTAC
 327▶yLysGluGlu LeuMetAspA rgIIeGluGl nGluIIeGly ProValProG luLysValPh eProTyrTyr
1051 TTATCTTTTG GGGATCCATC GCAACCGGTA TGGCAAAAGC TGTTGCGCGC CATGACCTAC CACATCTTTA
 351▶LeuSerPheG lyAspProSe rGlnProVal TrpGlnLysL euLeuArgAl aMetThrTyr HisIIePheT
1121 CCCGGGGCAT GTTAAAAACG GCTGACGCCC AAATCAAGCA AGGCGGGAAG GTTTGGGTTT ACCGGTTTGA
 374▶hrArgGlyMe tLeuLysThr AlaAspAlaG lnIIeLysGl nGlyGlyLys ValTrpValT yrArgPheAs
1191 TTACGAAACC CCGCTCTTTG ACGGTCGGTT GAAAGCATGT CACGCACTGG AAATCCCCTT TGTCTTTCAC
 397▶pTyrGluThr ProLeuPheA spGlyArgLe uLysAlaCys HisAlaLeuG luIIeProPh eValPheHis
1261 AACCTGCATC AACCGGGGGT CGATGTGTTC ACCGGCACA ATCCGAAGCG GGAGCTAATT TCCCGGCAAA
 421▶AsnLeuHisG lnProGlyVa lAspValPhe ThrGlyThrH isProLysAr gGluLeuIIe SerArgGlnM
1331 TGCATGAAGC ATGGATTGCC TTTGCCCGGA CAGGGGATCC GAACGGCGAC CATCTCCCCG ATGCGTGGTT
 444▶etHisGluAl aTrpIIeAla PheAlaArgT hrGlyAspPr oAsnGlyAsp HisLeuProA spAlaTrpLe
1401 GCCCTTTGCA CAAAAAGACC GGCCGGCCAT GGTCTTTGAC ACCGAAACCA GAGCGGAAAA GCATCTGTTT
 467▶uProPheAla GlnLysAspA rgProAlaMe tValPheAsp ThrGluThrA rgAlaGluLy sHisLeuPhe
1471 GACCGCGAGC AGGAACTGTG GGAATCAAAG GCTTGA
 491▶AspArgGluG lnGluLeuTr pGluSerLys Ala•••
```

E011 ORF,
<u>underlined</u> possible
start codons.

FIGURE 16E

```
   1 GATCCGCTTC ATCCAGCAGG TCCTGGAGCA GCGGGAGCGG GAGGACACCT TCCGCCTCAA GCGCATCAAG
  71 GGCAAGATCG AGGCCCGGGA AGCGGAGGAG GGGGGGCGGC CCAACCCCCA CCTGGAGATC GGAGCGGGCC
 141 TCTAAGGCCG CCCCAGCTTG AGCCACCCCC CAGGCTTCCC CTGGGGGGTT TACCCTTGAC CCGGTCCAAG
 211 GTTTTCGGGT AGGCTCCTCC TCGGAGGGAA AACCATGAGG CGGCTTTTGG GGCTCCTTTT GTTCCTGGCC
                                        1▶MetArg ArgLeuLeuG lyLeuLeuLe uPheLeuAla
 281 TTGGCCTTGG CGCAAGGCCT TGGCCCTTAC TGGCAGGAGG TTCAGGCCCA GGGTACGGTC TGCTCGGACG
  13▶LeuAlaLeuA laGlnGlyLe uGlyProTyr TrpGlnGluV alGlnAlaGl nGlyThrVal CysSerAspG
 351 GCTCCCCCTG GCGGTTCTAC GTGAGCCCGG GGGACCCCAA GAAGGTCCTT CTGGACTTCC AGGGGGGCGG
  36▶lySerProTr pArgPheTyr ValSerProG lyAspProLy sLysValLeu LeuAspPheG lnGlyGlyGl
 421 GGCCTGCTGG GACGCCCAGA CCTGCGGTCC CCAGAGCCAG ACCTACCGGA AGCGGGTGGA CGTGCAGGAA
  59▶yAlaCysTrp AspAlaGlnT hrCysGlyPr oGlnSerGln ThrTyrArgL ysArgValAs pValGlnGlu
 491 CTCCTCCTGG CCCAGGGGAT CTACAACCGG GCGAGCATCG CCAACCCCTT CTTCGGCTGG ACCCACGTCT
  83▶LeuLeuLeuA laGlnGlyIl eTyrAsnArg AlaSerIleA laAsnProPh ePheGlyTrp ThrHisValP
 561 TCATCCCCTA CTGCACGGGG GACCTGCACG TGGGCCGGGC CACGGTGGAC TACGGCGGCT TTAAGGTCCA
 106▶heIleProTy rCysThrGly AspLeuHisV alGlyArgAl aThrValAsp TyrGlyGlyP heLysValHi
 631 CCACCAGGGG GCGCGAAACG CCCTGGCCGC CTTGGAGTAC GTCTTCAAGA ACTACCCCAA GGCAGAGCGG
 129▶sHisGlnGly AlaArgAsnA laLeuAlaAl aLeuGluTyr ValPheLysA snTyrProLy sAlaGluArg
 701 GTCTTCGTCA CCGGGTGCAG CGCCGGGGGG TACGGGGCGG TCTTCTGGGC GGACAAGGTC CTTGCCACCT
 153▶ValPheValT hrGlyCysSe rAlaGlyGly TyrGlyAlaV alPheTrpAl aAspLysVal LeuAlaThrT
 771 ACAAAAGCGC CCAGATCGCC GTTTGCGGGG ACGCCGCCTT GGGCGTGAGC ACATCGGACT TCCCCGGGAG
 176▶yrLysSerAl aGlnIleAla ValCysGlyA spAlaAlaLe uGlyValSer ThrSerAspP heProGlySe
 841 CCGGGTTTGG AACGCCCGCC TGCCCGAGCT TCCCGGCCTG GGCCCGAACC CCAGCGTGGA GGAGATCTAC
 199▶rArgValTrp AsnAlaArgL euProGluLe uProGlyLeu GlyProAsnP roSerValGl uGluIleTyr
 911 CGGGCCCTGG CCCGGGCCTA CCCCGGCGCG GCCTTCGCCC AGTACACCAC CAGCTGGAC GGGACCCAGA
 223▶ArgAlaLeuA laArgAlaTy rProGlyAla AlaPheAlaG lnTyrThrTh rGlnLeuAsp GlyThrGlnI
 981 TCTACTTCTA CGCCCTCATG AAGAAGGAGG TACCCCCCTC CGAGGCCACC GCCCGGGAGT GGGCCGTCCG
 246▶leTyrPheTy rAlaLeuMet LysLysGluV alProProSe rGluAlaThr AlaArgGluT rpAlaValAr
1051 GGCCCAGACC AGCCTCCAGA GCCTGGCCCA GGAGTCCAAC TTCACCTACT ACCTGGCCCC GGGGAGCCAA
 269▶gAlaGlnThr SerLeuGlnS erLeuAlaGl nGluSerAsn PheThrTyrT yrLeuAlaPr oGlySerGln
1121 CACTGCATCC TGCCCCGGCC CGAGCTCTAC ACCCTGAAGG TGGGGGAGGT GAGCGTTCTG GACTGGCTCA
 293▶HisCysIleL euProArgPr oGluLeuTyr ThrLeuLysV alGlyGluVa lSerValLeu AspTrpLeuA
1191 GGAGCCTGGC GGAGAAGGGG CAGGCCCCCC GCGTAGGTCC GTGAGGTCGG GGAGGGCCTC GAGGAGGACC
 316▶rgSerLeuAl aGluLysGly GlnAlaProA rgValGlyPr o●●●
1261 CGGTACGCCT CCTTGGGGGA GGGGGCCTGG AGGAGGGCCC GGAGGACCCC CTCCCCTTTC GCCACCAGGA
1331 CGTCCGCCTT CAGGGCGAAG ACCCCTTGGA AGTAGAGGGC GTCCGCCAGG CTGGTGCGGA GCCGGTCATA
1401 GGCGCTGAGG CGGGGGTTGG GGGGTCTTAG CCGGGCGAGG AGGCGCGCCC AGGCCAGGTA AAGGGGGTAC
1471 CGCTCAGGGT AGGCCCCCTT CAGGGCGAAG AGGAAGAGGT AGTTGGCCAG GAACTCGTCC AGCCAGCGGC
1541 GGCCGGTCCT GAGCCGCCAG GCCACCTGGA CCGCGTGGCC GTGCTCGTGC CCAGGGTGA GGTCCAAGAA
1611 CTCCTCCAGC GCCCCGGGGA GACCCTCCTC CGCCACAGGC AGGAGGACCT GGCGCAGGCG GTGGAGGAGG
1681 CGCTCGGGGT AGACCAGAGG GACGAAGAGG TAAAGCCGGG TCCGGCTCGT CCTCTGGAAG GGGAGGCCGT
1751 AGGGCACCCG GTCCTCTCC CGCCAGTCCC TCTCCGAGAG GACGAAGAGG GTCACGGGGG GAAGGGGGCG
1821 GTAGCGGGCC AGGAGGCGGT GGAGCCCCTC CAGGTAGGCC TGGACCTGGG CGGTGCGGGC CTTTCCCCCC
1891 GGGCTGTAGA AGGCGGGGAG GTCGGGGTGG GGAGGGCGT TCATATCACC TCCCGGAACC CGATGCGCTC
1961 CGCCTGGGCC TGGAGCTCCC GCCGCAGGAG GGGGTGGGCC TCGAGGCGGG GGTCCTTCTC CAGGATCTCC
2031 TACAACGTGG ACTTCTAAAG CCCGCCGGGC CCTCCCCCCG CCCCCCGGGG CGGGGGGTTG GCCTTTTTCC
2101 GGCCCAGGCC AGGGAGCCTT GCGCGTTCGG CGTTTGGCGT TCAGCCTTCG GCGTTTGGCC CATAATCGGG
2171 ACCAGGCGAA ACGGGTATCA TGGAGGTATG CGCTGGCTGG GGGTGCTCCT CCTGGGCCTG GCCCTGGCCC
2241 AGGGGCTGGA CCTGGCCCGA TCCCTCCTGC GCCAGGGCCA GTACGAGCAG GCCCTGGCCC GGCTGGAGCG
2311 GGAGCCCCCC GGCTCCGGAG TCCTGGCCCT GAAGGGCCGG GCCTACCTGC TCCTGGGCCG GCCGGAGGCG
2381 GCCCGGGAGG CCCTGGAGGG GGCGGCCCGC CTGGGCCGGG GGGCGGAGGT GGAGCGGCTC AAGGGGTGGC
2451 TGGCCCTGGA GGCGGGAAAG GCCGAGGAGG CCCGCGGGGC CTTCCAGGCC GCGGCCATCT ACTCGGGCCT
2521 TCCCCAAGAC GCCCTCCTCT GGGCCCTGGC GGCTTGGGAG GCGGGCCGCT CTTCCGAGGA GGCCCTGGCC
2591 CGGGCGGAGC GGGCGGGAGG CGGGGCGGAG GCGGCCCTCC TTAAGGGGCT CTTCCTCCTG GCCCAGGACC
2661 CGGCGGAGGC CCTGGCCGCC TTCCGCCGGG CGGGGACGG CCCCTTCAAG GCCCAGGCCC TCTACCTGCA
2731 GGGCCTGGCC CTCGAGGCCC TGGCCGGGA CCCGGAGGCC CGGAGGCCT ACCGCCAGCC CCTGAAGGCC
2801 TCCCCGGACT ACCTCCCCGC CCGCCGGGCT TTAGGGCTCT AGTACCACCC CATCCTGGCG TACGCCAGGA
2871 TGGGGCCCCC GGTAAAGCCT TAGCCTTCCG ACGAAGCGGG GAATGAGGGG AAGCCTGAAT GACGGAAAAG
2941 AGGATGGAAA AATCGGTCTT CCGCTACCAA GGCCCCGAGC CAAGGGGGA CCAGCCCAAG GCCATCCGGG
3011 AGCTGGTGGA GGCCCTGGAG GCGGGGGAGC GGTTCGTCAC CCTTTTGGGG GCCACCGGCA CGGGGAAGAC
3081 GGTCACCATG GCCAAGGTGA TCGAGGCCCT GGGCAGGCCC ACCCTGGTCC TCGCCCCCAA CAAGATC
```

TspA E101
sequence with ORF

FIGURE 16F

```
3291 TAAATGAACA AGGAATCATC GATGTCATAC CCGTATTGCT GATATAACCG GATGGCCGGC TTGTTTTCGG
3361 CGATCGCTTC CAGTGTTGCC AGTTGCACAT GTTCCCGTTG ATACATCTCC ACCAATGCTT CCATCAGCCG
3431 GCTCCCAACC CCTTTTCGTC TCCATCCGGG AAGAACGGCT GTCCCTCCGT TCCAAGCGAC TTTTTTTCCT
3501 TTGATCTCCC CGATAGCCGT GAACACAAAA CCGACCGGCC GGCCATCGGC CCAAGCCACC AGGGAATGGG
3571 CCGGCGAAAT TTTTTCCCGG ACCATCCTGT TCATTAACCG GTCAAAAGTG AAATTCATGT TCACAAAGTA
3641 ATCCGCAAAG GCTTCGTTCC ACAATTGCAA CGTTTGTTCC CACGTGCACC TGCTCAATGG ATGAATCGTA
3711 ACCATGGCGC TTCCTTTCTT TTTGTTTGAT ATAATATCGG TGTAAAACGT TTGTGGGGAT TAAAACGCGG
3781 ATTCCTGAAG GACTTCCTCT TCTTCGGAAA TGCCTTGTTT TTTAAATTGC AACCGGCACC AAAAAGCCGA
3851 CTTGGCATAA TCCCAAAGAT ACCGGCTGAA TTCCCCGTTT GGATGTAAAT AGTTCCACAC CTCAGGGAAA
3921 TATTTCTTTA TATCAGATAA AATCTCCTTT TCCTTCTGAC TCATCACATG CAAGTTATGC CGGTATTTCA
3991 AACCCAGGGT TGTCAGGCAG TCCGTCACCT CCACCGGGAC TTTCCGCCAG ATTTGTTTCC ACTCTTCATA
4061 AGGTTCCATC AAATAATGAA CATTCAGATC
```

E011 sequence
with ORF

FIGURE 16F

```
  1 ATGAGGCGGC TTTTGGGGCT CCTTTTGTTC CTGGCCTTGG CCTTGGCGCA AGGCCTTGGC CCTTACTGGC
  1▶MetArgArgL euLeuGlyLe uLeuLeuPhe LeuAlaLeuA laLeuAlaGl nGlyLeuGly ProTyrTrpG
 71 AGGAGGTTCA GGCCCAGGGT ACGGTCTGCT CGGACGGCTC CCCCTGGCGG TTCTACGTGA GCCCGGGGGA
 24▶lnGluValGl nAlaGlnGly ThrValCysS erAspGlySe rProTrpArg PheTyrValS erProGlyAs
141 CCCCAAGAAG GTCCTTCTGG ACTTCCAGGG GGGCGGGGCC TGCTGGACG CCCAGACCTG CGGTCCCCAG
 47▶pProLysLys ValLeuLeuA spPheGlnGl yGlyGlyAla CysTrpAspA laGlnThrCy sGlyProGln
211 AGCCAGACCT ACCGGAAGCG GGTGGACGTG CAGGAACTCC TCCTGGCCCA GGGGATCTAC AACCGGGCGA
 71▶SerGlnThrT yrArgLysAr gValAspVal GlnGluLeuL euLeuAlaGl nGlyIleTyr AsnArgAlaS
281 GCATCGCCAA CCCCTTCTTC GGCTGGACCC ACGTCTTCAT CCCCTACTGC ACGGGGGACC TGCACGTGGG
 94▶erIleAlaAs nProPhePhe GlyTrpThrH isValPheIl eProTyrCys ThrGlyAspL euHisValGl
351 CCGGGCCACG GTGGACTACG GCGGCTTTAA GGTCCACCAC CAGGGGCGC GAAACGCCCT GGCCGCCTTG
117▶yArgAlaThr ValAspTyrG lyGlyPheLy sValHisHis GlnGlyAlaA rgAsnAlaLe uAlaAlaLeu
421 GAGTACGTCT TCAAGAACTA CCCCAAGGCA GAGCGGGTCT TCGTCACCGG GTGCAGCGCC GGGGGGTACG
141▶GluTyrValP heLysAsnTy rProLysAla GluArgValP heValThrGl yCysSerAla GlyGlyTyrG
491 GGGCGGTCTT CTGGGCGGAC AAGGTCCTTG CCACCTACAA AAGCGCCCAG ATCGCCGTTT GCGGGGACGC
164▶lyAlaValPh eTrpAlaAsp LysValLeuA laThrTyrLy sSerAlaGln IleAlaValC ysGlyAspAl
561 CGCCTTGGGC GTGAGCACAT CGGACTTCCC CGGGAGCCGG GTTTGGAACG CCCGCCTGCC CGAGCTTCCC
187▶aAlaLeuGly ValSerThrS erAspPhePr oGlySerArg ValTrpAsnA laArgLeuPr oGluLeuPro
631 GGCCTGGGCC CGAACCCCAG CGTGGAGGAG ATCTACCGG CCCTGGCCCG GGCCTACCCC GGCGCGGCCT
211▶GlyLeuGlyP roAsnProSe rValGluGlu IleTyrArgA laLeuAlaAr gAlaTyrPro GlyAlaAlaP
701 TCGCCCAGTA CACCACCCAG CTGGACGGGA CCCAGATCTA CTTCTACGCC CTCATGAAGA AGGAGGTACC
234▶heAlaGlnTy rThrThrGln LeuAspGlyT hrGlnIleTy rPheTyrAla LeuMetLysL ysGluValPr
771 CCCCTCCGAG GCCACCGCCC GGGAGTGGGC CGTCCGGGCC CAGACCAGCC TCCAGAGCCT GGCCCAGGAG
257▶oProSerGlu AlaThrAlaA rgGluTrpAl aValArgAla GlnThrSerL euGlnSerLe uAlaGlnGlu
841 TCCAACTTCA CCTACTACCT GGCCCCGGGG AGCCAACACT GCATCCTGCC CCGGCCCGAG CTCTACACCC
281▶SerAsnPheT hrTyrTyrLe uAlaProGly SerGlnHisC ysIleLeuPr oArgProGlu LeuTyrThrL
911 TGAAGGTGGG GGAGGTGAGC GTTCTGGACT GGCTCAGGAG CCTGGCGGAG AAGGGGCAGG CCCCCCGCGT
304▶euLysValGl yGluValSer ValLeuAspT rpLeuArgSe rLeuAlaGlu LysGlyGlnA laProArgVa
981 AGGTCCGTGA
327▶lGlyPro•••
```

**TspA E101 ORF,
<u>underlined</u> possible
start codons.**

FIGURE 16G

```
   1 GATCCGCTTC ATCCAGCAGG TCCTGGAGCA GCGGGAGCGG GAGGACACCT TCCGCCTCAA GCGCATCAAG
  71 GGCAAGATCG AGGCCCGGGA AGCGGAGGAG GGGGGGCGGC CCAACCCCCA CCTGGAGATC GGAGCGGGCC
 141 TCTAAGGCCG CCCCAGCTTG AGCCACCCCC CAGGCTTCCC CTGGGGGGTT TACCCTTGAC CCGGTCCAAG
 211 GTTTTCGGGT AGGCTCCTCC TCGGAGGGAA AACCATGAGG CGGCTTTTGG GGCTCCTTTT GTTCCTGGCC
                                              1▶MetArg ArgLeuLeuG lyLeuLeuLe uPheLeuAla
 281 TTGGCCTTGG CGCAAGGCCT TGGCCCTTAC TGGCAGGAGG TTCAGGCCCA GGGTACGGTC TGCTCGGACG
  13▶LeuAlaLeuA laGlnGlyLe uGlyProTyr TrpGlnGluV alGlnAlaGl nGlyThrVal CysSerAspG
 351 GCTCCCCCTG GCGGTTCTAC GTGAGCCCGG GGACCCCAA GAAGGTCCTT CTGGACTTCC AGGGGGGCGG
  36▶lySerProTr pArgPheTyr ValSerProG lyAspProLy sLysValLeu LeuAspPheG lnGlyGlyGl
 421 GGCCTGCTGG GACGCCCAGA CCTGCCGGTCC CCAGAGCCAG ACCTACCGGA AGCGGGTGGA CGTGCAGGAA
  59▶yAlaCysTrp AspAlaGlnT hrCysGlyPr oGlnSerGln ThrTyrArgL ysArgValAs pValGlnGlu
 491 CTCCTCCTGG CCCAGGGGAT CTACAACCGG GCGAGCATCG CCAACCCCTT CTTCGGCTGG ACCCACGTCT
  83▶LeuLeuLeuA laGlnGlyIl eTyrAsnArg AlaSerIleA laAsnProPh ePheGlyTrp ThrHisValP
 561 TCATCCCCTA CTGCACGGGG GACCTGCACG TGGGCCGGGC CACGGTGGAC TACGGCGGCT TTAAGGTCCA
 106▶heIleProTy rCysThrGly AspLeuHisV alGlyArgAl aThrValAsp TyrGlyGlyP heLysValHi
 631 CCACCAGGGG GCGCGAAACG CCCTGGCCGC CTTGGAGTAC GTCTTCAAGA ACTACCCAA GGCAGAGCGG
 129▶sHisGlnGly AlaArgAsnA laLeuAlaAl aLeuGluTyr ValPheLysA snTyrProLy sAlaGluArg
 701 GTCTTCGTCA CCGGGTGCAG CGCCGGGGG TACGGGCGG TCTTCTGGGC GGACAAGGTC CTTGCCACCT
 153▶ValPheValT hrGlyCysSe rAlaGlyGly TyrGlyAlaV alPheTrpAl aAspLysVal LeuAlaThrT
 771 ACAAAAGCGC CCAGATCGCC GTTTGCGGG ACGCCGGCTT GGGCGTGAGC ACATCGGACT TCCCCGGGAG
 176▶yrLysSerAl aGlnIleAla ValCysGlyA spAlaAlaLe uGlyValSer ThrSerAspP heProGlySe
 841 CCGGGTTTGG AACGCCCGCC TGCCCGAGCT TCCCGGCCTG GGCCCGAACC CCAGCGTGGA GGAGATCTAC
 199▶rArgValTrp AsnAlaArgL euProGluLe uProGlyLeu GlyProAsnP roSerValGl uGluIleTyr
 911 CGGGCCCTGG CCCGGGCCTA CCCCGGCGCG GCCTTCGCCC AGTACACCAC CCAGCTGGAC GGGACCCAGA
 223▶ArgAlaLeuA laArgAlaTy rProGlyAla AlaPheAlaG lnTyrThrTh rGlnLeuAsp GlyThrGlnI
 981 TCTACTTCTA CGCCCTCATG AAGAAGGAGG TACCCCCTC CGAGGCCACC GCCCGGGAGT GGGCCGTCCG
 246▶leTyrPheTy rAlaLeuMet LysLysGluV alProProSe rGluAlaThr AlaArgGluT rpAlaValAr
1051 GGCCCAGACC AGCCTCCAGA GCCTGGCCCA GGAGTCCAAC TTCACCTACT ACCTGGCCCC GGGGAGCCAA
 269▶gAlaGlnThr SerLeuGlnS erLeuAlaGl nGluSerAsn PheThrTyrT yrLeuAlaPr oGlySerGln
1121 CACTGCATCC TGCCCCGGCC CGAGCTCTAC ACCCTGAAGG TGGGGGAGGT GAGCGTTCTG GACTGGCTCA
 293▶HisCysIleL euProArgPr oGluLeuTyr ThrLeuLysV alGlyGluVa lSerValLeu AspTrpLeuA
1191 GGAGCCTGGC GGAGAAGGGG CAGGCCCCC GCGTAGGTCC GTGAGGTCGG GGAGGGCCTC GAGGAGGACC
 316▶rgSerLeuAl aGluLysGly GlnAlaProA rgValGlyPr o●●●
1261 CGGTACGCCT CCTTGGGGGA GGGGGCCTGG AGGAGGGCCC GGAGGACCCC CTCCCCTTTC GCCACCAGGA
1331 CGTCCGCCTT CAGGGCGAAG ACCCCTTGGA AGTAGAGGGC GTCCGCCAGG CTGGTGCGGA GCCGGTCATA
1401 GGCGCTGAGG CGGGGGTTGG GGGGTCTTAG CCGGGCGAGG AGGCGCGCCC AGGCCAGGTA AAGGGGGTAC
1471 CGCTCAGGGT AGGCCCCCTT CAGGGCGAAG AGGAAGAGGT AGTTGGCCAG GAACTCGTCC AGCCAGCGGC
1541 GGCCGGTCCT GAGCCGCCAG GCCACCTGGA CCGCGTGGGC GTGCTCGTGC CCCAGGGTGA GGTCCAAGAA
1611 CTCCTCCAGC GCCCCGGGGA GACCCTCCTC CGCCACAGGC AGGAGGACCT GGCGCAGGCG GTGGAGGAGG
1681 CGCTCGGGGT AGACCAGAGG GACGAAGAGG TAAAGCCGGG TCCGGCTCGT CCTCTGGAAG GGGAGGCCGT
1751 AGGGCACCCG GGTCCTCTCC CGCCAGTCCC TCTCCGAGAG GACGAAGAGG GTCACGGGGG AAGGGGGCG
1821 GTAGCGGGCC AGGAGGCGGT GGAGCCCCTC CAGGTAGGCC TGGACCTGGG CGGTGCGGGC CTTTCCCCCC
1891 GGGCTGTAGA AGGCGGGGAG GTCGGGGTGG GGAGGGCGT TCATATCACC TCCCGGAACC CGATGCGCTC
1961 CGCCTGGGCC TGGAGCTCCC GCCGCAGGAG GGGGTGGGCC TCGAGGCGGG GGTCCTTCTC CAGGATCTCC
2031 TACAACGTGG ACTTCTAAAG CCCGCCGGGC CCTCCCCCCG CCCCCCGGGG CGGGGGGTTG GCCTTTTTCC
2101 GGCCCAGGCC AGGGAGCCTT GCGCGTTCGG CGTTTGGCGT TCAGCCTTCG GCGTTTGGCC CATAATCGGG
2171 ACCAGGCGAA ACGGGTATCA TGGAGGTATG CGCTGGCTGG GGGTGCTCCT CCTGGGCCTG GCCCTGGCCC
2241 AGGGGCTGGA CCTGGCCCAG TCCCTCCTGC GCCAGGGCCA GTACGAGCAG GCCCTGGCCC GGCTGGAGCG
2311 GGAGCCCCCC GGCCCGGAGG TCCTGGCCCT GAAGGCCGG GCCTACCTGC CCTGGGCCG GCCGGAGGCG
2381 GCCCGGGAGG CCCTGGAGGG GGCGGCCCGC CTGGGCCGGG GGCGGAGGT GGAGCGGCTC AAGGGGTGGC
2451 TGGCCCTGGA GGCGGGAAAG GCCGAGGAGG CCCGGCGGGC CTTCCAGGCC GCGGCCATCT ACTCGGGCCT
2521 TCCCAAGAC GCCCTCCTCT GGGCCCTGCC GGCTTGGGAG GCCGGGCCGCT CTTCCGAGGA GGCCCTGGCC
2591 CGGGCGGAGC GGGCGGGAGG CGGGGCGGAG GCGGCCCTCC TTAAGGGGCT CTTCCTCCTG GCCCAGGACC
2661 CGGCGGAGGC CCTGGCCGCC TTCGCCGGG CGGGGACGG CCCCTTCAAG GCCCAGGCCC TCTACCTGCA
2731 GGGCCTGGCC CTCGAGGCCC TGGCCGGGA CCCGGAGGCC CGGGAGGCCT ACCGCCAGGC CCTGAAGGCC
2801 TCCCCGGACT ACCTCCCCGC CCGCCGGGCT TTAGGGCTCT AGTACCACCC CATCCTGGCG TACGCCAGGA
2871 TGGGGCCCC GGTAAAGCCT TAGCCTTCCG ACGAAGCGGG GAATGAGGGG AAGCCTGAAT GACGGAAAAG
2941 AGGATGGAAA AATCGGTCTT CCGCTACCAA GGCCCCGAGC CCAAGGGGGA CCAGCCCAAG GCCATCCGGG
3011 AGCTGGTGGA GGCCCTGGAG GCGGGGAGC GGTTCGTCAC CCTTTTGGGG GCCACCGGCA CGGGGAAGAC
3081 GGTCACCATG GCCAAGGTGA TCGAGGCCCT GGGCAGGCCC ACCCTGGTCC TCGCCCCCAA CAAGATC
```

TspA E101
sequence with ORF

FIGURE 16H

STABLE BIOCATALYSTS FOR ESTER HYDROLYSIS

This application claims priority to U.S. Provisional Applications for patent Ser. No. 06/019,580, filed Jun. 12, 1996; Ser. No. 60/009,704, filed Jan. 11, 1996; and Ser. No. 60/001,995, filed Aug. 7, 1995, all of which are hereby incorporated by reference in their entirety.

STATEMENT OF GOVERNMENT RIGHTS

The work disclosed in this application was supported in part by Grant Number: NCI 1-R43-CA63876-01 from the NIH-SBIR to ThermoGen Inc., therefore, the U.S. Government may have some rights in the present invention.

FIELD OF THE INVENTION

The instant disclosure is directed to the field of isolated stable biocatalysts that are suitable for enzymatic application in commercial pharmaceutical and chemical synthesis, DNA vectors for the production of recombinant ester hydrolyzing proteins, host cells transformed by such vectors, and recombinant ester hydrolyzing proteins produced by such vectors and transformed cells.

BACKGROUND OF THE INVENTION

Esterases and Lipases. Esterases and lipases catalyze the hydrolysis of ester bonds to produce alcohols and carboxylic acids as shown below.

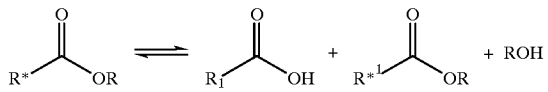

Esterases and lipases can be characterized by different substrate specificities, R group or chain length preference, and unique inhibitors (1, 2). The many esterases and lipases range from hydrolases such as the broad carboxyl esterases which preferentially hydrolyze esters with long carbon chain R groups, to choline esterases, and to acetyl esterases which act on very specific substrates. In many cases, these hydrolases are also known to show stereo- and regio-selective preferences resulting from the chiral nature inherent in protein active sites. This preferential hydrolytic activity make them useful for reactions requiring different regioselectivity and stereoselectivity or for kinetic resolution methods on racemic mixtures. For enzymes that demonstrate stereoselectivity, if R* is a racemic mixture, the product of enzyme catalyzed hydrolysis, $R_1$, would be the most rapidly hydrolyzed stereoisomer while the remaining ester designated R*' would be the enriched antipode mixed with any remaining $R_1$. The products can then be separated by chromatography to provide pure $R_1$. The availability of a large pool of esterases and lipases with varying specificities would be useful for screening the enzymes for specific reactions, and developing optimal protocols for specific chemical synthesis. The expedience of this process would facilitate the production scale-up of many useful pharmaceutical products.

In aqueous solvent systems, esterases and lipases carry out their natural reactions: the hydrolysis of ester bonds. In vitro, these enzymes can be used to carry out reactions on a wide variety of substrates, including esters containing cyclic and acyclic alcohols, mono- and di-esters, and lactams (3). By carrying out the reactions in organic solvents (4, 5) where water is excluded, the reactions of esterases and lipases can be reversed. These enzymes can catalyze esterification or acylation reactions to form ester bonds (3, 6, 7). This process can also be used in the transesterification of esters and in ring closure or opening reactions.

Optically pure chiral pharmaceuticals. Currently, the majority of synthetic chiral pharmaceuticals are sold as racemic mixtures. However, due to advances in the synthesis of optically pure (single isomer) chiral compounds, this situation is changing (7). Racemic drugs often contain one isomer which is therapeutically active and the other enantiomer which is at best inactive and at worst a major cause of potentially harmful side effects. The non-useful isomer in a racemic drug is increasingly being viewed as a contaminant. Indeed, the FDA's Policy Statement for the Development of New Drugs recommends "that the pharmacokinetic profile of each isomer should be characterized in animals and later compared to the clinical pharmacokinetic profile obtained in Phase I" drug testing (8). Thus, pharmaceutical companies will need to develop a synthesis or separation route to produce each pure isomer of each new synthetic drug.

Enzymatic synthesis of optically pure pharmaceuticals and intermediates. Since it is often very difficult to generate optically pure solutions of certain chiral molecules by classical chemical synthesis, new enzymatic biocatalysts will play a major role in this endeavor. In some cases, enzymes may be able to replace hazardous chemical synthesis procedures with more environmentally-friendly biological synthesis processes. It can also be much more cost effective to produce a pharmaceutical intermediate enzymatically if an enzyme can eliminate several chemical protection and deprotection steps at once (7). All six major classes of enzymes (oxidoreductases, transferases, hydrolases, lyases, isomerases, and ligases) have been useful in the synthesis of optically pure compounds as described in several detailed reviews (3, 7). The hydrolases have proven to be the most useful group of enzymes, due to the abundance of hydrolases, the information about them, their independence from cofactors, and the wide variety of substrates they can accept.

A survey of the literature shows many examples of mesophilic hydrolases particularly esterases and lipases used in chemical synthesis or chiral resolution. These include esterases from pig (9, 10) and horse (3) livers and a wide variety of lipases from Aspergillus sp, (11) Candida sp. (12–16), Pseudomonas sp., (17–19), Rhizopus sp. (20) and others. Several lipases have been used in the synthesis of propranolol (7), a beta-adrenergic blocking agent used in the treatment of angina and hypertension. Ibuprofen, a nonstearoidal antiinflammatory agent has been synthesized via stereo selective hydrolysis of its methyl ester using carboxyesterase (7). While these enzymes have begun to demonstrate the utility of biocatalysts in chemical synthesis, there is still a profound need for a wider variety of esterases and lipases which have varying substrate specificities, regioselectivities, and steroselectivities. In addition, since these enzymes need to be employed in a large-scale industrial setting, there is a need for them to have increased stability, higher thermotolerance and a longer "shelf life".

Thermostable enzymes. Thermophilic organisms have already provided a rich source of useful proteins that catalyze reactions at higher temperatures and are stable for much longer periods of time (21, 22). One example is the DNA Polymerase I from *Thermus aquaticus* and its use in polymerase chain reaction (PCR) (23, 24). Thermophilic enzymes have become the most commercially successful enzymes in industry because of their long-term stability and ease of use. The most successful enzyme to date, alpha-amylase, is used in corn processing and comes from the moderate thermophile *B. stearothermophilus* (25). Another commercially successful industrial enzyme is subtilisin, a serine protease also found in various strains of Bacillus, has been widely used in laundry detergents and other cleaning solutions.

The commercial success of these enzymes can be attributed to their ease of use. In addition to functioning at high temperatures, thermostable enzymes generally posses an increased shelf life which markedly improves handling conditions, especially by those not trained in biochemistry to work with the specific range of conditions used for mesophilic enzymes. If enzymes are to play a significant role in large scale processing of chemicals, they must be able to endure the harsh conditions associated with these processes. Thermostable enzymes are easier to handle, last longer, and given the proper immobilization support should be reusable for multiple applications Finally, the hydrophobic and electrostatic forces that allow these enzymes to survive high temperatures also allow them to generally function better in organic solvents (26–31). While most enzymes lose a significant portion of their activity in organic solvents, thermostable enzymes may prove more tolerant to the denaturing conditions of many organic solvents. Highly thermostable esterases and lipases are necessary to expand the application of these biocatalysts in large scale industrial reactions.

Thermostable esterases and lipases. To date, only one esterase and a few lipases have been reported with moderately thermostable characteristics. Tulin et al. (32) reported a Bacillus stearothermophilus esterase cloned into *Bacillus brevis* which was stable up to 10 minutes at 70° C. Sugihara et al.(33, 34) have isolated novel thermostable lipases from two microorganisms, A Bacillus soil isolate and a *Pseudomonas cepacia* soil isolate. The former lipase is stable up to 30 minutes at 65° C. but rapidly inactivated above this temperature. The lipase from *Pseudomonas cepacia* was stable when heated for 30 minutes at 75° C. and pH 6.5 but had only 10% of its activity when assayed at this temperature. A thermoalcalophilic lipase (35) was identified from a Bacillus species MC7 isolated by continuous culture and had a half-life of 3 hours at 70° C. Finally, Sigurgisladottir et al. (6) have reported the isolation of one Thermus and two Bacillus strains which posses lipases active on olive oil up to 80° C., although there was no report on enzyme stability in this study.

These enzymes offer only limited variations in substrate specificities and only moderate thermostability profiles. They do not address the need for different substrate specificities, the need to produce large scale quantities which can be economically commercialized, and many of them have only limited overall stability. In this patent application we have identified a series of esterases and lipases which offer a range of substrate specificities (including regioselectivity, stereoselectivity), enhanced enzyme stability, and can be produced in large quantities for commercial use.

SUMMARY OF THE INVENTION

The instant invention provides for the isolation and characterization of commercial grade enzyme preparations characterized by esterase activity, and corresponding to the data as disclosed in FIGS. 1–4 and Table 1. In a preferred embodiment, the instant invention provides for the isolation, and characterization of specifically purified esterase which is characterized by esterase activity, and corresponding to the data as disclosed in Table 1 and FIGS. 5–9. In a most preferred embodiment, the instant invention provides for proteins generated by recombinant DNA technology which have esterase activity. The enzymes of the instant disclosure can be isolated from thermophilic organisms from various sources including soil, water and refuse sites from across the United States and elsewhere in the world. These organisms generally grow in the temperature range of 45° C. to 90° C. which classifies them as moderate to extreme thermophiles. Proteins isolated from this group of organisms are similar in function to those isolated from species that grow at lower temperatures 25° C. to 37° C., but are lacking in thermostable characteristics. The enzymes of the instant disclosure encompass proteins produced by thermophilic organisms including the esterase enzymes which are responsible for the hydrolysis of ester bonds to yield carboxylic acids and alcohols. The proteins of the instant disclosure possess activity lifetimes considerably longer than found for unmodified mesophilic enzymes: retain activity even after exposure to elevated temperatures for extended periods of time, and resist inactivation in the presence of organic cosolvents. The proteins encompassed by the instant disclosure can be isolated by standard purification methods, specifically, and by ion exchange chromatography. The enzymes of the instant disclosure are all intracellular proteins that can be recovered by cell disruption and loaded on to DEAE cellulose. Purified esterases of the instant disclosure are eluted by NaCl gradients; fractions containing single activities are pooled and concentrated prior to lyophilization for storage. Specific activity is determined by measuring the total concentration of protein either by the Pierce BCA method or by measuring the UV absorbance at 280 nm followed by an activity assay based on the initial hydrolysis rate of p-nitrophenylproprionate. The proteins of the instant disclosure can be characterized by the strain of bacteria from which they were isolated, the growth in TT media at 55° C. and 65° C., and by esterase hydrolytic activity. The proteins of the instant disclosure can be characterized by esterase activity in selection microtiter plate assay. The proteins of the instant disclosure can also be characterized by the temperature profile, protein stability profile, and pH profile of the protein. The proteins of the instant disclosure can be characterized by apparent molecular weight corresponding to esterase activity stain on native gradient PAGE gels. Specific molecular weight can be further characterized by chromatography, and specific activity can be further determined under standard conditions, where Table 10 contains a summary of many of these characteristics for selected proteins. Thus the proteins of the instant invention can be characterized by inherent properties as well as by their amino acid protein sequence, or by a nucleic acid sequence which will encode for the amino acid protein sequence of the protein.

Thus, the instant disclosure encompasses a library of stable esterases isolated from a bank of thermophilic organisms, which are useful in the selective preparation of chiral pharmaceutical intermediates and other fine chemicals. The library consists of at least 23 purified enzymes that can be used either in various combinations as a screening kit, or as individual protein preparations to carry out chemical reactions or prepare chiral products using kinetic resolution techniques. Under these conditions, racemic esters will have different rates of hydrolysis catalyzed by the enzymes depending on which stereoisomer best fits the structural parameters of the enzyme active site. The products carrying the chiral center(s) may be on either the carboxylic acid or the alcohol. In addition, many of the esterases described herein may be used to prepare chiral esters from carboxylic acids and alcohols if the reaction is run in the synthetic direction under transesterification conditions in which water is limited in solvent.

The instant disclosure encompasses lambda phage expression vectors which contain an insert that can be used for the production of recombinant ester hydrolyzing proteins of the instant invention, from a transformed cell host. The insert contained on the lambda phage expression vector may be used in, for example, a phage-plasmid hybrid expression vector or other suitable expression vector such as, but not limited to, plasmids, YACs, cosmids, phagemids, etc. In a preferred embodiment, a lambda expression vector is one of the vectors named in Table 7, or one which contains an insert which encodes for a substantially similar recombinant protein. The instant disclosure also provides for vectors which are capable of transforming a host cell, and which encode for recombinant ester hydrolyzing proteins, the transformed host cells, and the recombinant ester hydrolyzing protein. Appropriate host cells include but are not limited to: $E.\ coli$, Bacilli, Thermus sp., etc. The recombinant ester hydrolyzing protein encoded by the vector is capable of hydrolyzing 5-bromo-4-chloro-3-indolyl-acetate (X-acetate). The recombinant ester hydrolyzing protein produced by the vector can be further characterized by a half-life stability comparable to that of a corresponding protein purified from the isolates. The recombinant ester hydrolyzing protein is also characterized by the ability to remain stable at temperatures comparable to, or better than that of the corresponding protein from the original isolates. Recombinant ester hydrolyzing protein encoded for by the vector can also be characterized by certain substrate specificities as discussed below, which are comparable to those of the corresponding purified protein from the isolates. In a preferred embodiment the vector is a vector named in Table 7 or 8, or one which contains an insert which encodes for a substantially similar recombinant protein. In a preferred embodiment of the instant invention, a vector which encodes specific recombinant ester hydrolyzing protein is one of the vectors named and listed in Table 8, and deposited with the American Type Culture Collection (ATCC, Rockville, Md., USA) under the terms and conditions of the Budapest Treaty for the Deposit of Microorganisms, and given a specific designation number by the ATCC, to be amended to the specification upon receipt of such numbers.

BRIEF DESCRIPTION OF THE DRAWINGS

FIG. 2. Esterase activity stain of crude extracts from thermophiles. After electrophoresis, the gels are equilibrated in pH 7.6 Trizma buffer and then stained for activity in either 0.15% X-acetate. The gels are then incubated at 55° C. for up to 30 minutes.

FIG. 3. Molecular Weight calibration curve. FIG. 3 depicts a standard molecular weight calibration curve.

FIGS. 4A–S depict the activity profiles which characterize enzymes of the instant disclosure. For each enzyme listed, Graph 1 depicts the Temperature Profile of the enzyme plotting relative esterase activity versus temperature. Graph 2 depicts the Residual Esterase Activity of the listed enzyme plotting relative remaining activity versus time in hours, at 25° C., 40° C., and 65° C. Graph 3 depicts the pH profile for the listed enzyme plotting Relative Esterase Activity versus pH.

FIG. 6. Kinetic analysis of E100. The enzyme displays normal Michaelis kinetics yielding linear data with both a) Lineweaver-Burke and b) Eadie-Hofstee analysis to give a Km=$7.2\times10^{-5}$M and Vmax=$1.8\times10^{-5}$ Mmin$^{-1}$ using p-NP as the substrate.

FIG. 7. Temperature and pH profiles of E100. a) Temperature profile of E100. Plot of E100 catalyzed hydrolysis of p-nitrophenyl proprionate as a function of temperature. Enzyme activity was determined upon exposure to different temperatures. Initial rates of nitrophenylproprionate hydrolysis were determined in 50 mM borate Buffer pH 8.5 equilibrated to the desired temperature to which 0.25 mM substrate dissolved in CH$_3$CN was added followed by enzyme. Rates were determined by monitoring the change in absorbance at 405 nm and corrected for the spontaneous hydrolysis of substrate substituting bovine serum albumin for enzyme. b) pH profile of E100. The effect of pH on the hydrolysis of p-nitrophenyl proprionate catalyzed by E100. The pH profile of the enzyme was determined by preparing different buffers appropriate for the desired pH's at 10 mM concentration. Reactions were performed by addition of the substrate (0.25 mM) dissolved in CH3CN to the buffer solution followed by the enzyme. Reactions were incubated for 5 minutes after which the reaction was terminated by addition of 0.1 mM PMSF dissolved in CH$_3$CN. The pH of the mixture is adjusted to 8.5 by addition of 0.1M Tris-HCl. Absorbances are recorded at 405 nm and concentrations calculated based on the $\epsilon$=17 mM$^{-1}$ $^{cm-1}$ for the product nitrophenol. Formation of products is corrected for the spontaneous hydrolysis of the substrate.

FIG. 9. Purification of E101. a) Steps in the purification of E101 as shown by 10% SDS-PAGE. Lane 1. Molecular weight markers. Lane 2. purified E100 (included as standard). Lane 3. dialyzed protein after NH$_4$SO$_4$ fractionation. Lane 4. DEAE load/wash. Lane 5. SP Sepharose load/wash. Lane 6. Purified E101 eluted from S200 gel column. b) 10% SDS-PAGE of E101. Lane 1. Boiled E101. Lane 2. Nonboiled E101. Lane 3. Molecular weight markers.

FIG. 10. Substrates used to screen stereo- and regioselectivity. Esterases are versatile biocatalysts in the sense that stereo- and regio-selectivity can be mediated by substrate structure which fall into four types. The compounds listed represent a range of different structural features encountered in common substrates with potential importance for the chemical intermediate industry. Several of the substrates are commercially available in entantio- or diastereomerically pure form and can be used in qualitative screening procedures described in the text. Four classes of substrates most commonly associated with hydrolytic biocatalysts for chiral centers resolution are considered. A) Type I substrates position the desired product on the carboxylic acid side of the product, while Type II compounds the alcohol contains the requisite functionality. B) Type III and Type IV substrates can be considered subsets of Types I and II, but their unique properties dictate that they be classified separately. Type III molecules require that the enzyme differentiates a prochiral substrate while Type IV compounds are meso structures. These last two substrate types demonstrate the synthetic importance of biocatalyst based resolution methods as these types of compounds are very difficult to selectively operate upon by other chemical means.

FIG. 11. Selection process for Recombinant Esterases. a). Screening of the phage library from strain isolate 28 (E009) using an X-Acetate gel overlay. Blue halos surround single phage plaques expressing esterase. b) Purification of hybrid phages produced from the 54 (E002) strain. Halos of the hydrolyzed X-Acetate chromogenic substrate surround each phage plaque of the three phage stocks. c) and d) A Spot-test for the hydrolyzing activity of the plasmid-carrying strains derived from phages λTGE1.1; λTGE1.2; λTGE1.3; λTGE2.1; λTGE2.2; λTGE2.3; λTGE2.4; λTGE2.8; λTGE3.2; λTGE3.3; λTGE3.4; λTGE4.1; λTGE4.2; λTGE4.3; λTGE11.1; λTGE11.3; λTGE11.4; λTGE11.7; λTGE11.9; λTGE11.10; λTGE15.1; λTGE15.3; λTGE15.5; λTGE15.8; λTGE15.9. Higher activity detected by X-Acetate is strongly associated with weaker growth.

FIGS. 12a–r. Examples of screening technique using esterase activity stain of recombinant protein from phage lysates. Once esterase-positive candidiates are identified, phage lysates are screened for the correct ester hydrolysis activity on a native 4–15% gradient BioRad ReadyGel. After electrophoresis, the gels are equilibrated in pH 7.6 Trizma buffer and then stained for activity by using a 0.15% X-acetate overlay. The gels are then incubated at room temperature for up to 30 minutes. The figures shows a typical examples of how the technique is used to identify proteins with the same mobility characteristics as the native protein. a) Screening positive clones from a bank made from strain isolate S1 to identify E001. Lanes indicate lambdaTGE1 isolates 1, 2, 3, 4, 5, 8 and native control protein (C); b) Screening positive clones from a bank made from strain isolate 54 to identify E002. Lanes indicate lambdaTGE2 isolates 1, 2, 3, 4, 6, 8 and native control protein (C); c) Screening positive clones from a bank made from strain isolate 50 to identify E003. Lanes indicate lambdaTGE3 isolates 1, 2, 3, 4 and native control protein (C); d) Screening positive clones from a bank made from strain isolate GP1 to identify E004. Lanes indicate lambdaTGE4 isolates 1, 2, 3, 4, 5, 6 and native control protein (C); e) Screening positive clones from a bank made from strain isolate C-1 to identify E005. Lanes indicate lambdaTGE5 isolates 1, 2, 3, 4, 5, 6 and native control protein (C); f) Screening positive clones from a bank made from strain isolate 55 to identify E006. Lanes indicate lambdaTGE6 isolates 1, 2, 3, 4, 5, 6 and native control protein (C); g) Screening positive clones from a bank made from strain isolate 30 to identify E008. Lanes indicate lambdaTGE8 isolates 1, 2, 3, 4, 5, 6 and native control protein (C); h) Screening positive clones from a bank made from strain isolate 28 to identify E009. Lanes indicate lambdaTGE9 isolates 1, 2, 3, 4, 5, 6, 7 and native control protein (C); i) Screening positive clones from a bank made from strain isolate 29 to identify E010. Lanes indicate lambdaTGE10 isolates 1, 2, 3, 4, 5, 6, 7, 8, 9, 10, 11, 12 and native control protein (C); j) Screening positive clones from a bank made from strain isolate 31 to identify E011. Lanes indicate lambdaTGE11 isolates 1, 2, 3, 4, 7, 8 and native control protein (C) on the first gel and lambda TGE11 isolates 7, 8, 9, 10 and native control protein (C) on the second gel; k) Screening positive clones from a bank made from strain isolate 26b to identify E012. Lanes indicate lambdaTGE12 isolates 1, 2, 3, 4, 5, 6 and native control protein (C); l) Screening positive clones from a bank made from strain isolate 27 to identify E013. Lanes indicate lambdaTGE13 isolates 1, 2, 3, 4, 7, 8 and native control protein (C); m) Screening positive clones from a bank made from strain isolate 34 to identify E014. Lanes indicate lambdaTGE14 isolates 3, 5, 6, 8, 9 and native control protein (C); n) Screening positive clones from a bank made from strain isolate 62 to identify E015. Lanes indicate lambdaTGE15 isolates 1, 2, 3, 4, 5, 6, 7, 8 and native control protein (C); o) Screening positive clones from a bank made from strain isolate 47 to identify E016. Lanes indicate lambdaTGE16 isolates 1, 2, 3, 4, 5, 6, 7 and native control protein (C); p) Screening positive clones from a bank made from strain isolate 4 to identify E019. Lanes indicate lambdaTGE19 isolates 1, 2, 3, 4, 5, 6 and native control protein (C); q) Screening positive clones from a bank made from strain isolate 7 to identify E020. Lanes indicate lambdaTGE20 isolates 3, 4, 6, and native control protein (C); r) Screening positive clones from a bank made from strain isolate 32 to identify E021 (E017b). Lanes indicate lambdaTGE21 isolates 6, 8, 9 and native control protein (C);

FIG. 13. The effect of temperature on stability of clones. The recombinant strains harboring plasmids with active esterase proteins often exhibited a phenotypic segregation of the esterase activity on X-acetate plates. This segregation could be due to plasmid or insert loss if the esterase activity had toxic properties to the cell. To overcome this cells could be grown at lower temperatures (presumably reducing the activity of the cloned thermophilic esterases). Shown in this figure, strains TGE15.2 (15) and TGE15.9 (14) are plated with X-Acetate at 28° C. (a) and 37° C. (b). Yellow colonies of faster growing segregants are visible at both temperatures, but contra-selection at 37° C. is much stronger. The same phenomenon is shown in (c) and (d) for strains TGE2.1 (1); TGE2.2 (2) and TGE3.2 (3) grown at 28° C. and 37° C. respectively.

FIGS. 14. Examples of esterase stain of recombinant protein from plasmids. Protein extracts from both the native organism (single column purified) and a recombinant production strain are compared. Protein extracts are run on a 4–15% Gradient BioRad Ready Gel. After electrophoresis, the gels are equilibrated in pH 7.6 Trizma buffer and then stained for activity in either 0.4% X-acetate using an X-Acetate overlay. The gels are then incubated at room temperature for up to 30 minutes. In these examples: E007 from the native organism (E007 N) and a protein extract from strain CE007 with no visible activity on this stained gel; E008 from the native strain and recE008 from CE008; E009 from the native organism and recE009 from strain CE009; E010 from the native organism and recE010 from strain CE010; E011 from the native organism and recE011 from strain CE011; E014 from the native organism and recE014 from strain CE014; E015 from the native organism and recE015 from strain CE015; E017b from the native organism and recE017b from strain CE017b; E019 from the native organism and recE019 from strain CE019; E021 from the native organism, recE020 from strain CE009 (R) and recE028 from strain CE028—both isolated from the same gene bank. recE028 can be seen in the background of the native protein prep as a low level secondary activity; N=Native protein; R=Recombinant protein; R*=alternate recombinant protein with a different migration pattern (in this case E028, cloned from the same strain as E020).

FIG. 16. Nucleic acid sequence and translated protein amino acid sequence. The isolation and cloning of the genes encoding for the enzymes of the instant invention will result in DNA segments in which an open reading frame (ORF) may be found which corresponds to the translated protein amino acid sequence. Alternative start codons are recognized in the art, however the encoded protein will comprise at minimum a core protein ORF. FIG. 16A is an isolated nucleic acid sequence, and translated amino acid sequence which correspond to E001 enzyme ORF, alternative start codons are underlined. FIG. 16B is the cloned isolated nucleic acid sequence which contains the E001 ORF. FIG. 16C is an isolated nucleic acid sequence, and translated amino acid sequence which correspond to E009 enzyme ORF, alternative start codons are underlined. FIG. 16D is the cloned isolated nucleic acid sequence which contains the E009 ORF. FIG. 16E is an isolated nucleic acid sequence, and translated amino acid sequence which correspond to E011 enzyme ORF, alternative start codons are underlined. FIG. 16F is the cloned isolated nucleic acid sequence which contains the E011 ORF. FIG. 16G is an isolated nucleic acid sequence, and translated amino acid sequence which correspond to E101 enzyme ORF, alternative start codons are underlined. FIG. 16H is the cloned isolated nucleic acid sequence which contains the E101 ORF.

DETAILED DESCRIPTION OF THE INVENTION

Figure 1:
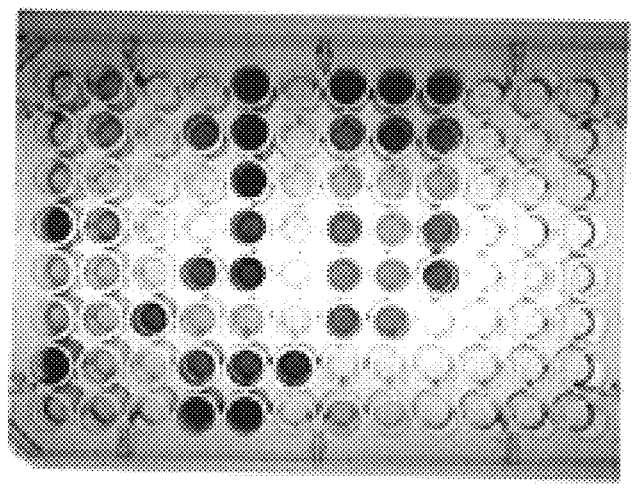
FIG. 1. Esterase Screening plate. Fifty microliters of cell extract is transferred to a well on a microtiter plate consisting of 0.1 mg/ml of either 5-bromo-4-chloro-3-indolyl acetate or butyrate (for esterase activities) suspended in 0.7% agarose and 0.1M Tris-HCl pH 8.0. Control wells consist of addition of either buffer, 20 U of Pig Liver Esterase (PLE), or 20 U of Porcine Pancreatic Lipase (PPL). Plates are incubated for sufficient time to allow full color development in control wells, usually about twenty minutes at 37° C. Dark wells represent positive activity. This photograph demonstrates the screening of 65 candidate isolates, and the resulting positives.
Figure 4A:
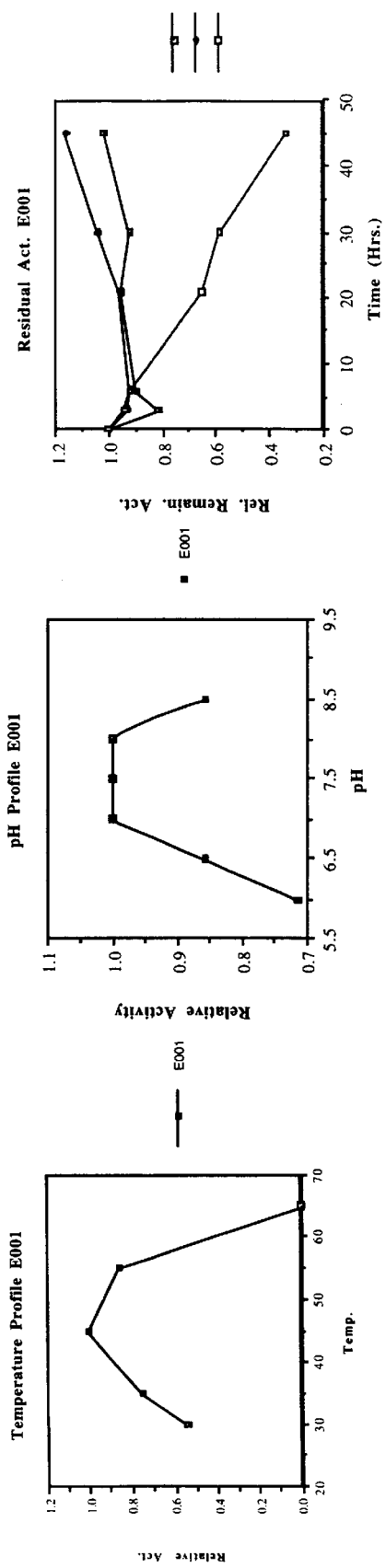
FIGS. 4A–S. Enzyme Characteristics.
Figure 4B:
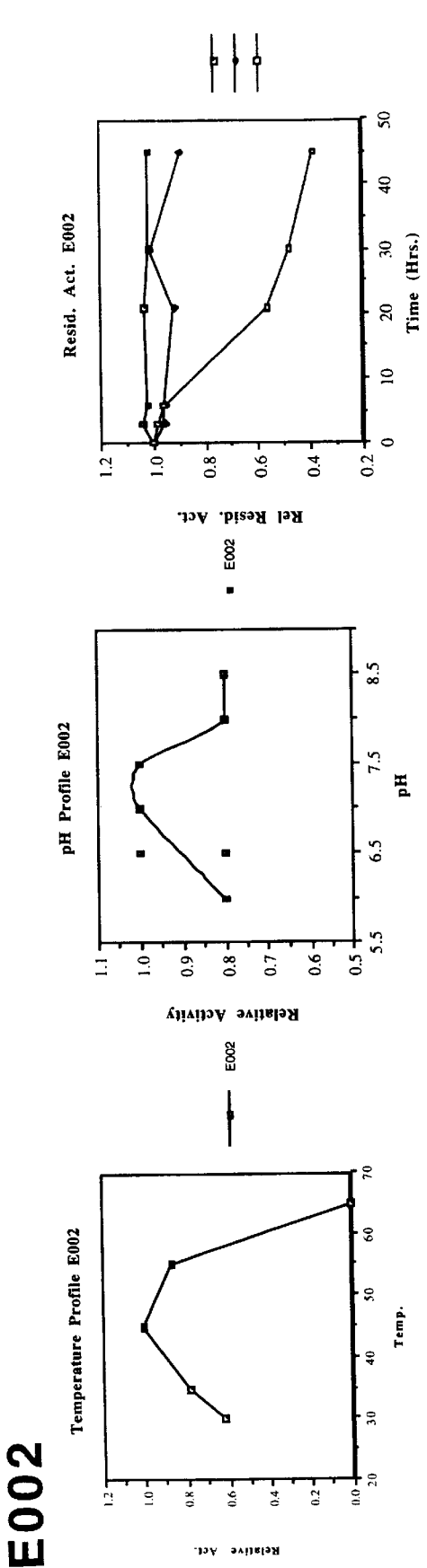
Figure 4D:
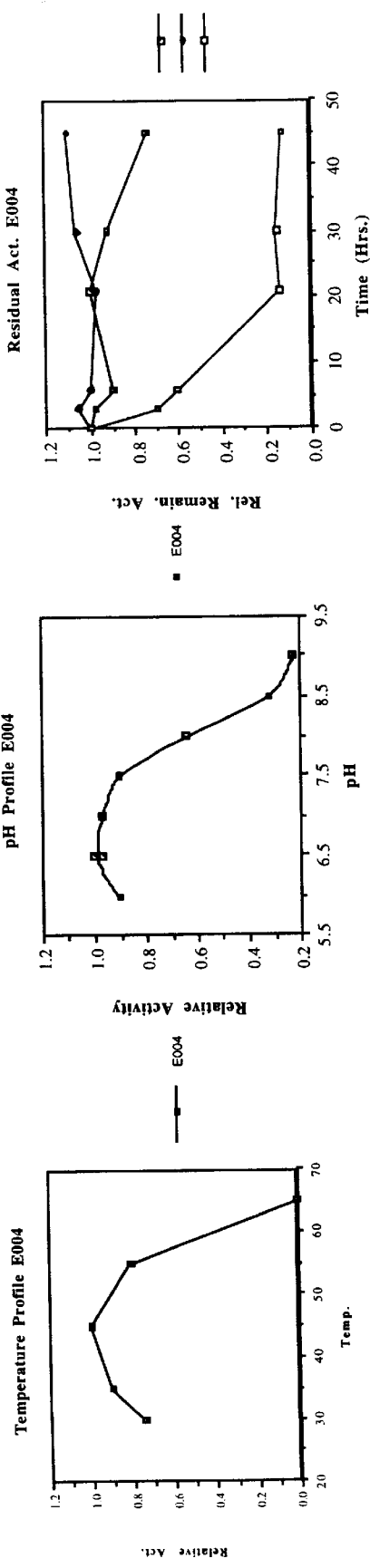
Figure 4F:
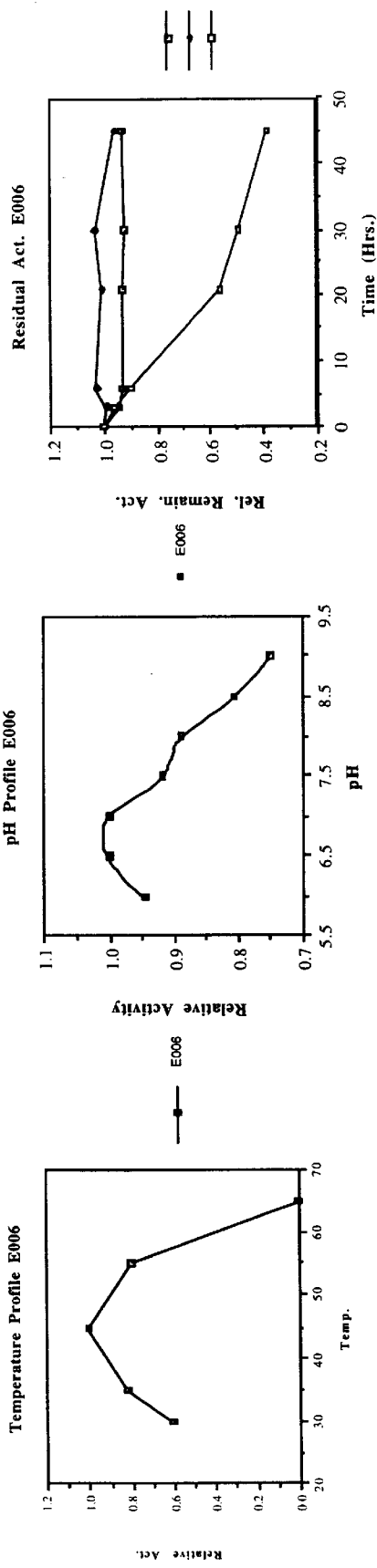
Figure 4H:
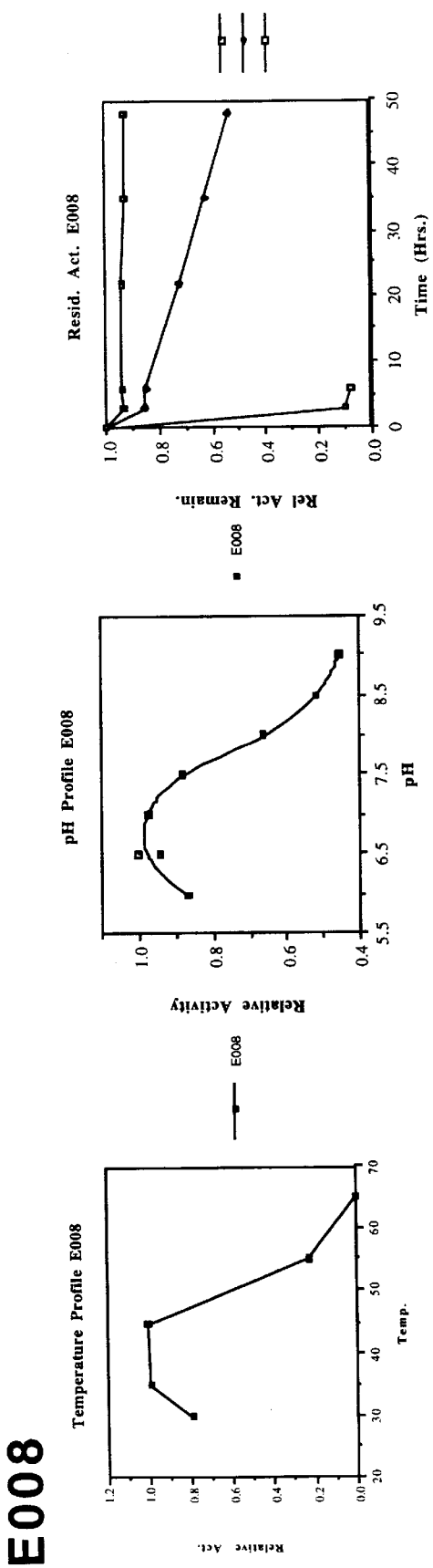
Figure 4I:
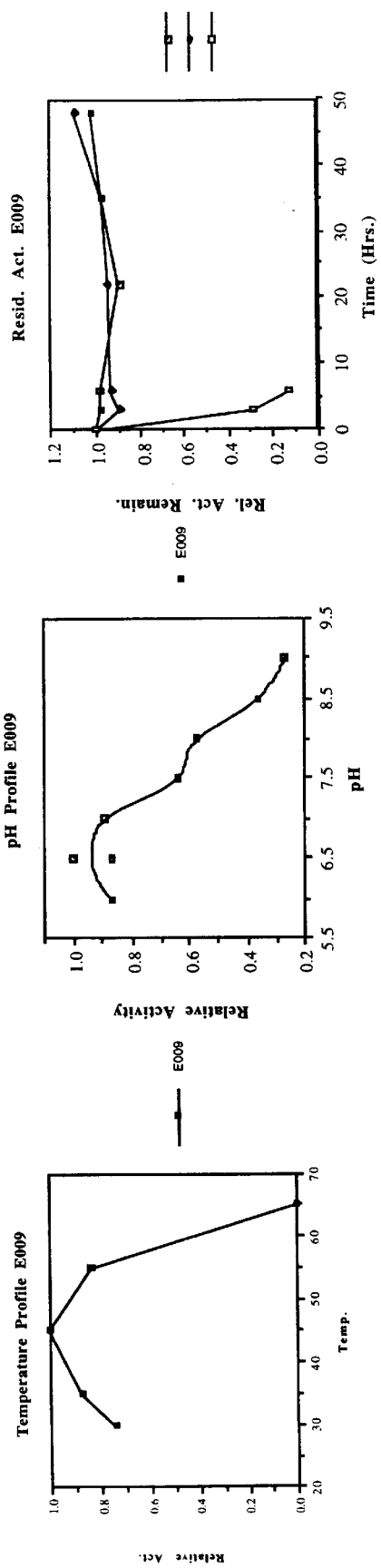
Figure 4K:
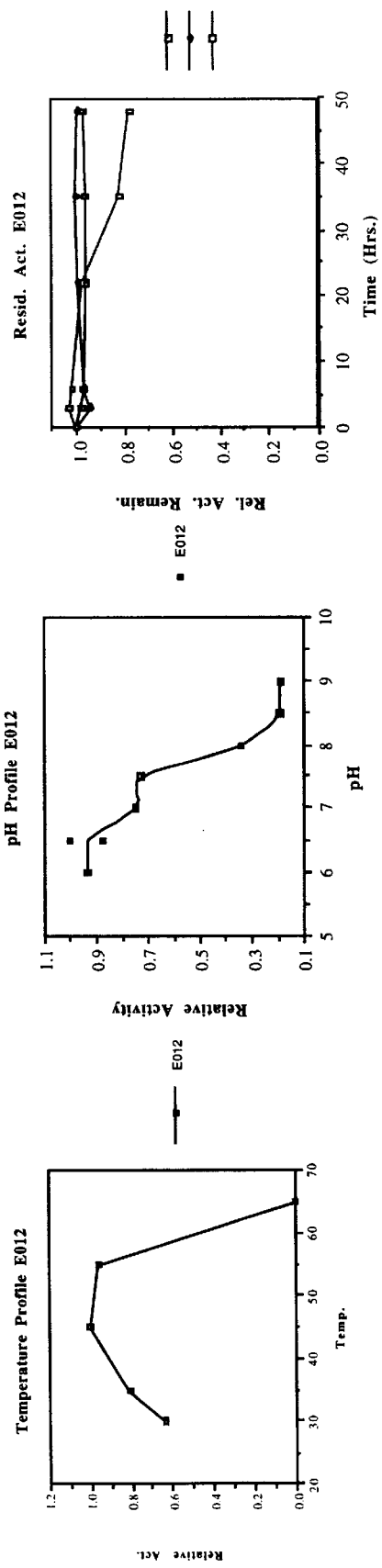
Figure 4M:
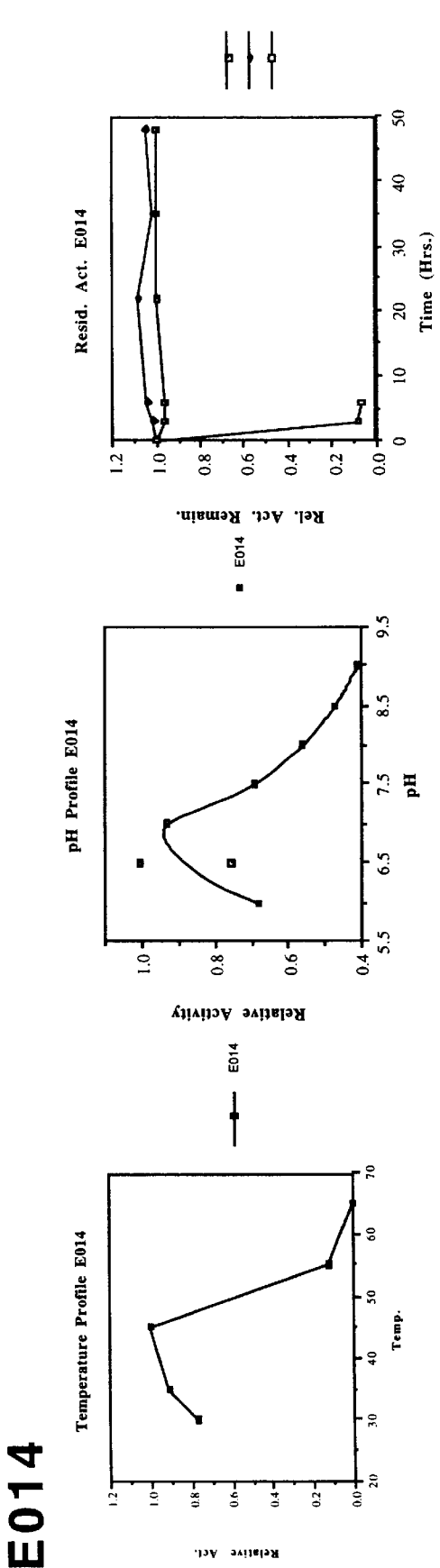
Figure 4P:
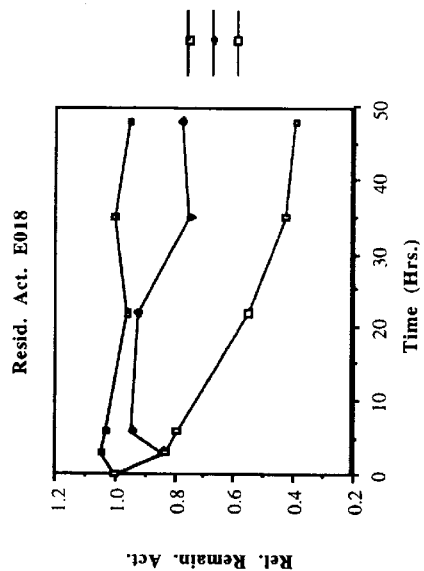
Figure 4S:
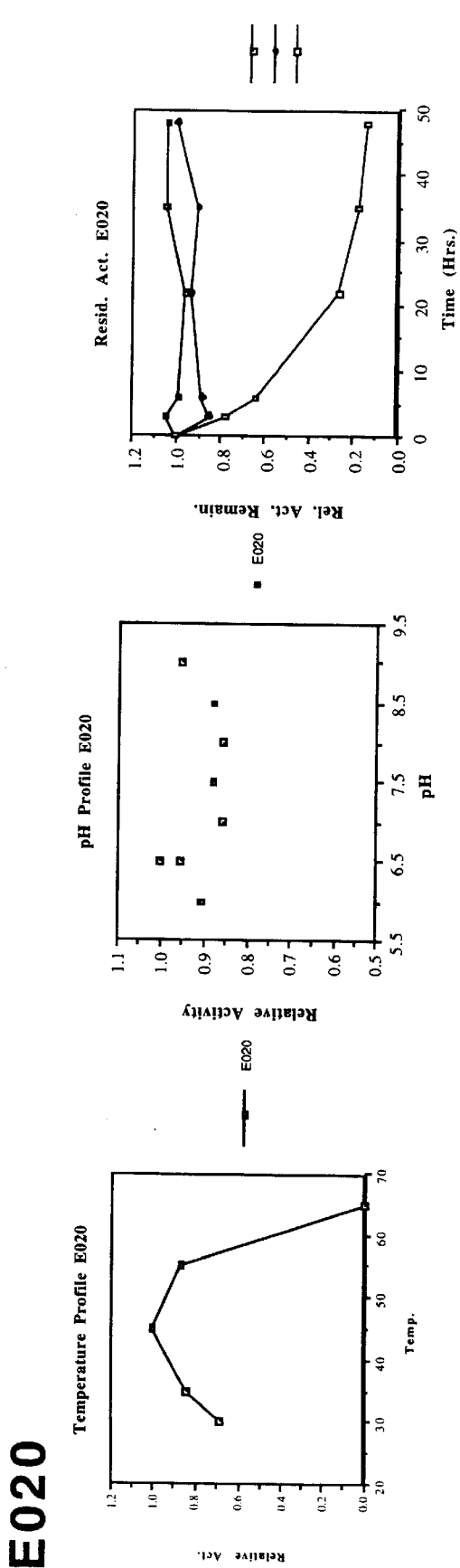

The instant invention provides for isolated commercially useful protein preparations from themostable bacteria which are selected for enzymatic activity, and characterized by apparent molecular weight, pH, and temperature stability. The isolated protein of the instant disclosure can be used as molecular weight markers for finding similar enzymes, as well as functionally as enzymes for carrying out biocatalysis. Commercial chemical synthesis of specific racemic products often require the use of such isolated enzyme preparations.

The results of characterization assays demonstrate that the esterase enzymes described have a range of optimal parameters. For instance, E100 and E101 have optimal operating temperatures above 70° C. as would be consistent with enzymes isolated from an extreme thermophile, and E001–E021 have optimal commercial temperatures in the range of 40–50° C. as would be consistent with enzymes isolated from the more moderate thermophilic organisms. Both groups, however, provide added stability and functionality as compared to other known esterases from thermophilic bacteria. E001–E021 provide an optimal temperature environment for chemists who wish to work in less extreme temperature ranges, and also function well at room temperature. The results also demonstrate that the enzymes described posses a variety of pH optima including some with no apparent preference under the conditions of the experiment, however the trend for most of the proteins is to have pH optima near or slightly below neutral.

The following examples are meant by way of illustration, and not limitation, as to the specific embodiments of the instant invention. One of ordinary skill in the art would understand that many equivalents to the instant inventions can be made with no more than routine experimentation.

EXAMPLE 1

Isolation and Propagation of Thermophilic Organisms

Strains—Thermus sp. T351 (ATCC 31674) is available from the American Type Culture Collection (ATCC). All isolated strains and cultures are grown on TT medium (36). This medium consists of (per liter): BBL Polypeptone (8 gm), Difco Yeast Extract (4 gm), and NaCl (2 gm). Small scale cultures for screening are grown at 65° C. at 250–300 rpm with 1 liter of medium in a 2 liter flask. Larger scale production of cells for enzyme purification are grown in 17 liter fermentors (LH Fermentation, Model 2000 series 1). The fermentors have a working volume of 15 liters and cultures were grown in TT broth, 250 rpm, 0.3 to 0.5 vvm (volumes air/volume media per minute) at 65° C. Temperature is maintained by circulating 65° C. water from a 28 liter 65° C. water reservoir through hollow baffles within the stirred jars. E. coli strains are grown as described in (37).

Enrichment Procedures for Newly Isolated Thermophiles Multiple stream sediments, composting organic materials, and soil samples are used to isolate new strains. These samples are collected from numerous geographic sites ranging from the Midwest to the Southeast. Samples (~1 gm) are resuspended in 2 ml of TT broth and 50–100 µl of these samples were plated onto TT agar plates containing twice the usual amount of agar (3%). Agar is usually added to a final concentration of 1.5% for solid media. This prevents highly motile microorganisms from overcrowding the plate at the expense of other microbes. Plates are incubated at 55° C. or 65° C. for one to two days and isolates then purified by numerous restreaks onto fresh plates for single colony isolation. The initial basis for differentiation is color, colony morphology, microscopic examination, temperature of growth, and lipase and esterase activities. Several hundred strains were initially isolated. 65 different microorganisms were chosen for further study.

EXAMPLE 2

Methods for Esterase Identification and Assay

Esterase Plate assay—Organisms are grown in liquid cultures on TT media at either 55° C. or 65° C. Cells are pelleted by centrifugation (3,000 RPM for 20 minutes) and the supernatants saved to be tested. Pellets are washed with 2 volumes of 10 mM Tris HCl pH 8.0 three times after which the cell pellets are resuspended in fresh Tris buffer and control lanes. Esterases can be identified from Thermus sp. T351 and from several of the new isolates. Table 1 summarizes the activities which are found from these organisms.

TABLE 1

Summary of New Esterases and Strains Identified

| Isolate[1] | Esterase | Source | Growth Temp (° C.) 37 | 55 | 65 | Isolation Temp (° C.) | mw (kD)[2] | Specific Activity[3] |
|---|---|---|---|---|---|---|---|---|
| S1 | E001 | soil | nd | nd | + | 65 | 22 | 0.011 |
| 54 | E002 | compost | − | + | + | 65 | 28 | 0.87 |
| 50 | E003 | compost | − | + | + | 65 | 28 | 2.2 |
| GP1 | E004 | soil | nd | nd | + | 65 | 36 | 0.3 |
| C-1 | E005 | compost | nd | nd | + | 65 | 28 | 2.3 |
| 55 | E006 | compost | − | + | + | 65 | 36 | 2.1 |
| 46 | E007 | compost | − | + | + | 65 | 28 | 0.3 |
| 30 | E008 | soil | − | + | + | 55 | 28 | 2.1 |
| 28 | E009 | soil | − | + | + | 55 | 36 | 2.0 |
| 29 | E010 | soil | − | + | − | 55 | 46.5 | 2.3 |
| 31 | E011 | soil | − | + | − | 55 | 36 | 3.6 |
| 26b | E012 | soil | − | + | − | 55 | 28 | 5.2 |
| 27 | E013 | soil | − | + | + | 55 | 36 | 2.7 |
| 34 | E014 | soil | − | + | +/− | 55 | 36 | 0.8 |
| 62 | E015 | compost | − | + | + | 55 | 36 | 3.4 |
| 47 | E016 | compost | − | + | + | 65 | 28 | 0.8 |
| 49 | E017 | soil | − | + | + | 65 | 36 | 0.03 |
| C-3 | E018 | compost | nd | nd | + | 65 | 36 | 0.077 |
| 4 | E019 | compost | − | + | + | 55 | 30 | 0.4 |
| 7 | E020 | compost | − | + | + | 55 | 28 | 1.6 |
| 32 | E021/17b[4] | soil | − | + | +/− | 55 | 36 | 0.3 |
| Thermus sp. T351 | E100 | ATCC# 31674 | nd | + | + | 65 | 45 | 0.0032 |
| Thermus sp. T351 | E101 | ATCC# 31674 | nd | + | + | 65 | 135 | 0.032 |

[1]Isolates GP1, 27, 28, 29, 30, 31, 32, 34, 62 appear to be thermophilic Actinomyces.
[2]Approximate molecular weight as determined by chromatography for E001–E021 or SDS-PAGE for E100 and E101.
[3]Specific activity is the amount of p-nitrophenol produced in micromoles per minute per milligram of total protein at 40° C. after purification to homogeneity (for E100 and E101) or semi-purification (for E001–E021) as described in the Examples.
[4]E021 is also referred to as E017b.

disrupted by sonication. Cell debris is removed by centrifugation and the crude extracts were tested for esterase activity as are shown in FIG. 1. Both cell extracts and culture supernatants are tested for esterase activity by this method. Only cell extracts showed significant esterase activity.

Esterase Liquid assay and determination of specific activity—Protein concentrations are determined by the Pierce BCA assay using defined concentrations of bovine serum albumin as the standard. Protein concentrations are obtained from the calibrated absorbance of the sample solutions at 562 nm and are expressed as milligrams of protein. Esterase activities are routinely measured by determining the rate of hydrolysis of p-nitrophenylproprionate (0.5 mM from a 10 mM stock dissolved in CH3CN) in 50 mM sodium phosphate buffer pH 7.0 equilibrated at 40° C. and monitored at 346 nm (isosbestic point for the acid/carboxylate couple $\epsilon$=4800). The specific activity is defined as the amount of p-nitrophenol produced in micromoles per minute per milligram of total protein.

Identification of extremely stable esterases.—Native (non denaturing) 10% polyacrylamide gels are run on crude extracts. These gels can then be stained with an esterase activity stain containing either 5-bromo-4-chloro-3-indolyl acetate (X-acetate), 5-bromo-4-chloro-3-indolyl butyrate (X-butyrate) or 5-bromo-4-chloro-3-indolyl caprylate (X-caprylate) and produced indigo precipitates. Two major bands were apparent in the lanes with Thennus crude extracts. A single small band of activity is seen in the E. coli

EXAMPLE 3

Procedure for Purification of Esterase Activity to Homogeneity

Protein Isolation—A large batch cell culture is grown according to the methods described in Example 1 and the cell paste is collected by centrifugation and stored at −80° C. 100 g of cell paste is thawed in 200 ml of a stirred solution composed of 50 mM phosphate buffer at pH 7.5 containing 200 mM KCl and 0.1 mM EDTA. Once dissolved, the suspension is allowed to warm to room temperature and then treated with lysozyme (0.1 mg/ml) for 2 hours. The solution is then sonicated to completely disrupt the cells. Settings used on a 375 watt Sonics & Materials Vibra Cell sonicator with a standard ¼" horn were 5 minutes of power setting 8 disruption with a 50% pulse rate. Alternative methods for cell disruption can include processing the cells through a device such as a french press, Gaullen homogenizer, microfluidizer or other homogenizer. Cell debris is removed by centrifugation and proteins can be precipitated by $NH_4SO_4$ fractionation to 60% saturation. Precipitated protein is centrifuged and resuspended in minimal volume of 50 mM phosphate pH 6.5 containing 1 mM β-mercaptoethanol (BME).

DEAE Purification—The protein solution is dialyzed against the resuspension buffer 3 times using 10 Kd pore size dialysis tubing. The resulting protein solution is diluted two fold in the buffer and applied to a 100 ml bed volume DEAE column equilibrated in the same buffer. The column is washed with 200 ml equilibration buffer and then eluted with a linear gradient from 0 to 0.5M NaCl.

Q Resin purification—Active fractions isolated from DEAE purification are pooled and dialyzed against three changes of equilibration buffer and dialysate was applied to a 50 ml bed volume of sepharose Q resin equilibrated with the buffer above. The column is washed with 100 ml of 50 mM phosphate pH 6.5 containing 0.1M KCl and 1 mM BME and then eluted with 150 ml of a KCl gradient from 0.1M to 0.6M added to the above buffer.

Ultrafiltration Concentration—Active fractions are pooled and concentrated using an Amicon Ultrafiltration system fitted with a 30 Kd cut off membrane.

Preparative SDS PAGE—Concentrated protein solutions are loaded to a preparative 10% SDS-PAGE gel using the standard SDS loading buffer without boiling the sample. After development, the gel is treated with 0.7% agarose containing 0.1M phosphate pH 7.5 and 0.1 mg/ml 5-bromo-4-chloro-indoylacetate. The resulting blue band was excised from the gel, placed in dialysis tubing and the protein is recovered by electroelution in 0.05M Tris buffer pH 8.5 for 1 hour. At this stage the protein is purified to homogeneity as observed by both native- and SDS-PAGE stained with either coomassie or silver stain. Protein can be stored at 4° C. for future use.

Gel filtration—A gel filtration column can also be used as a further or substituted purification step.

EXAMPLE 4

Method for Commercial Grade Preparation of Isolated Esterase

For many industrial applications, a completely purified preparation of enzyme is neither required nor desired due to production cost considerations. A rapid, inexpensive protocol to produce a protein of interest in a form which is isolated to contain protein with significant esterase activity is desired. One such semi-purification procedure is described here. 50 g of cell paste is thawed in 100 ml of 50 mM Tris HCl buffer at pH 7.5 containing 0.1M NaCl and 0.01 mM EDTA. Cells are disrupted by sonication and the cell debris is removed by centrifugation. The crude cell lysate is diluted by three fold with 50 mM Tris-HCl pH 7.5 and the material is loaded to a DEAE cellulose column (bed volume 60 ml) equilibrated with the dilution buffer. The column is washed with three column volumes of dilution buffer followed by a salt gradient of 0–0.5M NaCl over 4 column volumes. Active fractions eluted from the ion exchange resin in the salt gradient window of 0.25–0.35M. Fractions were assayed for activity as described under determination of specific activity and those showing the highest activity were pooled and concentrated by ultrafiltration with 10 Kd molecular weight cut off membrane. Concentrated enzyme samples are stored at 4° C. for further use. In some instances, more than one ester hydrolysis activity may still be detected under long term exposure to substrate agarose overlays of proteins separated on native PAGE, indicating very small quantities of a second esterase activity which should not interfere with most industrial applications. A further purification (such as an Ammonium sulfate salt precipitation, gel filtration, or other methods as described in Example 3) can be applied if necessary. The process can be scaled up or down as desired.

EXAMPLE 5

Method for Determination of Temperature Profile

Optimal temperature profiles for an esterase protein is performed by measuring the activity of the esterase diluted into 0.1M sodium phosphate buffer pH 7.0 equilibrated at 30° C., 35° C., 45° C., 55° C. and 65° C. respectively for five minutes. The temperature profile is then determined by measuring the rate of hydrolysis of p-nitrophenylproprionate added to the equilibrated solution under reaction conditions described for determination of specific activity in Example 2 (modified by the various temperatures used in this experiment). Control reactions that substitute bovine serum albumin for esterase enzymes are used to allow correction for temperature dependent autohydrolysis of the substrate. The data is then plotted as relative activity versus the temperature of the reaction.

EXAMPLE 6

Method for Determination of Enzyme Stability

The long term catalytic stability the esterase enzyme is evaluated by testing the activity remaining after exposure to various temperatures. The enzyme stock solution is diluted into 0.1M sodium phosphate buffer pH 7.0 and placed in a temperature bath equilibrated to 25° C., 40° C. or 60° C. respectively under sealed conditions to avoid concentration effects due to evaporation. Residual activity is then determined by removing aliquots at regular intervals and measuring the rate of hydrolysis of p-nitrophenyl-proprionate as described above. Results are plotted as relative activity vs. time. The results (see FIG. 4) indicate that all enzymes retain most of the initial activity for at least 48 hours when exposed to temperatures up to and including 40° C. Activity does decrease at 60° C. particularly for enzymes isolated from organisms with optimal growth temperatures near 55° C.

EXAMPLE 7

Method for Determination of pH Profile

The pH profile of an esterase is determined as follows. The rate of p-nitrophenylproprionate hydrolysis is determined under reaction conditions similar to those described for determination of specific activity in Example 2 with buffers of wide useful pH windows that overlap with at least one data point. For the purposes of these experiments two buffers were selected that met the above criteria, Mes (useful range of 6–6.5) and Bis-tris propane (useful buffer range 6.5–9). All pH tests were corrected for spontaneous autohydrolysis by subtraction of experimental runs from controls substituting bovine serum albumen for esterase. This control data treatment becomes especially important for pH's greater than 7.5.

EXAMPLE 8

Solvent Effects on Esterase Activity

Industrial applications for biocatalysts often require that enzymes function under non-native and harsh conditions. Exposure to elevated temperatures and pH fluctuations are possible challenges to enzyme activity, however the lack aqueous solubility of many compounds that may serve as substrate targets for biocatalysts is a significant challenge to the industrial organic chemist. Organic cosolvents are commonly used in reactions and isolated enzymes must be able to survive under conditions of relatively high concentrations of cosolvent. Experiments are run in the presence of various organic solvents such as ethanol, acetonitrile, dimethylformamide, dioxane, toluene, hexane and detergents like SDS, triton X100 and Tween 20. Additional experiments are also performed to test the activity of isolated catalysts in nearly anhydrous solvent conditions in which the enzymes will be lyophilized from buffers and pH's of optimal activity.

EXAMPLE 9

Method for Protein Characterization by Migration on Native PAGE

The number of esterase enzymes in each semi-pure sample is determined from native gel PAGE using 4–15% acrylamide gradient (precast gels purchased from Bio-Rad laboratories) separating proteins based on their charge to size ratio. The gel shows trace contamination with other enzymes capable of indoylacetate hydrolysis that could not be detected easily with the HPLC because of column dilution effects. What is clear from the gel experiments is that most of the samples have a single major activity that have similar migration characteristics as shown in FIG. 2.

EXAMPLE 10

Determination of Relative Molecular Weight by Chromatography

The estimated native molecular weights for the protein of interest is determined by separation on a Pharmacia Superdex S200 FPLC column fitted to a Hitachi HPLC 6200 system. Proteins were separated by isocratic elution in 0.05M sodium phosphate buffer at pH 7.0 containing 0.1M NaCl. The solvent flow rate was maintained at 0.5 ml/min and protein was detected by UV at 280 nm. Esterase active fractions were detected initially by 5-bromo-3-chloro-3-indolyl-acetate plate assay with follow-up assay of most active fractions by p-nitrophenyl-proprionate hydrolysis (both methods are described in Example 2). Molecular weights are estimated by comparison to standard elution profiles (plotted as the log of molecular weight vs. time in minutes) generated by use of the following proteins: β-amylase 200 Kd, alcohol dehydrogenase 150 Kd, bovine serum albumin 66 Kd, carbonic anhydrase 29 Kd, cytochrome c 12.3 Kd.

EXAMPLE 11

Characterization of Substrate Specificities

Substrate preference of esterases for hydrolytic activity on various esters can be determined as follows. A grid of molecules is prepared on microtiter plates by dissolving each substrate (0.1 mM final concentration) in $CH_3CN$ and mixing with 0.1M phosphate buffer pH 7.5. Partially purified enzymes is then added to the wells and the reaction mixture is incubated for 30 minutes. Crude lysates can also be tested this way. Plates are checked after 10, 20 and 30 minutes to determine relative activities. For experiments with noncolored substrates, reactions are run in test tubes under the same conditions as described for the colored substrates except that the reactions are extracted three times with dichloromethane. The organic layers are combined, dried with $MgSO_4$ and concentrated to 0.1 ml in a nitrogen stream. The concentrates are then spotted to silica gel TLC plates and developed in a solvent mixture of 80:20:0.01 hexane:ethyl ether:acetic acid. TLC plates are visualized with UV and $I_2$.

EXAMPLE 12

Rapid Screen Assay for Quick Substrate Specificity Characterization

A new method was developed to rapidly screen for esterase activity based on the mechanism of the enzyme catalyzed hydrolysis reaction wherein the pH of the system is reduced by the release of protons upon ester hydrolysis. The proton flux in the reaction can be monitored by use of indicator dyes that have pH-dependent color transitions in the desired pH range of enzyme activity. The best indicators tested are phenol red for enzymes that function optimally at slightly elevated pHs (starting point pH 8.5) or bromothymol blue (starting point pH 7.2) for enzymes that operate well at more neutral conditions.

The indicator reactions are monitored by one of two methods. Spectroscopic studies are performed by measuring the UV/Vis maxima of a 0.001% solution of either phenol red or bromothymol blue dissolved in different pH buffers at 5 mM concentration. Hydrolytic reactions are then performed by adding the substrate (0.1 mM final concentration) to a 5 mM buffer solution (sodium phosphate pH 7.2 for bromothymol blue indicator and sodium borate pH 8.5 for phenol red indicator) and equilibrating the temperature at 25° C. for five minutes followed by initiation of the reaction by addition of 0.1 U target enzyme.

An alternative method for monitoring the hydrolytic reactions is useful for broad screening applications. 5 mM buffer containing 0.001% indicator dye and substrates dissolved in $CH_3CN$, DMF or DMSO to an organic solvent composition of no more than 10% is added to a stirred 24 well microtiter tray. The temperature is allowed to equilibrate for five minutes at 25° C. after which the reaction is initiated by addition of 0.1 U of the esterase. Reaction progress is monitored by solution color changes upon which, aliquots of NaOH are added to return the reaction color to the starting point. Reactions are determined to be complete when no further color change is detected after prolonged incubation. Product formation is verified by TLC analysis of reactions acidified with 0.1M HCl, extracted with ethyl acetate, dried with $Na2SO_4$ and concentrated under a stream of $N_2$. For testing substrates in which enzyme-based chiral resolution is being screened, products are separated and isolated by chiral phase HPLC and enantiomeric purity is determined by integration of peak areas for each isomer.

Rapid assay of a variety of hydrolytic activities, in this cases esterases, is determined in a microtiter plate experiment using several different enzymes and substrates. Accurate comparison of commercially available enzymes can be insured by using the same specific activity for each enzyme determined from the total protein and the initial rate of hydrolysis of the common substrate p-nitrophenylproprionate. The data are recorded as the time required to visualize a pH dependent color change for the given indicator dye. Control experiments using BSA as the protein source cause no change in indicator color and establish that pH changes in solution are the result of an enzyme catalyzed hydrolysis. Control tests of reaction solutions containing enzymes and indicators without substrates established that color changes in the solutions are not the result of buffer salts or the enzymes alone.

Studies performed to determine whether the microtiter plate format was amenable to small scale preparative chemistry are performed as follows. Using racemic phenethylacetate and pig liver esterase, reactions are run and titrated with aliquots of 0.1N NaOH to maintain original solution color until no further color changes occurred at which point the reactions are stopped. Products are isolated and tested by TLC and compared to total amount of base added to verify the extent of the reaction. Phenethyl alcohol is separated from starting acetyl ester by flash column chromatography followed by analysis by chiral phase HPLC. The enantiomeric excess of the hydrolysis products is determined from the peak integration and compared to an identical reaction run in the absence of indicator dye. The results from these experiments suggest that inclusion of indicator dye has no effect on the stereoselectivity of esterase catalyzed resolution of phenethylacetate.

In order to test the assay for usefulness in a broad-based enzyme screening method, seven organisms isolated from various sources in the environment were tested for their ability to produce enzymes that would catalyze the hydrolysis of a group of structurally diverse compounds. Table 2 shows the results of these studies.

have been chosen specifically because of their importance as intermediates in the synthetic literature with the potential for industrial application. Experiments can be performed with crude lysates or proteins isolated from media broth in cases where the activities are known to rapidly assess the likely reaction chemistry including substrate preference and stereochemistry. All structure activity tests are compared to standard mesophile biocatalysts such as pig liver esterase. The reactions are monitored by TLC analysis to compare the products to standards purchased from commercial sources or prepared by chemical means (for example, base-catalyzed hydrolysis of esters).

TABLE 2

Substrate Specificity.

| Substrate | Lysate Hydrolytic Rate (min) | | | | | | | | |
|---|---|---|---|---|---|---|---|---|---|
| | N/E | E001 | E003 | E004 | E005 | E006 | E016 | E017 | E018 |
| (ethyl butyrate) | — | 60 | 240 | 20 | <5 | <5 | — | — | 15 |
| (glycerol tributyrate) | — | 60 | 20 | <5 | <5 | <5 | <5 | 120 | 60 |
| (R)-methyl mandelate | — | — | 240 | — | 120 | 240 | — | 300 | — |
| (S)-methyl mandelate | — | — | 300 | 240 | 240 | 240 | — | — | 240 |
| (±)-phenethyl acetate | — | 240 | 240 | 20 | 60 | 60 | 120 | 900 | 60 |
| Solvent Control | — | — | — | — | — | — | — | — | — |

Results are reported as the amount of time required to change indicator color. The data is indicative of variable substrate specificity between different environmental isolates. Of particular note is the suggestion of stereoselectivity as determined from the relative rates of hydrolysis for substrate enantiomers. Control reactions are similar to those described above in the substrate specificity studies with commercially available enzymes.

EXAMPLE 13

Further Characterization of Substrate Specificities

Depicted in FIG. 10 are examples of the substrates that can be tested with each enzyme activity. These molecules Investigations of stereochemical preference by each esterase can be evaluated by one of two methods. In the first method, standard single stereoisomers of commercially available entantiomerically pure substrate esters are hydrolyzed by each enzyme and the relative rates of hydrolysis for each antipode are used as diagnostic qualitative determinants of potential chiral selectivity. In the second method, those molecules not commercially available as single stereoisomers are hydrolyzed as racemates using kinetic resolution methods (running the reaction generally less than 50% completion). The products of the reaction are isolated and analyzed for their enantiomeric excess (ee) by chiral phase HPLC (Diacel Chiralcel OD or OB) or $^1$H NMR of the corresponding diasteriomers prepared by derivatizing products to Mosher derivatives (alcohol products) or menthyl derivatives (carboxylate products). Diastereomeric ratios determined from the NMR spectra are based on corresponding peak integrations and compared to either literature values or standards obtained from commercial sources using of chiral shift reagents when necessary. Optical rotations and absolute configurations of the products are then determined by polarimetric analysis and compared to values found in the literature or determined from standards obtained from commercial suppliers.

EXAMPLE 14

Characterization of Proteins E001–E021/17b

Strains from the identified sources as listed in Table 1 were isolated by growth in TT media at 65° C. as described in Example 1 (ie. S1 from soil, etc.). Specific esterase hydrolytic activity was identified by the methods described in Example 2 and the isolated esterase protein assigned the identifier as listed in Table 1 (ie. E001 etc.) To prepare enzyme, a 15 liter culture of isolate is grown and the cells are spun down and collected as described in Example 1. The cells are lysed and a isolated preparation of was purified according to the procedures outlined in Example 4. The protein was characterized using the methods described in Example 5 to determine the temperature profile, Example 6 to determine protein stability, and Example 7 to determine the pH profile, and the results are shown in FIG. 4. The protein was characterized by migration on Native gradient PAGE as described in Example 9 and the data is shown in FIG. 2. The specific activity was determined as described in Example 2 and the molecular weight was determined by chromatography as described in Example 10 and are presented in Table 1. Substrate specificity for several proteins has been demonstrated and are shown in Table 2. Thus the identified and characterized esterases have been demonstrated to be useful, and to posesses unique activity at commercially useful purity. Certain results are summarized in Table 10.

EXAMPLE 15

Characterization of E100

Purification of E100—E100 is purified from Thermus sp. T351 over 300 fold by a series of four steps described in Example 3: DEAE purification, Q Resin purification, Ultrafiltration concentration, and preparative SDS PAGE. The specific activity could not be measured in the crude lysate since there was a secondary esterase activity present (E101). The secondary activity could be completely removed from the target esterase during the first chromatographic step in which the secondary esterase passed through the DEAE column unbound. For purification of various technical grades of E100, DEAE purification alone is sufficient to yield E100 enzyme substantially purified away from any other contaminating activity. Q Resin purification and ultrafiltration allow for higher purity product to be produced as required by specific applications. A final SDS PAGE purification step allows the protein to be purified to homogeneity for determination of molecular characteristics.

Figure 5:
FIG. 5. Migration profile of E100 on 8% SDS-PAGE. Lane 1. Boiled E100 following DEAE and Q Sepharose chromatography. Lane 2. Nonboiled purified E100. Lane 3. Boiled E100. Lane 4. Molecular weight markers.

Protein Characterization—The active band is collected by electroelution on a preparative SDS-PAGE gel and rerun on 10% SDS-PAGE under denaturing conditions. This shows a single band with a relative molecular mass of about ~45 Kd (FIG. 5). Unboiled samples run on the same SDS-PAGE gels show multiple bands in approximate increments of the proposed monomeric molecular mass. Additionally, the non-boiled sample can be stained for activity, however only bands corresponding to multimeric forms of the enzyme are found to retain activity beginning with dimeric species. The specific activity of the purified protein is approximately $3.2 \times 10^{-6}$ Mmin$^{-1}$mg$^{-1}$ using 4-methyl-umbelliferyl-butyrate (MUB) as the substrate.

Measurement of E100 Enzyme Activity—Esterase activity is measured by monitoring the hydrolysis of p-nitrophenylproprionate (pNP), or in some cases MUB. Each substrate is dissolved in acetonitrile and added to the reaction mixture (100 µM final concentration) which contain 50 mM Tris HCl pH 8.5 adjusted for temperature dependent pH variation. Reactions are thermally equilibrated at 37° C. for 5 minutes prior to initiation of the reaction by addition of 10 µL of enzyme sample, while control reactions substituted equivalent amounts of BSA. The reaction is monitored spectrophotometrically at 405 nm ϵ=17 mM$^{-1}$cm$^{-1}$ for pNP and 360 nm ϵ=7.9 mM$^{-1}$ cm$^{-1}$ for MUB.

The rates of enzyme catalyzed hydrolysis are corrected for the spontaneous hydrolysis of the substrate. Protein concentrations are determined by either the absorbance at 280 nm or by Lowery assay. Crude activity is determined by a colorimetric assay based on the hydrolysis of 5-bromo-4-chloro-3-indoyl esters suspended in a 0.7% agar matrix on microtiter plates. A 0.1 mg/ml solution of the indolyl derivative is dissolved in a minimal volume of acetonitrile and added to a warm solution of 0.7% agar containing 0.1M phosphate buffer pH 7.5. 10 µL of this solution is distributed to microtiter plates which, when cooled, could be used with as much as 100 µL of enzyme sample and incubated at temperatures from ambient to >65° C.

E100 was effectively inhibited when exposed to tosyl fluoride but was unaffected by the presence of either metal ions, chelating agents or reducing molecules Table 3.

TABLE 3

Inhibition by reaction components on the hydrolysis of p-nitrophenylprorionate by E100.

| Additive (concentration) | Relative Rate[a] (%) |
|---|---|
| None | 100 |
| PMSF (0.1 mM) | 0 |
| BME (10 mM) | 99 |
| DTT(1 mM) | 101 |
| CaCl$_2$(10 mM) | 108 |
| MgCl$_2$(10 mM) | 95 |
| ZnCl$_2$(10 mM) | 90 |
| EDTA(1 mM) | 96 |

Reaction conditions are those described in the general experimental above except for the additon of specified components. Relative rates are corrected for the spontaneous rate of hydrolysis of the uncatalyzed reaction.

Substrate specificity of E100—The substrate specificity was tested as outlined as according to Example 11, and the results from the structure activity experiments for E100 are shown in summary Table 4. E100 displays a broad substrate specificity catalyzing the hydrolysis of a number of nitrophenyl, coumaryl and alkyl esters. The enzyme displays hydrolytic activity towards both straight chain and aromatic moieties on the carboxylate side of substrates however, carboxylate R groups of long alkyl chains >C8 or those containing naphthyl leaving groups are not substrates. The enzyme displays no significant activity towards either casein or milk as assayed by clearing zones on agar plates.

TABLE 4

Substrate Activity of E100

| Substrate | E100 | Control |
|---|---|---|
| I-acetate[a] | ++ | − |
| I-butyrate[a] | ++ | −− |
| I-caprylate[a] | + | −− |
| N-acetate[a] | −− | −− |
| U-acetate[a] | ++ | +/− |
| U-stearate[a] | −− | −− |
| pN-acetate[a] | ++ | −− |
| pN-proprionate[a] | ++ | −− |
| oN-proprionate[a] | ++ | −− |
| oN-caprylate[a] | + | − |
| oN-palmitate[a] | +− | − |
| oN-stearate[a] | − | −− |
| Me-PA[b] | + | −− |
| Et-PA[b] | + | −− |
| isoProp-PA[b] | + | −− |

Structure activity assay of partially purified esterase E100 from Thermus species. (++) highest activity as determined by (a) color formation in less then 10 min or significant product formation on (b) TLC. The remaining activity measurements follow the order: + > +/− > − > −−. Structure abbreviations are as follows: I, chloro-bromo-indoyl, N, a-napthyl, U, methylumbelliferyl, pN, p-nitrophenyl, oN, o-nitrophenyl, PA, phenylacetate.

Determination of Kinetic Characteristics—Kinetic characteristics are determined by measuring the concentration dependent initial rates of enzyme catalyzed hydrolysis of nitrophenyl proprionate. Reactions are run at pH 8.5 in 50 mM Tris-HCl buffer equilibrated to 37° C. and initiated by addition of enzyme. Rates are determined from the absorbance changes due to formation of product nitrophenol at 405 nm. Rates are corrected for the spontaneous hydrolysis of substrate during the course of the reaction. Concentration vs. rate data are analyzed by both double reciprocal plots and by HanesWolff plots to determine Km, Vmax and Vmax/Km. The kinetic characteristics of E100 determined from plots of the initial rates of hydrolytic reactions are shown in FIG. 6.

Determination of Temperature Profile and Optimal pH for E100—The temperature profile of the enzyme is determined as shown in FIG. 7a. Enzyme activity is observed to steadily increase to the limit of the assay, over 70° C., (where the background signal from autohydrolysis of the substrate became too high and is no longer correctable) as the temperature of the reaction is elevated and suggests that the low end for optimal activity for E100 is greater than 70° C. E100 displays a basic pH profile with a low end optimal activity observed to be approximately 9.0, the limit of substrate stability at 37° C. (FIG. 7b).

Figure 8:
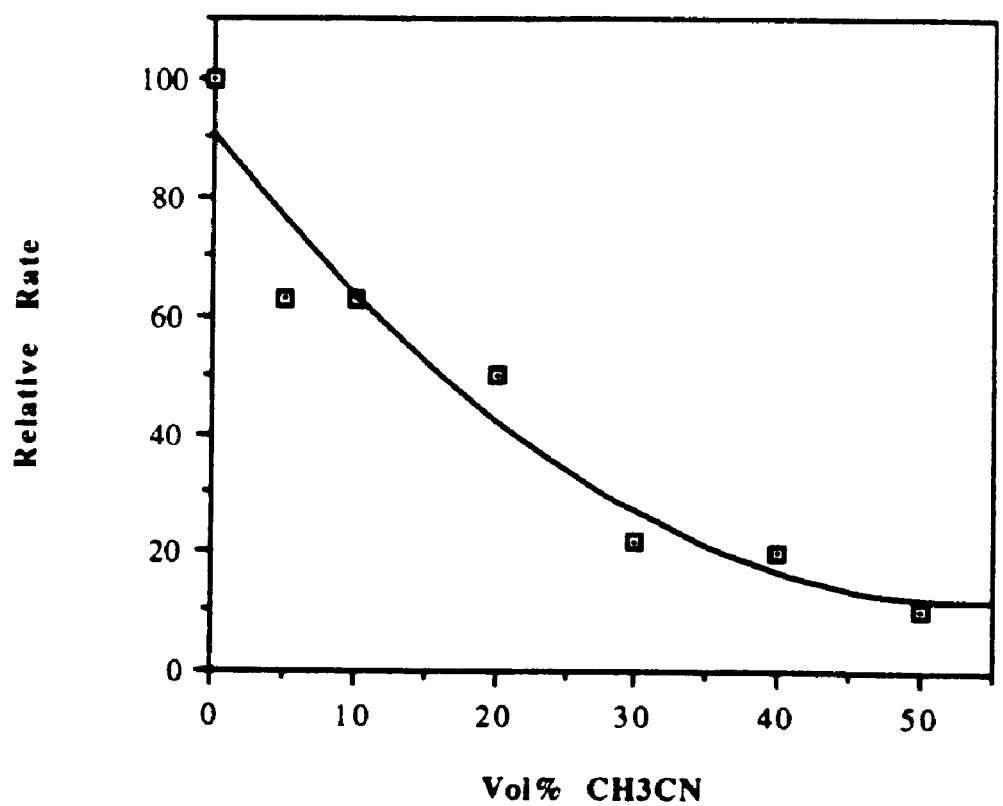
FIG. 8. The tolerance of E100 to the presence of organic cosolvents on the hydrolysis of p-nitrophenyl proprionate as determined by relative rates. Residual activity of the enzyme is determined in the presence of organic solvent by measuring the initial rate of enzyme catalyzed hydrolysis of pNP in the presence of various concentrations of CH$_3$CN. Reactions are run in 50 mM Tris-HCl pH 8.5 at 37° C. as described in determination of activity. Changes in absorbance are corrected for spontaneous hydrolysis of the substrate and the changes in extinction coefficient of the product in the presence of organic cosolvent.
Figure 15A:
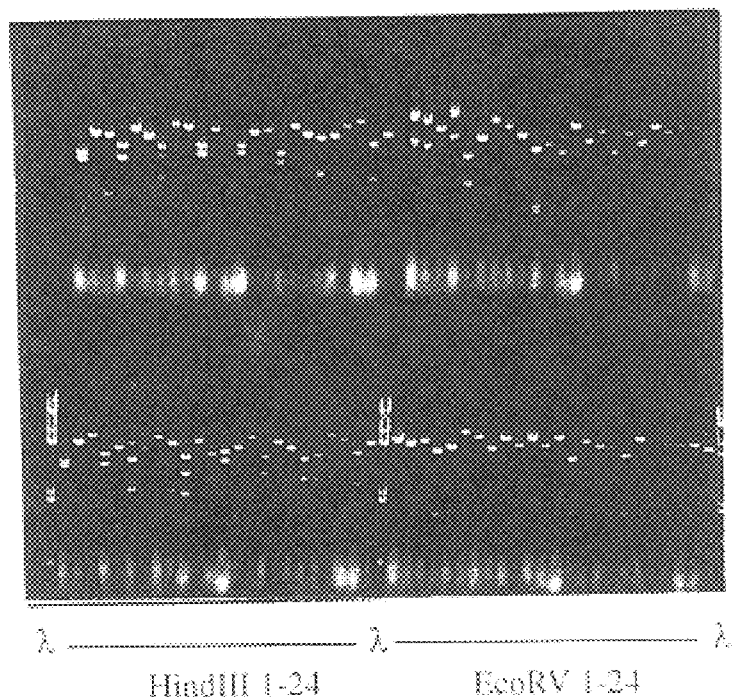
FIG. 15. Digestion patterns for 24 recombinant esterases. The restriction endonuclease digestion patterns for the set of 24 plasmid listed in Table 8 is shown. (a) The 24 plasmids are cut by EcoRI (1–24), BamHI (25–48), HindIII (49–72) and EcoRV(73–96). (b). A gel showing the PstI digestion pattern for plasmids 1–18. (c). A gel showing the PstI digestion patterns for plasmids 19–24 and the XbaI digestion patterns for plasmids 1–11. (d). A gel showing the XbaI digestion patterns for plasmids 12–24. For all gels, lanes 1–24 refer to the following plasmids in the following order: pTGE1.1, pTGE2.1, pTGE2.2, pTGE3.2, pTGE4.6, pTGE5.3, pTGE6.3, pTGE7.1, pTGE8.5, pTGE9.4, pTGE10.3, pTGE11.10, pTGE12.2, pTGE13.2, pTGE14.3, pTGE14.6, pTGE15.9, pTGE16.1, pTGE19.4, pTGE20.4, pTGE21.8, pTGE21.8x, pTGE20.3, pTGE16.3. Plasmid pTGE21.8x is a variant of pTGE21.8 which was isolated that had a loss in activity.
Figure 15B:
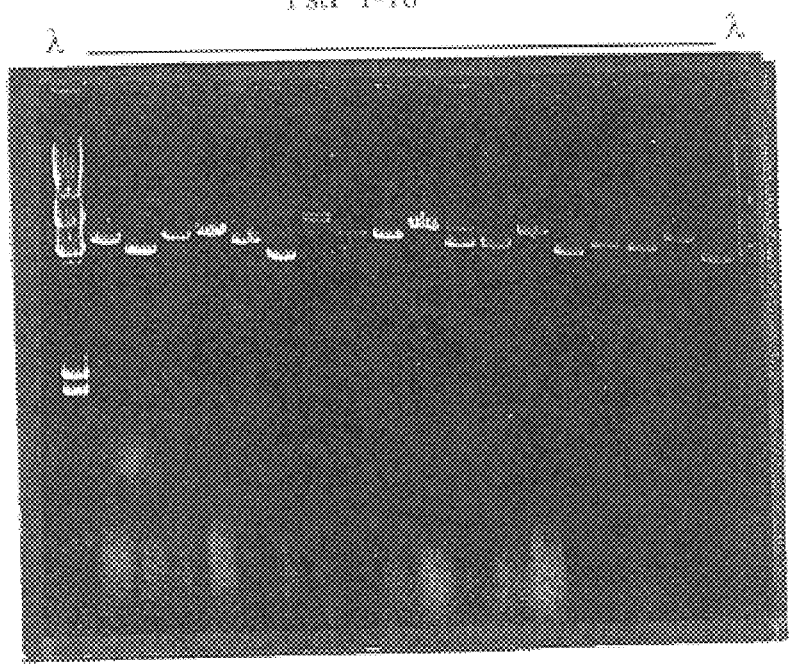
Figure 15C:
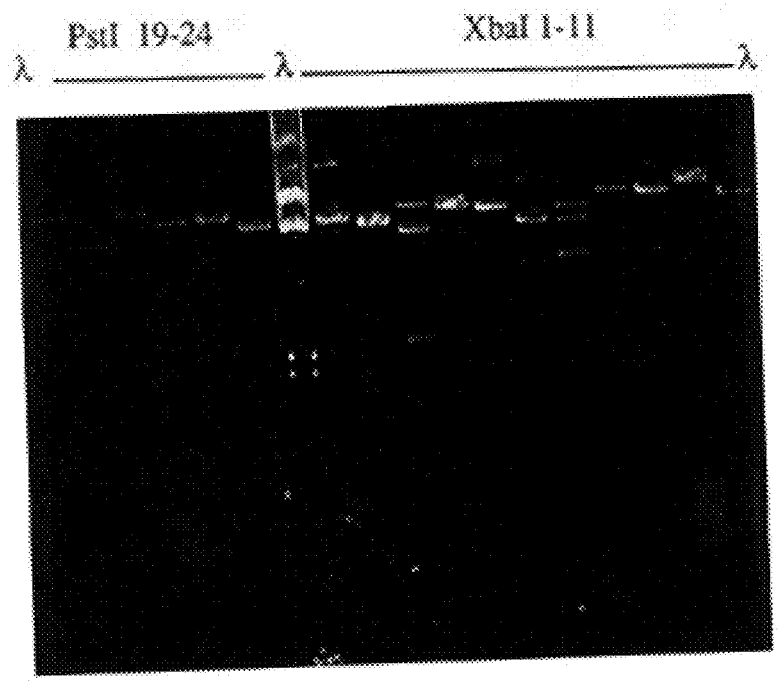
Figure 15D:
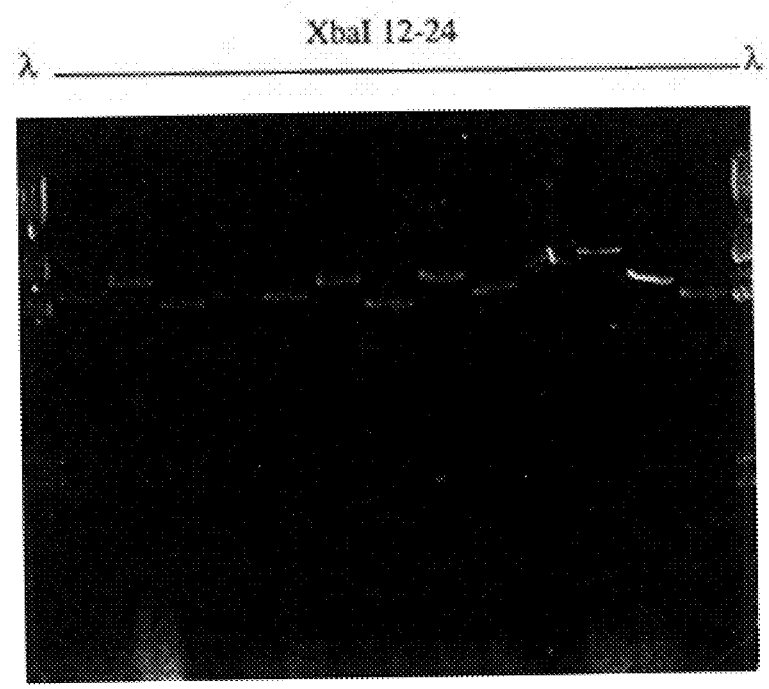

Determination of Enzyme Stability in the Presence of Organic Solvents—E100 is tested for tolerance to organic solvent composition using the polar aprotic cosolvent acetonitrile as a preliminary system. the enzyme retained 50% of its activity in a solvent mixture of 20 vol % organic cosolvent (FIG. 8).

N-Terminal Sequencing of E100—Purified proteins are run on 10% SDS-PAGE gels and then transferred to PVDF membranes by electroblotting. Membranes are washed with several changes of doubly distilled water to remove any remaining SDS or other contaminants and then stained with coomassie blue. Membranes were then destained with several changes of 50:40:10 MeOH:H$_2$0:AcOH followed by one wash of 10% MeOH. Membranes are then air dried and then submitted for sequencing. The N-terminal sequence of E100 was determined at the University of Illinois Urbana Champaign genetic engineering facility.

The N-terminus of E100 was determined by automated sequencing of the polypeptide purified by 10% SDS-PAGE and transferred to a PVDF support. The sequence obtained was: MKLLEWLK?EV, where the letters refer to the standard amino acid single letter code and the "?" refers to an indeterminate amino acid. Thus, E100 has been demonstrated to be a useful esterase with unique activity at commercially useful purity.

EXAMPLE 16

Characterization of E101

E101 is one of two esterase activities that are isolated from Thermus sp T351. E101 can be purified away from a second esterase, E100, in an early purification step.

Purification of E101—A Thermus sp. T351 supernatant prepared as described in Examples 1 and 2 is fractionated with NH$_4$SO$_4$ and the precipitated proteins are collected between 20–60% saturation. Pellets are redissolved in 30 ml of buffer (50 mM Tris-HCl pH 8.0, 1 mM BME) and dialyzed against the same buffer using 30 Kd cutoff dialysis tubing. Dialysate is loaded to 100 ml bed volume of DEAE resin equilibrated with the buffer above and the column was washed with 150 ml of the equilibration buffer. Active protein is observed in the load and wash fractions, pooled, and concentrated with the use of an Amicon concentrator fitted with a YM30 membrane. Concentrated proteins are then loaded directly to a 25 ml bed volume of sepharose SP resin equilibrated with the above buffer. Active fractions appear in the load and wash fractions which are pooled and concentrated as above. Concentrate is then loaded to a Sephracryl HR200 gel filtration column (1×40 cm) and 0.5 ml fractions are collected at a flow rate of 2 ml/hr. Active fractions are collected and analyzed by SDS-PAGE. In order to perform N-terminal sequencing, fractions considered to be homogeneous are concentrated and submitted to a protein sequencing service center. The enzyme is stored at 4° C. for future use.

E101 can be purified over 35 fold by these methods and possesses characteristics dramatically different from E100, the other esterase which is isolated from this strain. Attempts to use ion exchange chromatography result in subtractive purification since in no instance was the protein retained. Resins investigated include DEAE, Q sepharose, CM cellulose, SP sepharose and hydroxyappatite under conditions that varied from pH 6.0 to 9.0, and buffers from phosphate to borate including Tris and Hepes. After two ion exchange steps the protein is purified to homogeneity by gel filtration chromatography however, the protein appears to have an interaction with the column as retention is considerably longer than the molecular weight would suggest. The molecular weight of the protein appears to be approximately 135 Kd with a monomer mass of ~35 Kd as determined from native and denaturing SDS-PAGE respectively (FIG. 9).

E101 Characteristics—The specific activity of the enzyme is ten fold greater than observed for E100 with 4-methyl-umbelliferyl butyrate (MUB) as the substrate. E101 is inhibited by PMSF but is insensitive to metal ions or metal ion chelators. The specific activity of the purified protein was found to be $3.2 \times 10^{-5}$ mol min$^{-1}$mg$^{-1}$ and was determined from initial rates of hydrolysis using methyl umbelliferyl butyrate as a substrate. Table 5 outlines the inhibitory effect of various substances on E101 activity.

TABLE 5

The inhibitory effect of reaction components on the hydrolysis of p-nitrophenylprorionate by E101.

| Additive (concentration) | Relative Rate[a] |
|---|---|
| None | 100% |
| PMSF (0.1 mM) | 0 |
| BME (10 mM) | 96 |
| DTT (1 mM) | 98 |
| $CaCl_2$ (10 mM) | 102 |
| $MgCl_2$ (10 mM) | 97 |
| $ZnCl_2$ (10 mM) | 100 |
| EDTA (1 mM) | 93 |

Reaction conditions are those described in the general experimental above except for the additon of specified components. Relative rates are corrected for the spontaneous rate of hydrolysis of the uncatalyzed reaction.

Substrate specificity of E101—The substrate specificity of E101 was determined as described in Example 11. The results from the structure activity experiments for E101 are shown in Table 6. The hydrolytic activity of the enzyme is similar to that observed for E100 and has no observable protease activity toward milk or casein.

TABLE 6

Substrate Activity of E101

| Substrate | E101 | Control |
|---|---|---|
| I-acetate[a] | ++ | − |
| I-butyrate[a] | ++ | −− |
| I-caprylate[a] | + | −− |
| N-acetate[a] | −− | −− |
| U-acetate[a] | ++ | +/− |
| U-stearate[a] | +/− | −− |
| pN-acetate[a] | + | −− |
| pN-proprionate[a] | + | −− |
| oN-proprionate[a] | ++ | −− |
| oN-caprylate[a] | +/− | − |
| oN-palmitate[a] | +/− | − |
| oN-stearate[a] | − | −− |
| Me-PA[b] | ++ | −− |
| Et-PA[b] | ++ | −− |
| isoProp-PA[b] | + | −− |

Structure activity assay of partially purified esterase E101 from Thermus species. (++) highest activity as determined by (a) color formation in less then 10 min or significant product formation on (b) TLC. The remaining activity measurements follow the order: + > +/− > − > −−. Structure abbreviations are as follows: I, chloro-bromo-indoyl, N, a-napthyl, U, methylumbelliferyl, pN, p-nitrophenyl, oN, o-nitrophenyl, PA, phenylacetate.

Thus, E101 has been demonstrated to be a useful esterase with unique activity at commercially useful purity.

EXAMPLE 17

Cloning of Esterase

General Cloning Strategy—The λZAP cloning system from Stratagene™ can be used for the library constructions and detection of esterase activity. Other cloning systems can also be used to yield similar results. The usual efficiency of cloning in λ vectors vary from $10^5$ to $10^7$ hybrid clones per mg of cloned DNA and is sufficient to produce a representative gene library from a convenient amount of size-selected chromosomal DNA fragments. We have found that detection of esterase activity in phage plaques, as opposed to bacterial colonies, is more efficient due to the easier access of substrate to the enzyme. Phages are generally less sensitive to the toxic action of cloned proteins and are also able to survive at the temperatures up to 70° C. The ability of the cloning system to tolerate elevated temperatures and potential toxicity of the cloned proteins is necessary for the detection of the activity of thermophilic proteins, such as the esterases described here.

Isolation of DNA for Construction of gene banks—Genomic DNA is prepared from a culture of the appropriate strain containing the esterase of interest as described in Example 1. Cells of different strains are grown to late log phase in 100 ml TT broth (8 g Polypeptone (BBL 11910), 4 g yeast extract, 2 g NaCl, per liter) at 55° C. or 65° C. overnight shaking at 250 RPM. Cells are recovered by centrifugation and the pellet is resuspended in 5 ml of lysis buffer (10 mM Tris-HCL, pH 7.0, 1 mM EDTA, and 10 mM NaCl). Lysozyme is added to a final concentration of 2 mg/ml. Cells are incubated at 37° C. for 15 minutes followed by the addition of SDS to 1%. The lysate is gently extracted three times with phenol/chloroform/iso-amyl alcohol (25/24/1) and the DNA spooled from a 95% ethanol overlay of the aqueous phase.

One of ordinary skill would find other methods for preparation of DNA which are well known in the art (37). For example, fresh colonies of a strain containing the esterase of interest are inoculated in 50 ml of TT media in 250 ml Erlenmeyer flask and incubated at 55° C. for 24 hours at 200 rpm in a New Brunswick Environmental Shaker. The cells are harvested by centrifugation at 3000 g for 15 min., resuspended in 5 ml of GTE buffer (50 mM Glucose, 25 mM Tris-HCl pH 8, 10 mM EDTA) and treated with 2 mg/ml of lysozyme at 37° C. for 10 min. Lysozyme-generated spheroplasts are lysed by the addition of 1% SDS and partially deproteinased by addition of 100 μg/ml of proteinase K at 24° C. for 10 min. Chromosomal DNA is further purified by three phenol/chloroform extractions, precipitated with 2.5 volumes of ethanol and resuspended in 1 ml of TE (10 mM Tris pH 8.0; 1 mM EDTA), after washing in 20 ml of 75% ethanol. The extracted fraction consists of DNA fragments larger than 50 kb, with a concentration of about 0.5 ng/μl, as detected by gel electrophoresis using a 0.7% agarose gel run at 10 V/cm for 4 hours.

Construction of Gene Libraries—Genomic DNA is partially digested with the restriction enzyme Sau3A and then ligated to predigested Lambda ZAP Express (Stratagene Cloning Systems). Products of ligation reactions are packed in vitro using λ packaging extracts which are purchased from Promega. This vector accommodates DNA up to 12 kb in length and allows identification of clones both by expression off the T3 and T7 promoters and by probe hybridization to plaques. The library is retained and screened for esterase activity. Other methods for generating genomic DNA libraries are also well known in the art.

Five samples of 10 μg of chromosomal DNA of each of the strains prepared as described above, are treated with different concentrations of Sau3A restriction endonuclease (New England BioLabs) according to the manufacturer's instructions for 30 min at 37° C. in a volume of 50 μl each. The concentration of Sau3A is varied from 0.1 u to 0.002 μ/μg of the digested DNA in separate tubes. The reactions are stopped by heat inactivation of the endonuclease at 70° C. for 10 minutes and analyzed by gel electrophoresis on a 0.7% agarose gel run at 10 V/cm for 4 hours (a typical digestion pattern is obtained, data not shown). Fractions with an average fragment size of 5 kb are chosen for cloning. For native strains containing E001, E002, E003, E006, E007, E008, E009, E010, E012, E016, E020 these are the second of the five samples of digested chromosomal DNA with the concentration of Sau3A of about 0.02 μ/μg of the DNA. For the rest of the strains, the proper degree of partial digestion is achieved in the first test tube with 0.1 u of Sau3A/μg of the DNA. Fifty ng of chromosomal DNA fragments are ligated with equimolar amounts of dephosphorilatyed BamHI-arms of the lambda ZAP phage vector (Stratagene) in 5 μl with 1 unit of ligase (New England Biolabs). Ligation reactions are performed at 18° C. for 8 hours and stopped by heat inactivation at 70° C. for 10 min. One μl of the ligation reaction, containing approximately 10 ng of DNA insert, is used for in vitro packaging with 10 μl of lambda proheads (produced by Promega Corp). The packaging reaction is performed at 28° C. for 90 min, combined with 100 μl of an overnight culture of E. coli XL1 Blue and plated using 2 ml of 0.7% top agar (0.8%NaCl, 10 mM MgSO4) per plate onto five 90-mm Petri plates containing LB media. Serial dilutions of the packaging mixture are produced in order to determine the cloning efficiency which is generally about $1.0 \times 10^7$ hybrid phages/μg of cloned DNA. Cloning efficiencies for each individual strain varied, the size of the library generated fell within a range of 0.5 to $2.5 \times 10^5$ from which two to twelve positive clones were analyzed (data not shown). Hybrid phages from one plate are harvested to collect the amplified library, which is stored in 3 ml of LB media with 25% glycerol. The four other primary plates are treated with indicator agar containing 5-bromo-4-chloro-3-indolyl-acetate (X-Acetate) as described below, to find hybrid plaques carrying esterase genes.

Screening of gene banks for esterase activity—The products of the above packaging reactions are infected into *E. coli* XL1 blue MRF' (Stratagene). Primary plaques of an unamplified gene library are screened for enzyme activity by overlaying the plates with top agar containing X-Acetate for 30 minutes at 65° C. The concentration of substrate in the indicator overlay is diluted from a 4% stock in ethanol or N,N-dimethyl formamide to a concentration generally between 0.1 and 1% (usually about 0.4% is used) in the final solution. Other suitable substrates may be substituted in this procedure including, but not limited to, 5-bromo-4-chloro-3-indolyl-butyrate (X-butyrate), 5-bromo-4-chloro-3-indolyl-proprionate (X-proprionate), 5-bromo-4-chloro-3-indolyl-stearate (X-stearate), 4-methylumbelliferyl-acetate (MUA), 4-methylumbelliferyl-butyrate (MUB), 4-methylumbelliferyl-proprionate (MUP), or other 5-bromo-4-chloro-3-indolyl- or 4-methylumbelliferyl-esters which may be either synthesized or purchased from a commercial vendor such as Sigma Chemical. In order to inactivate background endogenous esterase activity from *E. coli*, the plates are preheated at 65° C. for 20 minutes. Hybrid phages surviving this procedure are picked and re-screened three times. The extracts are then analyzed for the presence of a protein band with the same mobility as the native protein as described below. The lambda ZAP cloning system permits an excision of smaller plasmid vector to simplify the insert characterization. While other methods may be employed for screening gene banks for esterase activity, i.e. isolation, purification, and N-terminal sequencing of protein; creation of degenerate nucleotide probes from N-terminal sequence; screening of gene bank with degenerate probes, the instant method is efficient and uniquely suited for the purpose of isolation of promising clones.

In particular, the four primary plates with phage colonies generated during the cloning described above, are incubated at 65° C. for 30 min. in order to inactivate some of the potential *E. coli* esterase activities. Approximately two ml of 0.7% top agar (0.8% NaCl, 10 mM MgSO$_4$) containing about 1 mg/ml of the colorimetric esterase substrate X-Acetate or other substrate (including but not limited to X-butyrate, X-proprionate, X-stearate, and 4-methylumbelliferyl based substrates) is overlaid onto each plate. Expression of cloned esterases can be detected by blue halos around phage colonies (or fluorescent halos in the case of the 4-methylumbelliferyl substates). As an example, the expression pattern observed for the gene library from strain isolate 28 (E009) is depicted in FIG. 11a. A typical result for this process can yield a ratio of 1:3000 positive colonies to hybrid phages.

Between two and twelve primary positive phage plaques are generally picked up from each set of plates, resuspended in 50 μl of LB medium, and streaked onto a lawn of *E. coli* XL1 Blue using sterile paper strips. These purified phage plaques are then overlaid by indicator agar containing X-Acetate as before, and positive plaques were selected as in primary screening experiment. An example of this restreaking is shown in FIG. 11b. Three rounds of such purification are generally sufficient to produce a pure hybrid phage clone expressing esterase activity. All these clone candidates demonstrate significant esterase activity in the X-Acetate plate assay. Several clone candidates from each strain are chosen for further analysis, each representing the progeny of single primary phage plaque.

Testing Protein Profiles Produced by Phage Clones—Production and analysis of protein from the phage clones is performed as follows, but alternative methods are possible: A single plaque from each clone is resuspended in 20 μl of an overnight culture of *E. coli* XL1 Blue (grown in LB medium with the presence of 10 mM of MgSO$_4$), incubated for 20 min at 24° C. in one well of a 96-well microtiter plate to allow adsorption, transferred into 15-ml test tube containing 2 ml of LB, and grown overnight at 37° C. in a New Brunswick Environmental Shaking incubator set at approximately 300 rpm. Cell debris can be removed by centrifugation at 12,000 g for 10 min. Phage lysates from the clones are then subjected to 4–15% gradient Native polyacrylamide gel electrophoresis (PAGE) for comparison to the native proteins purified from the original organisms. Precast gradient gels are purchased from BioRad Laboratories (catalog number 161-0902) and used according to the manufacturer's instructions for native gels to generate the gels shown in FIGS. 12a–m. An esterase preparation from the original strain, purified by HPLC to a single protein band is used as a control on the same gel. Alternatively, a native protein preparation which has not been purified to homogeneity but is purified to a single esterase activity can be used as a control. Protein bands possessing an esterase activity can be detected by applying an X-Acetate overlay and incubating at room temperature for 5–20 min. The relative mobility of the clone candidates can be compared to the native esterase protein.

FIGS. 12a–r shows the results of the typical comparison of the esterase activities detected in lambda clones compared to the host strain. The data generated for 107 hybrid phage clone candidates from 20 strains are summarized in Table 7. For each gene library screened, there is at least one clone candidate expressing an esterase protein with the mobility of the protein purified from the original strain. Several of the λ clone candidates express esterase activities which have mobilities that are different from the major component of the esterase specimens purified from the original strains. Similar sized bands possessing esterase activity are observed in the native organism as minor components (data not shown). These cloned ester hydrolyzing activities are given names depicted in Table 7.

Excision of the Plasmid Vector from the Phage—The lambda ZAP vector allows the phage clone to be conveniently converted into a plasmid vector to allow better physical characterization of the DNA insert and regulated expression of cloned genes. Induction of M13-specific replication by co-infection with the helper phage results in excision of a multi-copy plasmid carrying the cloned insert. 10 µl phage stocks of the lambda hybrids (with about $10^7$ Colony Forming Units (CFU)) and 1 µl of Exassist M13 helper phage (about $10^{10}$ CFU) are used to infect 20 µl of an overnight culture of the *E. coli* XL1 Blue grown in LB. After 20 min at 24° C., the cell suspension is transferred from one of the wells of a 96-well microtiter plate into a 15-ml culture tube, diluted with 2 ml of LB, grown overnight at 37° C. and 300 rpm, heated at 65° C. for 10 min, and cleared by centrifugation at 3000 g for 20 min. Excised plasmids packed in M13 particles are transduced into a lambda resistant strain, XLOLR, that does not permit the development of the M13 helper phage. Ten µl of excised phage lysate are mixed with 30 µl of the overnight culture of the *E. coli* XLOLR strain in one well of 96-well microtiter plate, incubated for 20 min at 37° C. to allow adsorption, diluted with 100 µl of LB, and incubated at 37° C. for 40 min to express the kanamycin (Km) resistance marker (neo) of the plasmid. Cells are plated onto two LB plates supplemented with 40 mg/ml Km. One of the plates also contains 50 µl of a 4% X-Acetate stock solution.

Preliminary experiments are performed by growing plates at 37° C. to demonstrate that a significant phenotypic segregation occurs with the transductant *E. coli* colonies expressing cloned thermophilic esterases. In an extreme case of the CE020 strain, very few colonies not expressing any esterase activity could be re-streaked from primary transductant colonies, which actively expressed esterase activity. Because of this segregation and apparent instability of plasmids containing the active clones, protocols for manipulation of most of the esterase clones needed to be modified as compared with the standard protocol of plasmid excision recommended by Stratagene. It was possible that the instability was due to the function of the cloned protein expressed in the cell, thus it was hypothesized that lowering the growth temperature might overcome the segregation problem, since the esterases were from thermophilic organisms and may not be as active at the lower temperatures.

Therefore, to overcome the problem of instability due to the activity of the esterase containing plasmids, cultivation of *E. coli* cells harboring thermophilic esterases is performed at 28° C. and 30° C., with the result that the effective phenotypic segregation is reduced. Thus, in the event that a cloned thermophilic esterase activity is lethal or partially lethal to the host cell, the growth temperature of the strain should be lowered to 30° C. or even room temperature. This is demonstrated in FIG. 13. After determining that temperature makes a large difference in stability of the clone phenotype, further experiments are carried out by plating all plasmid based clones at 26° C., generally for 48 hours. *E. coli* cells are plated in a medium containing X-Acetate to detect expression of cloned esterase by the plasmid, and a degree of segregation in or between primary colonies. Thus, growth of the transformed cells at a temperature which reduces the activity of the cloned esterase is important to the effective isolation of productive plasmids.

In the specific case, eight bacterial colonies derived from each of the phage clones are picked from the plates without X-Acetate, transferred into 100 ml of LB supplemented with 40 mg/ml Km in a 96-well plate and grown overnight. Progeny of these colonies are analyzed by a spot-test using X-Acetate containing agar. Several plasmid clones derived from each phage are chosen for further study by picking ones producing brightest blue halos and least amount of the esterase segregants.

Selection for the Stable Plasmid Variants—Since it is determined that the plasmid-based vectors carrying esterase genes are often unstable, stable variants of the plasmids are isolated. One method for such isolation is as follows. *E. coli* cells carrying excised plasmids are purified using LB plates supplemented with Km and a limited amount of X-Acetate to reduce any potential negative growth impacts from production of the somewhat lethal indole product of the colorimetric reaction. Colonies are selected by their phenotype (in general giving a modest growth rate and intensive blue color) and grown in 2 ml of LB with Km in 15 ml test tube for 48 hours to reach $OD_{600}$ of about 1.0 and harvested by centrifugation at 12,000 g for 1 min. Cell pellets are resuspended in 500 ml of 0.1M Phosphate buffer pH 7.0 and sonicated using a Sonics & Materials Vibra Cell 375 Watt sonicator at 4° C. Sonication is performed using a microtip, 40% max capacity, 50% time pulse for 45 sec. Lysates are centrifuged at 12,000 g for 5 min and tested for its relative esterase activity. Variants with the highest activity are selected for the next round of growth and analysis. Three rounds of plating followed by growth in liquid medium and activity assays are performed to verify the stability of the clones.

Deviations in specific esterase activity among variants from the same plasmid lineage can be reduced to a factor of three from over a factor of 100 by this procedure. Stabilization of the activity generally occurs at the level corresponding to the highest activity values detected in the first round of stabilization. This could indicate that *E. coli* host mutations are being selected which allow higher tolerance of the cloned protein, rather than simply suppressed activity of cloned toxic gene.

Physical Characterization of Plasmid Clones—Plasmid DNA is extracted from *E. coli* cells using a standard alkali lysis procedure, or other procedures known in the art (37). The DNA is digested with a series of restriction endonucleases such as EcoRI, BamHI, HindIII, PstI, EcoRV, and XbaI to establish digestion pattern of the clone and to determine a size of the cloned DNA fragment. The physical map patterns for the 24 selected production clones are depicted in FIG. 15. The insert sizes for each clone are calculated from this data and is summarized in Table 8.

TABLE 7

Cloned Esterase Candidates and Analysis

| # | Native Strain | Activity in phage lysate? | Recomb. Esterases Identified in Phage Lysate | Primary Clone Name | Derivative Plasmid Name | Active Plasmid Derivative | Specific Activity in Stabilized clone U/mg |
|---|---|---|---|---|---|---|---|
| 1 | S1 | + | E001 | lambdaTGE 1.1 | pTGE1.1 | + | 1536 |
| 2 | S1 | + | E001, E022 | lambdaTGE 1.2 | pTGE1.2 | + | |
| 3 | S1 | + | E001, E022 | lambdaTGE 1.3 | pTGE1.3 | + | |

TABLE 7-continued

Cloned Esterase Candidates and Analysis

| # | Native Strain | Activity in phage lysate? | Recomb. Esterases Identified in Phage Lysate | Primary Clone Name | Derivative Plasmid Name | Active Plasmid Derivative | Specific Activity in Stabilized clone U/mg |
|---|---|---|---|---|---|---|---|
| 4 | S1 | + | E001 | lambdaTGE 1.4 | pTGE1.4 | + | |
| 5 | S1 | + | E001 | lambdaTGE 1.5 | pTGE1.5 | + | 1489 |
| 6 | S1 | nt | nt | lambdaTGE 1.6 | pTGE1.6 | + | |
| 7 | S1 | nt | nt | lambdaTGE 1.7 | pTGE1.7 | + | |
| 8 | S1 | + | E022 | lambdaTGE 1.8 | pTGE1.8 | − | |
| 9 | 54 | + | E002 | lambdaTGE 2.1 | pTGE2.1 | + | 8300 |
| 10 | 54 | + | E023 | lambdaTGE 2.2 | pTGE2.2 | nt | 550 |
| 11 | 54 | + | E023 | lambdaTGE 2.3 | pTGE2.3 | + | |
| 12 | 54 | + | E002 | lambdaTGE 2.4 | pTGE2.4 | + | 2530 |
| 13 | 54 | + | E002 | lambdaTGE 2.8 | pTGE2.8 | − | |
| 14 | 50 | + | E003 | lambdaTGE 3.1 | pTGE3.1 | − | |
| 15 | 50 | + | E003 | lambdaTGE 3.2 | pTGE3.2 | + | 2610 |
| 16 | 50 | + | E003 | lambdaTGE 3.3 | pTGE3.3 | + | |
| 17 | 50 | + | E003 | lambdaTGE 3.4 | pTGE3.4 | + | |
| 18 | GP1 | + | E004 | lambdaTGE 4.1 | pTGE4.1 | − | |
| 19 | GP1 | + | E024 | lambdaTGE 4.2 | pTGE4.2 | + | |
| 20 | GP1 | + | E004 | lambdaTGE 4.3 | pTGE4.3 | + | 320 |
| 21 | GP1 | + | E004 | lambdaTGE 4.4 | pTGE4.4 | − | |
| 22 | GP1 | + | E004 | lambdaTGE 4.5 | pTGE4.5 | nt | |
| 23 | GP1 | + | E004 | lambdaTGE 4.6 | pTGE4.6 | + | 490 |
| 24 | C-1 | + | E005 | lambdaTGE 5.1 | pTGE5.1 | − | |
| 25 | C-1 | + | E025 | lambdaTGE 5.2 | pTGE5.2 | + | |
| 26 | C-1 | + | E005 | lambdaTGE 5.3 | pTGE5.3 | + | 984 |
| 27 | C-1 | − | | lambdaTGE 5.4 | pTGE5.4 | nt | |
| 28 | C-1 | + | E005 | lambdaTGE 5.5 | pTGE5.5 | nt | |
| 29 | 55 | + | E006 | lambdaTGE 6.1 | pTGE6.1 | − | |
| 30 | 55 | +/− | E026 | lambdaTGE 6.2 | pTGE6.2 | − | |
| 31 | 55 | + | E006 | lambdaTGE 6.3 | pTGE6.3 | + | 230 |
| 32 | 55 | + | E006 | lambdaTGE 6.4 | pTGE6.4 | − | |
| 33 | 55 | + | E006 | lambdaTGE 6.5 | pTGE6.5 | − | |
| 34 | 55 | + | E006 | lambdaTGE 6.6 | pTGE6.6 | − | |
| 35 | 46 | +− | *** | lambdaTGE 7.1 | pTGE7.1 | + | 210 |
| 36 | 46 | +− | *** | lambdaTGE 7.2 | pTGE7.2 | + | |
| 37 | 30 | + | E008 | lambdaTGE 8.1 | pTGE8.1 | − | |
| 38 | 30 | + | E008 | lambdaTGE 8.2 | pTGE8.2 | − | |
| 39 | 30 | + | E008 | lambdaTGE 8.3 | pTGE8.3 | + | |
| 40 | 30 | + | E008 | lambdaTGE 8.4 | pTGE8.4 | + | |
| 41 | 30 | + | E008 | lambdaTGE 8.5 | pTGE8.5 | + | 330 |
| 42 | 28 | − | | lambdaTGE 9.1 | pTGE9.1 | + | |
| 43 | 28 | − | | lambdaTGE 9.2 | pTGE9.2 | − | |
| 44 | 28 | + | E009 | lambdaTGE 9.3 | pTGE9.3 | + | 512 |
| 45 | 28 | + | E009 | lambdaTGE 9.4 | pTGE9.4 | + | >270 |
| 46 | 28 | + | E009 | lambdaTGE 9.5 | pTGE9.5 | − | |
| 47 | 28 | + | E009 | lambdaTGE 9.6 | pTGE9.6 | + | |
| 48 | 28 | + | E009 | lambdaTGE 9.7 | pTGE9.7 | + | |
| 49 | 29 | − | | lambdaTGE 10.1 | pTGE10.1 | − | |
| 50 | 29 | − | | lambdaTGE 10.2 | pTGE10.2 | − | |
| 51 | 29 | + | E010 | lambdaTGE 10.3 | pTGE10.3 | + | 546 |
| 52 | 29 | − | | lambdaTGE 10.4 | pTGE10.4 | + | >600 |
| 53 | 29 | + | E010 | lambdaTGE 10.5 | pTGE10.5 | + | |
| 54 | 29 | + | E010 | lambdaTGE 10.6 | pTGE10.6 | − | |
| 55 | 29 | − | | lambdaTGE 10.7 | pTGE10.7 | − | |
| 56 | 29 | + | E010 | lambdaTGE 10.8 | pTGE10.8 | + | |
| 57 | 31 | − | | lambdaTGE 11.1 | pTGE11.1 | + | |
| 58 | 31 | − | | lambdaTGE 11.2 | pTGE11.2 | − | |
| 59 | 31 | + | E011 | lambdaTGE 11.4 | pTGE11.4 | + | |
| 60 | 31 | + | E011 | lambdaTGE 11.9 | pTGE11.9 | + | |
| 61 | 31 | + | E011 | lambdaTGE 11.10 | pTGE11.10 | + | 1052 |
| 62 | 31 | − | | lambdaTGE 11.7 | pTGE11.7 | + | |
| 63 | 26b | + | | lambdaTGE 12.1 | pTGE12.1 | + | |
| 64 | 26b | + | | lambdaTGE 12.2 | pTGE12.2 | + | >600 |
| 65 | 26b | + | | lambdaTGE 12.3 | pTGE12.3 | + | |
| 66 | 26b | + | | lambdaTGE 12.4 | pTGE12.4 | + | |
| 67 | 26b | + | E029 | lambdaTGE 12.5 | pTGE12.5 | − | |
| 68 | 26b | + | E029 | lambdaTGE 12.6 | pTGE12.6 | − | |
| 69 | 27 | + | E013 | lambdaTGE 13.1 | pTGE13.1 | + | |
| 70 | 27 | + | E013 | lambdaTGE 13.2 | pTGE13.2 | + | 428 |
| 71 | 27 | + | E013 | lambdaTGE 13.3 | pTGE13.3 | + | 33 |
| 72 | 27 | + | E013 | lambdaTGE 13.4 | pTGE13.4 | + | |
| 73 | 34 | − | | lambdaTGE 14.2 | pTGE14.2 | − | |
| 74 | 34 | + | E014 | lambdaTGE 14.3 | pTGE14.3 | + | 460 |

TABLE 7-continued

Cloned Esterase Candidates and Analysis

| # | Native Strain | Activity in phage lysate? | Recomb. Esterases Identified in Phage Lysate | Primary Clone Name | Derivative Plasmid Name | Active Plasmid Derivative | Specific Activity in Stabilized clone U/mg |
|---|---|---|---|---|---|---|---|
| 75 | 34 | − | | lambdaTGE 14.4 | pTGE14.4 | − | |
| 76 | 34 | + | E014 | lambdaTGE 14.5 | pTGE14.5 | + | >1200 |
| 77 | 34 | + | E027 | lambdaTGE 14.6 | pTGE14.6 | + | >900 |
| 78 | 34 | − | | lambdaTGE 14.7 | pTGE14.7 | + | |
| 79 | 34 | + | E014 | lambdaTGE 14.8 | pTGE14.8 | − | |
| 80 | 34 | + | E014 | lambdaTGE 14.9 | pTGE14.9 | + | |
| 81 | 62 | + | E015 | lambdaTGE 15.1 | pTGE15.1 | + | |
| 82 | 62 | + | E015 | lambdaTGE 15.2 | pTGE15.2 | + | |
| 83 | 62 | + | E015 | lambdaTGE 15.3 | pTGE15.3 | + | |
| 84 | 62 | + | E015 | lambdaTGE 15.4 | pTGE15.4 | + | |
| 85 | 62 | + | E015 | lambdaTGE 15.5 | pTGE15.5 | + | |
| 86 | 62 | + | E015 | lambdaTGE 15.6 | pTGE15.6 | + | |
| 87 | 62 | + | E015 | lambdaTGE 15.7 | pTGE15.7 | + | |
| 89 | 62 | + | E015 | lambdaTGE 15.9 | pTGE15.9 | + | 4700 |
| 90 | 47 | + | E016 | lambdaTGE 16.1 | pTGE16.1 | + | 600 |
| 91 | 47 | + | | lambdaTGE 16.2 | pTGE16.2 | + | |
| 92 | 47 | + | E016 | lambdaTGE 16.3 | pTGE16.3 | + | >1200 |
| 93 | 47 | + | | lambdaTGE 16.4 | pTGE16.4 | + | |
| 94 | 47 | + | E016 | lambdaTGE 16.5 | pTGE16.5 | + | |
| 95 | 47 | + | | lambdaTGE 16.6 | pTGE16.6 | + | |
| 96 | 47 | + | | lambdaTGE 16.7 | pTGE16.7 | + | |
| 97 | C-3 | + | | lambdaTGE 18.1 | pTGE18.1 | + | nt |
| 98 | C-3 | + | | lambdaTGE 18.2 | pTGE18.2 | − | |
| 99 | 4 | + | E019 | lambdaTGE 19.1 | pTGE19.1 | + | >120 |
| 100 | 4 | + | E019 | lambdaTGE 19.2 | pTGE19.2 | + | |
| 101 | 4 | + | E019 | lambdaTGE 19.3 | pTGE19.3 | + | |
| 102 | 4 | + | E019 | lambdaTGE 19.4 | pTGE19.4 | + | 1960 |
| 103 | 4 | + | E019 | lambdaTGE 19.5 | pTGE19.5 | − | |
| 104 | 4 | + | E019 | lambdaTGE 19.6 | pTGE19.6 | + | |
| 105 | 7 | − | | lambdaTGE 20.1 | pTGE20.1 | + | |
| 105 | 7 | − | | lambdaTGE 20.2 | pTGE20.2 | + | |
| 106 | 7 | + | E020 | lambdaTGE 20.3 | pTGE20.3 | + | 2470 |
| 107 | 7 | + | E028 | lambdaTGE 20.4 | pTGE20.4 | + | |
| 108 | 7 | − | | lambdaTGE 20.5 | pTGE20.5 | + | |
| 109 | 7 | + | E020 | lambdaTGE 20.6 | pTGE20.6 | + | |
| 110–104 | 32 | − | | lambdaTGE 21.1–21.5 | pTGE21.1–21.5 | + | |
| 105 | 32 | + | E017b | lambdaTGE 21.6 | pTGE21.6 | + | |
| 106 | 32 | + | E017b | lambdaTGE 21.8 | pTGE21.8 | + | 930 |
| 107 | 32 | + | E017b | lambdaTGE 21.9 | pTGE21.9 | + | |

*** No protein detected by activity stain.

TABLE 8

Production Clone Data

| Production Enzyme | Selected Production plasmid | Recombinant Strain Name | Approx. DNA Insert Size[1] (kb) | Lane # on gels in FIG. 15 | Specific Activity in Typical Recombinant Crude Extract[2] (U/mg) |
|---|---|---|---|---|---|
| recE001 | pTGE1.1 | CE001 | 3.5 | 1 | 1,536 |
| recE001.5 | pTGE1.5 | CE001.5 | nt | nt | nt |
| recE002 | pTGE2.1 | CE002 | 2.5 | 2 | 8,300 |
| recE003 | pTGE3.2 | CE003 | 4.1 | 4 | 2,610 |
| recE004 | pTGE4.6 | CE004 | 3.4 | 5 | 490 |
| recE005 | pTGE5.3 | CE005 | 1.9 | 6 | 984 |
| recE006 | pTGE6.3 | CE006 | 6 | 7 | 230 |
| recE007 | pTGE7.1 | CE007 | 3.7 | 8 | 210 |
| recE008 | pTGE8.5 | CE008 | 3.2 | 9 | 330 |
| recE009 | pTGE9.4 | CE009 | 4.5 | 10 | 270 |
| recE010 | pTGE10.3 | CE010 | 2.5 | 11 | 546 |
| recE011 | pTGE11.10 | CE011 | 2.4 | 12 | 1,052 |
| recE029 | pTGE12.2 | CE029 | 4.2 | 13 | 600 |
| recE013 | pTGE13.2 | CE013 | 2.2 | 14 | 428 |
| recE014 | pTGE 14.3 | CE014 | 2.5 | 15 | 460 |
| recE015 | pTGE15.9 | CE015 | 3.5 | 17 | 4,700 |
| recE016 | pTGE16.1 | CE016 | 2 | 18 | 600 |
| recE016.3 | pTGE16.3 | CE016.3 | 1.8 | 24 | 1,200 |
| recE017b | pTGE21.8 | CE017b | 3.8 | 21 | 930 |
| recE019 | pTGE19.4 | CE019 | 3.7 | 19 | 1,960 |
| recE020 | pTGE20.3 | CE020 | 2.7 | 23 | 2,470 |
| recE022 | pTGE1.8 | CE022 | nt | nt | nt |
| recE023 | pTGE 2.2 | CE023 | 3.7 | 3 | 550 |
| recE024 | pTGE4.2 | CE024 | nt | nt | nt |
| recE025 | pTGE5.2 | CE025 | nt | nt | nt |

TABLE 8-continued

Production Clone Data

| Production Enzyme | Selected Production plasmid | Recombinant Strain Name | Approx. DNA Insert Size[1] (kb) | Lane # on gels in FIG. 15 | Specific Activity in Typical Recombinant Crude Extract[2] (U/mg) |
|---|---|---|---|---|---|
| recE027 | pTGE14.6 | CE027 | 2.6 | 16 | 900 |
| recE028 | pTGE20.4 | CE028 | 2.5 | 20 | nt |

[1]Insert sizes are estimated from the agarose gel. The estimated insert size is based on a vector size of 4.5 kb and the accuracy which could be achieved analyzing each of the six digestion patterns.
[2]Specific activity is calculated as the amount of p-nitrophenol produced in micromoles per minute per milligram of total protein as described in Example 2. The numbers reported here are from a typical production batch and may vary.

Generation of the Tag Sequences for PCR Identification of Esterase Containing Inserts The DNA sequences of the ends of the insert fragment carrying esterase genes can be determined by sequencing the ends of the inserts using standard T7 and S6 primers to produce unique tags of the cloned DNA. Sequence analysis can be carried out to design PCR primers which can uniquely amplify the DNA inserts from both the clones and the host organisms. These tags can be potentially used to generate this DNA fragment from the chromosome of the studied organisms using PCR technique.

Screening of the Cosmid library with an oligonucleotide probe—For cloning of enzymes which cannot be cloned by activity, other methods are used. A degenerative probe is prepared to the N-terminal sequence of the protein and hybridized to plaques from the recombinant phage bank. Alternatively, degenerate PCR amplification probes can be made using the N-terminal sequence or sequences obtained from the n-termini of internal protein fragments which have been obtained after proteolytic digestion of the enzyme. Using these sequences, a probe can be made from an amplified region between the N-terminus and an internal fragment or between two internal fragment sequences to identify a clone carrying the DNA encoding for the enzyme of interest.

EXAMPLE 18

Overproduction and Overexpression of Esterases

Production of recombinant esterase—The production strains used are listed in Table 8. Cloned enzymes are produced from *E. coli.* strain XLOLR. Alternatively, any suitable *E. coli* host may be used, including but not limited to HB101, C600, TG1 and XL1-Blue.

Several media can be used to produce cloned esterases. LB (10 gm/l tryptone, 5 gm/l yeast extract and 10 gm/l NaCl) and Terrific Broth (12 gm/l tryptone, 24 gm/l yeast extract and 4 ml/l glycerol supplemented with 100 ml of a sterile solution of 0.17M $KH_2PO_4$, 0.72M $K_2HPO_4$ after autoclaving) have been tested and the results from optimal growth conditions for the production strains listed in Table 9 below. Each media is supplemented with 10–50 μg/ml kanamycin.

Optimal production media depends on a number of factors, including media cost and specific activity of the produced proteins. TB media is a richer media and therefore more expensive. For instance, in the case of CE009, while more total units are produced in a single fermentation run, not enough is produced to justify the higher cost of the media. In addition, the specific activity is higher for the LB media preparation.

Fermentation production is run in 17 L Fermentors (15 L working volume/LH Fermentation) at 30° C., 600 RPM, and 0.5 vvm air flow. The seed train is established as follows. A loopful of a frozen production culture is used to inoculate 50 ml of production media in a 250 ml Erlenmeyer flask. The flask is incubated at 30° C. for two days (250 RPM) and then used to inoculate a 1 liter flask with 250 ml of production media. This flask is incubated 1 day at 30° C. and 250 RPM. The 1 liter flask is used to inoculate the fermentor.

Production of substantially purified preparations from a cell paste of strains producing the recombinant enzymes are carried out similar to the methods described in Example 4 and the specific protocols described in Examples 14–34 for the native proteins.

TABLE 9

Preferred media for Strains CE001–CE010.

| | LB | | | TB | | | |
|---|---|---|---|---|---|---|---|
| Strain | Specific Activity (U/mg) | Total Cell mass (g) | Total Units | Specific Activity (U/mg) | Total Cell mass (g) | Total Units | Current Growth media of choice* |
| CE001 | 213 | 0.41 | 4500 | 138 | 0.84 | 6725 | TB |
| CE002 | 98 | 0.52 | 1625 | 101 | 0.93 | 4575 | TB |
| CE003 | 272 | 0.42 | 4200 | 22 | 0.87 | 1025 | LB |
| CE004 | 208 | 0.47 | 3650 | 28 | 0.90 | 1350 | LB |
| CE005 | 123 | 0.40 | 3675 | 125 | 1.00 | 7600 | TB |
| CE006 | 85 | 0.42 | 2125 | 71 | 0.62 | 2175 | LB |
| CE007 | 9 | 0.39 | 225 | 19 | 0.75 | 500 | TB |
| CE008 | 71 | 0.51 | 2775 | 45 | 0.80 | 2350 | LB |
| CE009 | 109 | 0.42 | 2650 | 74 | 0.81 | 3050 | LB |
| CE010 | 418 | 0.42 | 2200 | 225 | 0.95 | 8375 | TB |

*Given current media costs

Optimization of esterase production—Further optimization of esterase production is performed by media studies in shake flasks followed by further optimization at the 1 liter to 20 liter scale. Depending on the enzyme, final fermentation conditions can involve either a fed-batch or continuous-fermentation process. Since the esterase activity being analyzed is intracellular, the use of a clear or defined media such as TT media is necessary. Organisms of interest are grown and cell pellets are collected by centrifugation. Pellets are disrupted by sonication and enzymes can be purified using the standard techniques of ion exchange and gel permeation chromatography described in Examples 3 and 4. Growth conditions including media composition, pH, and temperature are optimized at the small scale (ie. shake flasks, and 1 liter fermentors) to give the highest cell density while retaining the highest amount of enzyme.

Isolation of High-production mutants—Several simple mutagenesis schemes are used to try and isolate high-producing mutants of the different activities of interest. These include mutagenesis with uv-light or chemical mutagens such as ethylmethane sulfanoate (EMS) or N-methyl-N'-nitro-N-nitrosoguanidine (MNNG). The cells are treated with varying concentrations of the mutagen (or varying exposure times with uv light) according to methods described in Miller (38). Optimal concentrations of the different mutagens with different organisms vary. In general, killing concentrations allowing 80% survival for EMS, approximately 50% survival for MNNG, or 10–50% survival for uv light are desired. Mutagenized cultures are then grown up, allowing the mutagen to wash out and plated onto solid media.

Mutants are identified by applying an esterase plate screen to the cells. For example with an esterase screen, an agar overlay containing a colorimetric or fluorogenic substrate such as 5-bromo-4-chloro-3-indolyl-acetate or 4-methyulumbelliferyl acetate will be applied. Colonies which show a significant increase in activity by hydrolysis of the substrate will be identified.

Candidate mutants are then analyzed by native polyacrylamide gel electrophoresis and compared to the parental strain. Standard assay methods described in Example 2 or the rapid esterase/lipase screen described in Example 12 can then be applied to identify any differences in amounts of enzyme activity. If a production level increase is large an increased band on either a Native or SDS polyacrylamide gel after coomassie staining may be seen. Strains with multiple activities can also be differentiated in this way, verifying that the increase is in the enzyme of interest. It is then confirmed that the mutants have unaltered kinetic and substrate properties as the parental enzyme. The majority of mutations identified by this approach are expression mutations which can be isolated in either a promoter region, repressor molecule, or other controlling element. Most mutations in the enzyme structural genes will likely inactivate the enzyme, however, an enhanced activity may also be isolated. If it is apparent that the mutation increases the activity of the desired protein band but not the intensity of the band on a coomassie stained gel, the mutant is recharacterized to determine if it is a more efficient biocatalyst.

EXAMPLE 19

Esterase Screening Kit

A large subset of enzymes can be packaged into an easy to use screening kit to rapidly analyze a large number of enzymes at once. The kits are formulated to eliminate as many potential errors as possible and each enzyme is provided in a lyophilized form if possible near its optimal buffer and reaction conditions.

Many different formats for the kit are possible, from a series of glass vials, to varying size microtiter plates constructed of different plastic materials. The microtiter plate is favored because of its ease of handling and manipulating. Most microtiter plates are made of polystyrene however, which will not stand up to most organic solvents. For experiments which utilize aqueous solvent, the polystyrene is not a problem. Other more tolerant plastics such as polypropylene are available and are ideal for the kit. Large size 24-well microtiter plates which allow 3 ml of sample to be assayed (allowing enough sample for multiple TLC or HPLC analysis) have been developed. Other formats may also be useful for different applications.

Each kit is prepared by addition of a stir bar, buffer (0.1M Na phosphate pH 7.0) and 1 U of each enzyme to each well of a 24 well polypropylene tray (Tomtec). Enzymes are aliquotted into each well or vial in set amounts so that it can be assured that an equal amount of activity is provided for comparison. The entire kit is then lyophilized, sealed with heat seal foil (3M) and labeled. Separate experiments found that there was no significant loss in enzyme activity when proteins were lyophilized in the kit trays as suggested by earlier experiments comparing glass to plastic. In addition to enzymes, each kit contains four control wells that are composed of buffers at pH's from 6–9 since it was found that some of the substrates tested tend to be unstable in buffered solutions which can confuse positive results with autohydrolysis. The rest of the kit is composed of an instruction manual, a data sheet, a sample preparation vial a glass eye dropper and a plastic eye dropper. The kit is formulated in such a way that only solvent and substrate need be added to each well. The rapid-screen indicator dye method described in Example 12 can also be included in each well or vial. This makes a preliminary qualitative determination of enzyme effectiveness simple and fast.

EXAMPLE 20

Cloning and Characterization of Recombinant Proteins

The cloning and characterization of recombinant proteins from strain isolates which produced the native isolated protein (as listed in Table 1) was carried out as described in Example 37. Lambda expression vectors were isolated as described above (specific named isolates are shown in Table 7). E. coli clones harboring the excised hybrid phage-plasmids were derived as summarized in Table 7, and were finally selected for esterase activity by subsequent screening, which after 3 rounds of stabilizing procedure was calculated to approximate units of activity per mg of total cell protein obtained. Esterase activity stain gel used to screen positive phage library candidates for the recombinant proteins are shown in FIG. 12, which allowed the identification of alternative recombinant proteins as well. Production of the recombinant protein is carried out as described in Example 38, using TB for the media and purifying the enzyme as described for the native (nonrecombinant) protein in Example 4.

EXAMPLE 21

Sequencing of Recombinant Proteins

The isolation and cloning of the genes encoding for the enzymes of the instant invention results in DNA segments in which an open reading frame (ORF) may be found which corresponds to translated protein amino acid sequence. Sequencing of the DNA inserts which contain the corresponding nucleic acid sequence which encode for the protein enzymes can be conducted by the usual methods, either manually or using automated apparatus.

Once obtained, analysis of the nucleic acid sequence can reveal the presence of alternative start codons, a phenomenon recognized in the art, however the encoded protein enzyme will comprise at minimum a core protein ORF. FIG. 16A is an isolated nucleic acid sequence, and translated amino acid sequence which correspond to E001 enzyme ORF, alternative start codons are underlined. FIG. 16B is the cloned isolated nucleic acid sequence which contains the E001 ORF. FIG. 16C is an isolated nucleic acid sequence, and translated amino acid sequence which correspond to E009 enzyme ORF, alternative start codons are underlined. FIG. 16D is the cloned isolated nucleic acid sequence which contains the E009 ORF. FIG. 16E is an isolated nucleic acid sequence, and translated amino acid sequence which correspond to E011 enzyme ORF, alternative start codons are underlined. FIG. 16F is the cloned isolated nucleic acid sequence which contains the E011 ORF. FIG. 16G is an isolated nucleic acid sequence, and translated amino acid sequence which correspond to E101 enzyme ORF, alternative start codons are underlined. FIG. 16H is the cloned isolated nucleic acid sequence which contains the E101 ORF.

6. Sigurgisladottir, S., M. Konraosdottir, A. Jonsson, J. K. Kristjansson and E. Matthiasson. (1993) Lipase Activity of Thermophilic Bacteria from Icelandic Hot Springs. *Biotechnol Lett.* 15:361–366.

7. Margolin, A. L. (1993) Enzymes in the Synthesis of Chiral Drugs—Review. *Enzyme Microb Technol.* 15:266–280.

8. Hodgson, J. (1992) Controlling chirality in enzymatic synthesis. *Biotechnology.* 10:1093–1097.

9. Klunder, A., F. Gastel and B. Zwanenburg. (1988) Structural requirements in the enzymatic optical resolution of bicyclic esters using pig liver esterase. *Tetrahedron Letters.* 29:2697–2700.

10. Rao, Y. K., C. K. Chen and J. Fried. (1993) Enantiospecific and Regiospecific Partial Hydrolysis of Racemic Diol Diacetates by Pig Liver Esterase. *J Org Chem.* 58:1882–1886.

11. Faulds, C. B. and G. Williamson. (1993) Ferulic Acid Esterase from *Aspergillus niger*—Purification and Partial Characterization of 2 Forms from a Commercial Source of Pectinase. *Biotechnol Appl Biochem.* 17:349–359.

12. Chattopadhyay, S. and V. R. Mamdapur. (1993) Enzymatic Esterification of 3-Hydroxybutyric Acid. *Biotechnol Lett.* 15:245–250.

13. Frykman, H., N. Ohrner, T. Norin and K. Hult. (1993) S-Ethyl Thiooctanoate as Acyl Donor in Lipase Catalysed

TABLE 10

Summary of characteristics for E001–E020
ThermoCat ™ E001–E020 Spec comparison

| Biocatalyst | Specific Activity | MW | Temperature Opt. | Useful Range | pH Opt. | 50% Range | Half Life (hours) 40° C. | 60° C. |
|---|---|---|---|---|---|---|---|---|
| E001 | 0.5 u/mg | 22 kDal | 45° C. | RT-55° C. | 7.5 | broad | +++ | 34 |
| E002 | 1.0 u/mg | 28 kDal | 45° C. | RT-60° C. | 7.0 | broad | +++ | 30 |
| E003 | 0.5 u/mg | 28 kDal | 45° C. | RT-60° C. | 7.0 | broad | +++ | 60 |
| E004 | 0.6 u/mg | 36 kDal | 45° C. | RT-60° C. | 6.5 | <6.0–8.0 | +++ | 10 |
| E005 | 6.7 u/mg | 28 kDal | 45° C. | RT-60° C. | 7.0 | broad | +++ | 15 |
| E006 | 3.6 u/mg | 36 kDal | 45° C. | RT-60° C. | 6.5–7.0 | broad | +++ | 30 |
| E007 | 2.7 u/mg | 28 kDal | 35° C. | RT-60° C. | 7.0 | <6.0–8.0 | >480 | 90 |
| E008 | 1.5 u/mg | 28 kDal | 40° C. | RT-55° C. | 6.5–7.0 | <6.0–8.0 | 50 | <1 |
| E009 | 1.3 u/mg | 36 kDal | 45° C. | RT-50° C. | 6.5–7.0 | <6.0–8.0 | +++ | <1 |
| E010 | 4.9 u/mg | 46 kDal | 45° C. | RT-55° C. | 6.5 | <6.0–8.0 | +++ | <1 |
| E011 | 6.2 u/mg | 36 kDal | 45° C. | RT-60° C. | 6.5–7.0 | <6.0–8.0 | +++ | 4 |
| E012 | 10.7 u/mg | 28 kDal | 45° C. | RT-60° C. | <=6.0 | <6.0–7.5 | +++ | 240 |
| E013 | 5.3 u/mg | 36 kDal | 45° C. | RT-60° C. | 7.0 | <6.0–8.0 | >480 | 6 |
| E014 | 0.9 u/mg | 36 kDal | 45° C. | RT-50° C. | 7.0 | <6.0–8.0 | +++ | <1 |
| E015 | 3.0 u/mg | 36 kDal | 45° C. | RT-60° C. | >9.0 | 7.5–>9.0 | +++ | 6 |
| E016 | 1.2 u/mg | 28 kDal | 45° C. | RT-60° C. | nd | nd | +++ | 240 |
| E017b | 0.4 u/mg | 36 kDal | 40° C. | RT-50° C. | >9.0 | 7.5–>9.0 | +++ | 4 |
| E018 | 0.2 u/mg | nd | nd | nd | nd | nd | 120 | 30 |
| E019 | 0.9 u/mg | 30 kDal | 45° C. | RT-60° C. | >9.0 | broad | nd | 25 |
| E020 | 3.9 u/mg | 28 kDal | 45° C. | RT-60° C. | broad | broad | +++ | 12 |

*broad pH range refers to >50% activity through all pH tested (6.0–8.5)

REFERENCES

1. Barman, T. E. *Enzyme Handbook,* Springer-Verlag, Berlin-Heidelberg. 1969.
2. Dixon, M., E. C. Webb, C. J. R. Thorne and K. F. Tipton. *Enzymes,* Academic Press, New York. 1979.
3. Santaniello, E., P. Ferraboschi, P. Grisenti and A. Manzocchi. (1992) The biocatalytic approach to the preparation of enantiomerically pure chiral building blocks. *Chem. Rev.* 92:1071–1140.
4. Klibanov, A. (1989) Enzymatic catalysis in anhydrous organic solvents. *TIBS.* 14:141–144.
5. Fitzpatrick, P. and A. Klibanov. (1991) How can the solvent affect enzyme enantioselectivity. *J Am Chem Soc.* 113:3166–3171.

Resolution of Secondary Alcohols. *Tetrahedron Lett.* 34:1367–1370.

14. Hedstrom, G., M. Backlund and J. Slotte. (1993) Enantioselective synthesis of ibuprofen esters in aot/isooctane microemulsions by *Candida cylindracea* lipase. *Biotech and Bioeng.* 42:618–624.

15. Pozo, M. and V. Gotor. (1993) Chiral carbamates through an enzymatic alkoxycarbonylation reaction. *Tetrahedron.* 49:4321–4326.

16. Puertas, S., R. Brieva, F. Rebolledo and V. Gotor. (1993) Lipase Catalyzed Aminolysis of Ethyl Propiolate and Acrylic Esters—Synthesis of Chiral Acrylamides. *Tetrahedron.* 49:4007–4014.

17. Bonini, C., R. Racioppi, G. Righi and L. Viggiani. (1993) Polyhydroxylated Chiral Building Block by Enzymatic Desymmetrization of Meso 1,3 Syn Diols. *J Org Chem.* 58:802–803.
18. Chenevert, R. and R. Gagnon. (1993) Lipase-Catalyzed Enantioselective Esterification or Hydrolysis of 1-O-Alkyl-3-O-Tosylglycerol Derivatives—Practical Synthesis of (S)-(+)-1-O-Hexadecyl-2,3-di-O-Hexadecanoylglycerol, a Marine Natural Product. *J Org Chem.* 58:1054–1057.
19. Henly, R., C. J. J. Elie, H. P. Buser, G. Ramos and H. E. Moser. (1993) The Influence of Protecting Groups on Lipase Catalyzed Transesterifications—Enzymatic Resolution of Racemic cis-1,3-Cyclopentanediol Derivatives. *Tetrahedron Lett.* 34:2923–2926.
20. Patil, P., A. Chattopadhyay, S. Udupa and A. Banerji. (1993) Biotransformation with *Rhizopus arrhizus*: preparation of enantiomers of sulcatol. *Biotechnol Lett.* 15:367–372.
21. Ng, T. K. and W. F. Kenealy. Industrial Applications of Thermostable Enzymes. In *Thermophiles: General, Molecular, and Applied Microbiology.* Ed. by T. D. Brock, Wiley-Interscience, p. 197–215. 1986.
22. Wiegel, J. and L. G. Ljungdahl. (1986) The Importance of Thermophilic Bacteria in Biotechnology. *Crc Crit. Rev. of Biotech.* 3:39–108.
23. Saiki, R. K., D. H. Gelfand, S. Stoffel, S. J. Scharf, R. Higuchi, G. T. Horn, K. B. Mullis and H. A. Erlich. (1988) Primer-Directed Enzymatic Amplification of DNA with a Thermostable DNA Polymerase. *Science.* 239:487–491.
24. Stoflet, E. S., D. D. Koeberl, G. Sarkar and S. S. Sommer. (1988) Genomic Amplification with Transcript Sequencing. *Science.* 239:487–491.
25. Brumm, P., R. Hebeda and M. Teague. (1988) Purification and properties of a new, commercial, thermostable *Bacillis stearothermophilus* alpha-amylase. *Food Biotech.* 2:67–80.
26. Cowan, D. A. (1992) Enzymes from thermophilic archaebacteria: current and future applications in biotechnology. *Biochem Soc Symp.*
27. Mozhaev, V. V., K. G. Poltevsky, V. I. Slepnev, G. A. Badun and A. V. Levashov. (1991) Homogeneous solutions of hydrophilic enzymes in nonpolar organic solvents. New systems for fundamental studies and biocatalytic transformations. *Febs Lett.* 292:159–61.
28. Puchegger, S., B. Redl and G. Stoffler. (1990) Purification and properties of a thermostable fumarate hydratase from the archaeobacterium *Sulfolobus solfataricus. J Gen Microbiol.*
29. Hanner, M., B. Redl and G. Stoffler. (1990) Isolation and characterization of an intracellular aminopeptidase from the extreme thermophilic archaebacterium *Sulfolobus solfataricus. Biochim Biophys Acta.* 1033:148–53.
30. Smith, L. D., N. Budgen, S. J. Bungard, M. J. Danson and D. W. Hough. (1989) Purification and characterization of glucose dehydrogenase from the thermoacidophilic archaebacterium Thermoplasma acidophilum. *Biochem J.* 261:973–7.
31. Veronese, F. M., E. Boccu, O. Schiavon, C. Grandi and A. Fontana. (1984) General stability of thermophilic enzymes: studies on 6-phosphogluconate dehydrogenase from *Bacillus stearothermophilus* and yeast. *J Appl Biochem.* 6:39–47.
32. Tulin, E. E., Y. Amaki, T. Nagasawa and T. Yamane. (1993) A *Bacillus stearothermophilus* Esterase Produced by a Recombinant *Bacillus brevis* Stabilized by Sulfhydryl Compounds. *Biosci Biotechnol Biochem.* 57:856–857.
33. Sugihara, A., M. Ueshima, Y. Shimada, S. Tsunasawa and Y. Tominaga. (1992) Purification and characterization of a novel thermostable lipase from *Pseudomonas cepacia. J Biochem.* 112:598–603.
34. Sugihara, A., T. Tani and Y. Tominaga. (1991) Purification and characterization of a novel thermostable lipase from Bacillus sp. *J Biochem* 109:211–216.
35. Emanuilova, E., M. Kambourova, M. Dekovska and R. Manolov. (1993) Thermoalkalophilic Lipase-Producing Bacillus Selected by Continuous Cultivation. *FEMS Microbiol Lett.* 108:247–250.
36. Weber, J. M., S. Johnson, V. Vonstein, M. C. Casadaban and D. C. Demirjian. (1995) A chromosomal integration system for stable gene transfer into *Thermus flavus. Bio/Technology.* 13:271–275.
37. Sambrook, J., E. F. Fritsch and T. Maniatis. *Molecular Cloning, A Laboratory Manual,* Cold Spring Harbor Laboratory Press, NY. 1989.
38. Miller, J. H. *A short course in bacterial genetics,* Cold Spring Harbor Laboratory Press, Cold Spring Harbor. 1992.
39. Wu, S. H., Z. W. Guo and C. J. Sih. (1990) Enhancing the enantioselectivity of Candida lipase catalyzed ester hydrolysis via noncovalent enzyme modification. *J. Am. Chem. Soc.* 112:1990.
40. Kazlauskas, R. J., A. N. E. Weissfloch, A. T. Rappaport and L. A. Cuccia. (1991) A rule to predict which enantiomer of a secondary alcohol reacts faster in reactions catalyzed by cholesterol esterase, lipase from *Pseudomonas cepacia,* and lipase from *Candida rugosa. J. Org. Chem.* 56:2656.
41. Sugai, Y., H. Kakeya and H. Ohta. (1990) Enzymatic preparations of enantiomerically enriched tertiary α-benzyloxyacid esters. Application to the synthesis of (s) (−) frontalin. *J. Org. Chem.* 55:4643.
42. Whitesell, J. K., H. H. Chen and R. M. Lawrence. (1985) Trans-2-phenylcyclohexanol. A powerful and readily available chiral auxiliary. *J. Org. Chem.* 50:4663.
43. Lin, J., T., T. Yamazki and T. Kitazume. (1987) A microbially based approach for the preparation of chiral molecules possessing the trifluoromethyl group. *J. Org. Chem.* 52:3211.
44. Hagan, D. and N. A. Zaidi. (1992) *J. Chem. Soc. Perkin Trans.* 947.
45. Kitazume, T., T. Sato, T. Kobayashi and J. T. Lin. (1986) Microbial approach to the practical monofluorinated chiral synthons. *J. Org. Chem.* 51:1003.
46. Cohen, S. G., A. Milovanovic, R. M. Shultz and S. Y. Weinstein. (1969) On the active site of alpha-chymotrypsin. Absolute configurations and kinetics of hydrolysis of cyclized and noncyclized substrates. *J. Biol. Chem.* 244:2664.
47. Crout, D. H., V. S. B. Gaundet, K. Lauman and M. Schneider. (1986) Enzymatic hydrolysis of (+/−)-trans-1, 2-diacetoxycycloalkanes. A facile route to optically active cycloalkane-1,2-diols. *Chem. Comm.* 808.
48. Sabbioni, G. and J. B. Jones. (1987) Enzymes in organic synthesis. 39. Preparations of chiral cyclic acid esters and bicyclic lactones via stereoselective pig liver esterase catalyzed hydrolyses of cyclic mesodiesters. *J. Org. Chem.* 52:4565.
49. Kobayashi, S., K. Kamijama, T. Iimori and M. Ohno. (1984) Creation of novel chiral synthons with enzymes and applications to natural products synthesis. 15. Efficient introduction of chiral centers into cyclohexane rings. *Tetrahedron Lett.* 25:2557.
50. Ladner, W. E. and G. M. Whitesides. (1984) Lipase catalyzed hydrolysis as a route to esters of chiral epoxy-alcohols. *J. Am. Chem. Soc.* 106:7250.

51. Mohr, P., N. Wacspe-Saracevic, C. Tamm, K. Gawronska and J. K. Gawronski. (1983) A study of stereoselective hydrolysis of symmetrical diesters with pig liver esterase. *Helv. Chim. Acta.* 66:2501.

We claim:

1. A purified esterase enzyme preparation having at least 50% greater activity than crude extract, isolated from thermophilic organisms, of the genus Thermus, Bacillus, or Actinomyces, said preparation being obtained by lysing cells expressing the desired enzyme and removing most of the cell debris; wherein said enzyme preparation has the identified esterase activity, temperature profile, protein stability profile, and pH profile as that of an enzyme preparation selected from the group consisting of E001, E002, E003, E004, E005, E006, E007, E008, E009, E010, E011, E012, E013, E014, E015, E016, E017b, E018, E019, E020, E021, E022, E023, E024, E025, E026, E027, E028, E029, E100, and E101.

2. An isolated and purified esterase enzyme preparation, from thermophilic organisms of the genus Thermus, Bacillus, or Actinomyces, having at least two-fold greater activity than a crude extract, said enzyme preparation having the esterase activity, temperature profile, protein stability profile, pH profile and apparent molecular weight as that of an enzyme preparation selected from the group consisting of E001, E002, E003, E004, E005, E006, E007, E008, E009, E010, E011, E012, E013, E014, E015, E016, E017b, E018, E019, E020, E021, E022, E023, E024, E025, E026, E027, E028, E029, E100, and E101.

3. An isolated and purified esterase recombinantly produced by the expression of a DNA in a host cell, having the esterase activity, temperature profile, protein stability profile, pH profile and apparent molecular weight as that of an enzyme selected from the group consisting of E001, E002, E003, E004, E005, E006, E007, E008, E009, E010, E011, E012, E013, E014, E015, E016, E017b, E018, E019, E020, E021, E022, E023, E024, E025, E026, E027, E028, E029, E100, and E101.

* * * * *